(12) United States Patent
Kim et al.

(10) Patent No.: US 6,881,561 B1
(45) Date of Patent: Apr. 19, 2005

(54) ENDONUCLEASE OF IMMUNE CELL, PROCESS FOR PRODUCING THE SAME AND IMMUNE ADJUVANT USING THE SAME

(75) Inventors: Doo Sik Kim, Seoul (KR); Hyung Joo Kwon, Seoul (KR)

(73) Assignee: Cheil Jedang Corporation (KR)

( * ) Notice: Subject to any disclaimer, the term of this patent is extended or adjusted under 35 U.S.C. 154(b) by 136 days.

(21) Appl. No.: 09/722,776

(22) Filed: Nov. 27, 2000

Related U.S. Application Data

(63) Continuation of application No. PCT/KR98/00136, filed on May 30, 1998.

(30) Foreign Application Priority Data

May 30, 1998 (KR) .......................................... 1998-00136
May 27, 1998 (KR) .......................................... 1998-19176

(51) Int. Cl.[7] ............................. C12N 9/00; C12N 9/14; C12N 9/22; C07K 1/00
(52) U.S. Cl. ...................... 435/183; 435/195; 435/199; 530/350
(58) Field of Search ................................. 435/183, 195, 435/199; 530/350

(56) References Cited

FOREIGN PATENT DOCUMENTS

WO        WO96/02555        2/1996

OTHER PUBLICATIONS

Kwon et al (International Journal of Biochem & Cell Biology (vol. 30) pp 217–223, Feb. 1998.*

NATURE, vol. 374, No. 6522, Apr. 6, 1995, A.M. Krieg et al: "CpG motifs in bacterial DNA trigger direct β–cell activation", pp. 546–549.

SCIENCE, vol. 273, Jul. 19, 1996, Y. Sato et al: "Immunostimulatory DNA Sequences Necessary for Effective Intradermal Gene Immunization", pp. 352–354.

* cited by examiner

Primary Examiner—Mark Navarro
(74) Attorney, Agent, or Firm—Akerman Senterfitt

(57) ABSTRACT

The present invention relates to a novel endonuclease enzyme which is secreted from immune cell and recognizes bacterial DNA as foreign agent and processes it to produce about 10 bp single-stranded oligonucleotide including CpG motif which is involved in immune response. Also, the present invention relates to a process for producing the endonuclease which comprises culturing human B-lymphoblastic IM9 cell line or TPA-treated myelogenous U937 cell line on an appropriate medium to produce the said endonuclease and isolating the said endonuclease from the cell lysate or the culture medium. In addition, the present invention relates to an immune adjuvant comprising about 10 bp single-stranded oligonucleotide having CpG motif produced by treatment of bacterial DNA by endonuclease.

2 Claims, 42 Drawing Sheets

A

0  12  24  48 hr

B

0  12  24  48 hr

C

0  12  24  36  48 hr

D

1  2

A

B

A

IP : — preimmune anti-DNase I — anti-DNase I

10% FBS medium | human serum

B

IP : — preimmune protein A bead anti-DNase I

A B

A

B

SEQUENCE LISTING

<160> NUMBER OF SEQ ID NOS: 30

<210> SEQ ID NO 1
<211> LENGTH: 13
<212> TYPE: DNA
<213> ORGANISM: Escherichia coli

<400> SEQUENCE: 1
ttaaaacgtt cac                                                  13

<210> SEQ ID NO 2
<211> LENGTH: 13
<212> TYPE: DNA
<213> ORGANISM: Escherichia coli

<400> SEQUENCE: 2
aagtgaacgt ttt                                                  13

-continued

```
<210> SEQ ID NO 3
<211> LENGTH: 11
<212> TYPE: DNA
<213> ORGANISM: Escherichia coli

<400> SEQUENCE: 3
agcagcgcta a                                                          11

<210> SEQ ID NO 4
<211> LENGTH: 11
<212> TYPE: DNA
<213> ORGANISM: Escherichia coli

<400> SEQUENCE: 4
aattagcgct g                                                          11

<210> SEQ ID NO 5
<211> LENGTH: 15
<212> TYPE: DNA
<213> ORGANISM: Escherichia coli

<400> SEQUENCE: 5
ctcccggccg ccatg                                                      15

<210> SEQ ID NO 6
<211> LENGTH: 14
<212> TYPE: DNA
<213> ORGANISM: Escherichia coli

<400> SEQUENCE: 6
ttgggagctc tccc                                                       14

<210> SEQ ID NO 7
<211> LENGTH: 17
<212> TYPE: DNA
<213> ORGANISM: pUC/M13 forward

<400> SEQUENCE: 7
gttttcccag tcacgac                                                    17

<210> SEQ ID NO 8
<211> LENGTH: 17
<212> TYPE: DNA
<213> ORGANISM: pUC/M13 forward

<400> SEQUENCE: 8
caggaaacag ctatgac                                                    17

<210> SEQ ID NO 9
<211> LENGTH: 29
<212> TYPE: DNA
<213> ORGANISM: Escherichia coli

<400> SEQUENCE: 9
agagcagcgc taatgtctat cgatgattt                                       29

<210> SEQ ID NO 10
<211> LENGTH: 16
<212> TYPE: DNA
<213> ORGANISM: Escherichia coli

<400> SEQUENCE: 10
gtcaaaacgt tcacca                                                     16
```

<210> SEQ ID NO 11
<211> LENGTH: 91
<212> TYPE: DNA
<213> ORGANISM: Escherichia coli

<400> SEQUENCE: 11
ttaacaacgt tggggcgatt gagagcgatg gcgttgattt catgtaaacg aagctaacgt      60
ggtgaaaacg atgatggcgc acgcgagaaa t                                    91

<210> SEQ ID NO 12
<211> LENGTH: 16
<212> TYPE: DNA
<213> ORGANISM: Escherichia coli

<400> SEQUENCE: 12
cccatgacgc accgca                                                     16

<210> SEQ ID NO 13
<211> LENGTH: 28
<212> TYPE: DNA
<213> ORGANISM: Escherichia coli

<400> SEQUENCE: 13
attccatcgc catctcaaac ttcggtaa                                        28

<210> SEQ ID NO 14
<211> LENGTH: 46
<212> TYPE: DNA
<213> ORGANISM: Escherichia coli

<400> SEQUENCE: 14
tgcctcggag ttacctaatt ccatcgccat ctcaaacttc ggtaaa                    46

<210> SEQ ID NO 15
<211> LENGTH: 27
<212> TYPE: DNA
<213> ORGANISM: plasmid pET31F

<400> SEQUENCE: 15
cctttgacgt tgagtccacg ttcttta                                         27

<210> SEQ ID NO 16
<211> LENGTH: 15
<212> TYPE: DNA
<213> ORGANISM: plasmid pET31F

<400> SEQUENCE: 16
cctatctcgg tctat                                                      15

<210> SEQ ID NO 17
<211> LENGTH: 13
<212> TYPE: DNA
<213> ORGANISM: plasmid pKF3 from E. coli

<400> SEQUENCE: 17
tttacggttc ctg                                                        13

<210> SEQ ID NO 18
<211> LENGTH: 16
<212> TYPE: DNA
<213> ORGANISM: plasmid pKF3 from E. coli

<400> SEQUENCE: 18

<210> SEQ ID NO 19
<211> LENGTH: 22
<212> TYPE: DNA
<213> ORGANISM: plasmid pGEM-5Zf(-)

<400> SEQUENCE: 19
gtcgaccata tgggagagct cc                                      22

<210> SEQ ID NO 20
<211> LENGTH: 12
<212> TYPE: DNA
<213> ORGANISM: plasmid pGEM-5Zf(-)

<400> SEQUENCE: 20
acgcgttgga tg                                                 12

<210> SEQ ID NO 21
<211> LENGTH: 11
<212> TYPE: DNA
<213> ORGANISM: plasmid pGEM-5Zf(-)

<400> SEQUENCE: 21
agcttggcgt a                                                  11

<210> SEQ ID NO 22
<211> LENGTH: 16
<212> TYPE: DNA
<213> ORGANISM: Sequence from US patent 4921698

<400> SEQUENCE: 22
tttcctgcgt tatccc                                             16

<210> SEQ ID NO 23
<211> LENGTH: 59
<212> TYPE: DNA
<213> ORGANISM: Sequence from US patent 4921698

<400> SEQUENCE: 23
gctgatacgc tcgccgcagc cgaacgaccg agcgcagcga gtcagtgagc gaggaagcg    59

<210> SEQ ID NO 24
<211> LENGTH: 56
<212> TYPE: DNA
<213> ORGANISM: plasmid pGEM-T

<400> SEQUENCE: 24
cttcctcgct cactgactcg ctgcgctcgg tcgttcggct gcggcgacgg tatcag       56

<210> SEQ ID NO 25
<211> LENGTH: 38
<212> TYPE: DNA
<213> ORGANISM: plasmid pGEM-T

<400> SEQUENCE: 25
ggtctgacgc tcagtggaac gaaaactcac gttaaggg                     38

<210> SEQ ID NO 26
<211> LENGTH: 58
<212> TYPE: DNA
<213> ORGANISM: plasmid pGEM-T

```
-continued

<400> SEQUENCE: 26
taaagaacgt ggactccaac gtcaaagggc gaaaaaccgt ctatcagggc gatggccc          58

<210> SEQ ID NO 27
<211> LENGTH: 25
<212> TYPE: DNA
<213> ORGANISM: plasmid pGEM-T

<400> SEQUENCE: 27
ttcccaacga tcaaggcgag ttaca                                              25

<210> SEQ ID NO 28
<211> LENGTH: 16
<212> TYPE: DNA
<213> ORGANISM: plasmid pGEM-T

<400> SEQUENCE: 28
ctccgatcgt tgtcag                                                        16

<210> SEQ ID NO 29
<211> LENGTH: 34
<212> TYPE: DNA
<213> ORGANISM: Escherichia coli

<400> SEQUENCE: 29
tgctgttcgg caccaacaat cacgccgact ttaa                                    34

<210> SEQ ID NO 30
<211> LENGTH: 11
<212> TYPE: DNA
<213> ORGANISM: Homo sapiens

<400> SEQUENCE: 30
ttcgattcga t                                                             11
```

ENDONUCLEASE OF IMMUNE CELL, PROCESS FOR PRODUCING THE SAME AND IMMUNE ADJUVANT USING THE SAME

This application is a continuation of PCT/KR98/00136, filed May 30, 1998.

BACKGROUND OF THE INVENTION

1. Field of the Invention

The present invention relates to a novel endonuclease enzyme which is secreted from immune cells and recognizes bacterial DNA as foreign substance and processes it to generate approximately 10 bases single-stranded oligonucleotide including CpG motif known to involve immune response. In addition, the present invention relates to an immune adjuvant comprising the said single-stranded oligonucleotides of approximately 10 bases generated by the said endonuclease enzyme.

2. Description of the Prior Art

Mammalian animals develop immune systems to defend against foreign agents. The immune systems is classified into natural (nonspecific) immunity or acquired (antigen-specific) immunity. The innate or nonspecific immunity is a primary resistance against diseases caused by one species, and creates defence barrier as four types such as structural, physiological, endocytic and phagocytic, and inflammatory response. Representative examples of the structural defence barrier include skin and mucus. The physiological defence barrier include, for example, temperate, pH, oxygen pressure, and various aqueous soluble factors. The endocytic and phagocytic defence barrier refers to endocytosis and phagocytosis degradation systems in which foreign macromolecules are incorporated into and subsequently degraded by certain cells. The inflammation defence barrier is an inflammatory response which is evolved by various vasoactive and chemotactic agents generated by penetration of bacteria and followed by skin damage. Then, enzyme systems such as clotting, kinin, fibrinolytic or complement are activated. The acquired immunity is different from the innate immunity in that the former possesses specificity, diversity, memory and self and/or non-self recognition. The properties of the acquired immunity are derived from the humoral and cellular immunities which respond by B lymphocytes, T lymphocytes, antibody, cytokine, etc.

The immune response by penetration of microorganisms is generated by the innate mechanism which rapidly recognizes certain molecules of the microorganisms at the initiation stage of the penetration. The proteins and lipids present in microorganisms are well known as agents inducing immune systems which specifically respond to antigen. LPS, formyl methionine, lipoarabinomannan, peptidoglycan, etc. are well known as agents which directly activate the complement system (Maniack, P., and Kapple, J. W. (1994) Cell 76 323–332). Recently, it has been uncovered by many researchers that in mammalian animals, humoral and cellular immunities are activated by distinguishing their intrinsic DNA from bacterial DNA and recognizing the bacterial DNA as foreign agent and that also such bacterial DNA involves innate immunity.

From the fact that a great quantity of anti-DNA antibody is generated during systemic lupus erythematosus (SLE), autoimmune disease, DNA has been investigated in view of antigen or autoantigen. The anti-DNA antibody is serologically considered to be most important in connection with SLE, and functions as a major mediator involving kidney damage, skin eruption, arthritis, etc. (Tan, E. M. (1989) A Texbook in Rheumatology, 11th Ed. D. J. McCarty, cd. Led and Febiger, Philadelphoa, Pa., 1049; Isenberg, D. A., et al (1997) The role of antibodies to DNA in systemic lupus erythematosus-A review and introduction to an international workshop on DNA antibodies held in London, May 1996 Lupus 6, 290–304; Swaak, A. J. G., et al. (1979) Arthritis Rheum, 22, 226–235; and Isenberg, D. A., et al (1994) Arthritis Rheum. 37, 169–180). These antibodies were shown to bind to structure-determining factor present in ssDNA and dsDNA (Isenberg, D. A., et al (1994) Arthritis Rheum 37, 169–180; Pisetskyi, D. S. (1992) Rheum. Dis. Clin. North Am. 18,437–454: and Shoenfeld, Y., and Isenberg, D. A. (1939) Immunol. Today 10,123–126). Although the cause of SLE has not yet exactly revealed, recent studies strongly demonstrate that DNA antigen is significantly implicated in the diseases (Shlomchik, M. J., et al (1987) Proc. Natl. Acad. Sci. USA 84, 9150–9154; Shlomchik, M. J., et al (1990) J. Exp. Med 171, 265–292; and Tillman, D. M., et al (1992) J. Exp. Med. 176, 761–779). Researchers used normal mouse and autoimmune disease mouse to examine immune response to bacterial DNA (Gilkeson, G. S., et al. (1989) Clin. Immunol. Immunopathol. 51, 1482–1486; Gilkeson, G. S., et al (1993) J. Immunol. 151, 1353–1364; and Gilkeson, G. S., et al (1995) J. Clin. Invest. 95, 1398–1402). Unlike mammalian DNA, bacterial DNA possesses potent immunological properties which activate polyclonal B cell and produce antibodies having specificity in mouse (Gilkeson, G. S., et al (1995) J. Clin. Invest 95, 1398–1402; and Gilkeson, G. S., et al (1991) Clin. Immunol. Immunopathol, 59, 288–300). The activity degree is due to the fact that the base sequence motif present in bacterial DNA is different from the base sequence motif of mammalian DNA and may be recognized as foreign agent, i.e., non-self (Messina, J. P. et al (1993) Cell. Immunol. 147, 148–157,; Krieg, A. M. et al (1995) Nature 374, 546–549; and Halpern, M. D. et al (1996) Cell. Immunol. 167, 72–78). When normal mouse is challenged by bacterial DNA, it produces antibody capable of binding to not only bacterial dsDNA but also mammalian and bacterial ssDNA (Gilkeson, G. S. Et al (1991) Clin. Immunol. Immunopathol. 59, 288–300). However, any autoantibody which is cross-reactive to mammalian dsDNA was not produced. Unlike normal mouse, preautoimmune (NZB X NZW)F1. (NZB/W) mouse challenged by dsDNA produced cross-reactive antibody which is bound to mammalian dsDNA (Gilkeson, G. S., et al (1995) J. Clin. Invest. 95,1398–1402). AS such, when autoimmune disease mouse is immunized with bacterial DNA, the animal has the ability to produce anti-dsDNA antibody which is cross-reactive to mammalian DNA. That is because mistaken tolerance which auto-responding anti-dsDNA B cells produced by bacterial DNA in lack of immune-regulator in NZB/W mouse respond to their intrinsic DNA was taken place and thus pathogenic auto-antibodies responding to not only bacterial DNA but also their own DNA were increased (Whock, M. K. et al (1997) J. Immunol. 158, 4500–4506).

A production of antibody by stimulating and activating B cell with protein antigen is well known as the process in which protein antigen is processed by antigen presentation cell (APC) and is bound to major histocompatibility complex (MHC) to induce a presentation of antigen so that MHC-restricted T cell is activated and the activated T cell secrets cytokine to activate B cell (Parker, D. C. (1993) Annu. Rev. Immunol. 11, 331–360; and Clark, E. A., and Ledbetter, J. A. (1994) Nature 367, 425–428). It is also well known that lipoarabinomannan lipoglycans (LAMs), mycolic acid lipids, processed form of constitutive element of mycobacterial cell wall which are distinct from protein antigen can be presented by hCD1b (Beckman, E. M. et al (1994)Nature 372, 691–694; Bendelac, A. (1995) Science 269, 185–186; Sieling, P. A., at al (1995) Science 269, 227–230; and Prigozy, T. I., et al (1997) Immunity 6, 187) and hCD1c (Beckman, E. M., et al (1996) J. Immunol. 157, 2795–2803). CD1 family is nonpolymorphic cell surface glycoprotein which is encoded at the different sites from MHC molecule. Although CD1-T cell binding has not yet clearly defined, it was apparently suggested that mCD1d1 is recognized by $CD8^+$ and $CD4^+$ T cells (Castano A. R., et al (1995) Science 269, 223–226; Cardell, S., et al (1995) J. Exp. Med. 182, 993–1004) and hCD1b is recognized by $CD4^-$ and $CD8^-$ T cells (Bendelac. A.(1995) Science 269, 185–186). It is thus assumed that CD1 is involved in presentation of various antigens other than proteins found in pathogenic microorganisms. Many studies reported that DNA is involved in anti-DNA-specific B cell stimulation. Krishnan and Marion showed that immunization of mouse with the combination of DNA and peptide could induce anti-DNA antibody ( Krishnaa, M. R., and Marion, T. N. (1993) J. Immunol. 150, 4948–4957). Accordingly, in light of the fact that anti-DNA antibody is generated during various autoimmune disease, it is important to confirm as to whether activation of B cell for production of anti-DNA antibody depends on MHC-restricted T cell stimulation. Waisman suggested that specific activation of T cell by DNA is involved in DNA presentation by MHC class II molecule (Waisman, A., et al (1996) Cell, Immunol. 173, 7–14). That is, he showed the fact that DNA is bound to MHC class II molecule on APC surface and, as results, T cell can be proliferated specifically by DNA and, on the basis of the fact, proposed that DNA takes a critical role in autoimmune disease. However, there are no further studies and knowledge regarding processing and presentation mechanism of DNA antigen. For instance, the matters as to whether bacterial DNA is processed in APC and presented by MHC molecule as in protein antigen or whether other molecules are involved in such a presentation have not yet been explained.

Many researchers showed that vertebrate animals distinguish their intrinsic DNA from bacterial DNA and thereby the immune cell is activated by the bacterial DNA. The bacterial DNA recognized as non-self by vertebrate animals is characterized by generating nonmethylated CpG dinucleotide at high level. The extraordinary difference between bacterial DNA and vertebral DNA may be summarized as follows. First, bacterial DNA generates CpG dinucleotide of 16 dinucleotides at most level, but vertebral DNA generates ¼ of bacterial DNA. This means that CpG suppression exists in vertebral DNA. Second, methylation frequency of CpG dinucleotide present in bacterial DNA is low. While vertebral DNA shows 80% methylation, methylation of microbial cytosine is hardly found (Bird, A. P.(1995) Trends Genet. 11, 94–100). Thirds bacterial DNA is higher than vertebral DNA in the frequency of flanking two 5'-purines and two 3'-pyrimidines at both ends of CpG dinucleotide (Razin A., and Friedman, J. (1981) Prog. Nucleic Acid Res. Mol. Biol. 25, 33–52). The specific structure of the bacterial DNA called "CpG motif" was reported to activate immune response. That is, the activation of immune cell when two 5'-purines and two 3'-pyrimidines were flanked at both ends of CpG dinucleotide (mitogenic CpGs) is much higher compared to when other bases are flanked at both ends of CpG dinucleotide (non-stimulatory CpGs).

Many researchers used chemically synthesized oligodeoxyribonucleotide (ODN) in order to elucidate activation and action of immune cell by specific base sequence of bacterial DNA. Yamamoto and other researchers showed that bacterial DNA increased lytic activation of NK cell and induced the production of interferon-γ (IFN-γ) (Yamamoto, S., et al (1992) J. Immunol. 148, 4072–4076; Cowdery. J. S., et al (1996) J. Immunol. 156, 4570–4575; and Ballas, Z. K., et al (1996) J. Immunol. 157, 1840–1845). Kuramoto reported that such effects are associated with palindromic base sequence of CpG motif included in bacterial DNA ( Kuramoto, E., et al (1992) J. Cancer Res. 83, 1128–1131; and Kimura, Y., et al (1994) J. Biochem. 116, 991–994). In addition, it was reported that bacterial DNA is bound to DNA-binding protein and induces activation of B cell (Gilkeson, G. S., et al (1989) J. Immunol. 142, 1398–1402; Yamamoto, S., et al (1992) J. Immunol. 148, 4072–4076; Gilkeson. G. S., et al (1989) J. Immunol. 142, 1482–1486; Messina, J. P., et al (1991) J. Immunol. 147, 1759–1764; Field, A. K., et al (1967) Proc. Natl. Acad. Sci USA 58, 1004–1010; and Oehler, J. R., and Herverman, R. B. (1978) Int. J. Cancer 21, 221–220). That is, it is understood that the activation of B cell is promoted by CpG motif which consists of six(6) bacterial bases. Immune response by bacterial infection including B cell activation is characterized by producing immune-regulator cytokine(Van Damme, J., et al (1989) Eur. J. Immunol. 19, 163–168; and Paul, W. E., et al Adv. Immunol. 53, 1–29). It was also reported that CpG motif takes part in section of IL-12 involving cellular immunity and IL-6 involving humoral immunity (Halpern, M. D. et al (1996) Cell, Immunol. 167, 72–78; Yi, A. K., et al (1996) J. Immunol. 157, 5394–5402; and Klinman, D. M., et al (1996) Proc. Natl. Acad. Sci. USA 93, 2879–2883). Cytokines generated therefrom include IL-6 which plays a role in activating T cell and B cell (Uyttenhove, C., et al (1938) J. Exp. Med 167, 1417–1427; Muraguchi, A., et al (1999) J. Exp. Med. 167, 332–344; Le, J. M., and Vilcek, J. (1989) Lab. Invest. 61, 583–602; and Hirano, T., et al (1990) Immunol. Today 11, 443–449), IFN-γ which promotes the function of macrophage to eliminate intra- and extra-cellular pathogenic bacteria (Murray, H. W. (1990) Diagn, Microbial. Infect. Dis. 13, 411–421) and IL-12 which regulates production of IFN-γ and activates NK cell (Trinchieri, G. (1994) Blood 84, 4008–4027; Zhan, Y, and Cheers, C.(1995) Infect. Immun. 63, 1387–1390; and Bohn, E., et al (1994) Infect. Immun. 62, 3027–3032). IL-12 and IFN-γ take an important role to eliminate human pathogenic bacteria by increasing type 1 cytokine (Klinman, D. M., et al (1996) Proc. Natl. Acad. Sci. USA 93, 2379–2983; Zhan, Y, and Cheers, C. (1995) Infect. Immun. 63, 1387–1390; Bohn, E., et at (1994) Infect. Immun. 62, 3027–3032; and Heinzel, F. P., et al (1991) Proc. Natl. Acad. Sci. USA 88, 7011–7015). IL-6 stimulates the production of antibody by promoting growth and differentiation of T cell and B cell by type 2 cytokine (Uyttenhove, C., et al (1938) J. Ex. Med 167, 1417–1427; Muraguchi, A., et al (1988) J. Exp. Med. 167, 332–344; Le, J. M., and Vilcek, J. (1998) Lab, Invest. 61, 588–602; and Hirano, T., et al (1990) Immunol. Today 11, 443–449). Indeed, it was observed that mouse with knockout IL-6 gene was easily infected (Yi, A. K. et al (1996) J. Immunol. 157, 5394–5402; and Libert, C. et al (1994) Eur. J. Immunol. 24, 2237–2242). Thus, bacterial DNA is understood to induce the production of cytokine which is involved in cellular and humoral immunity. Recently, it has been further reported that the proliferation and generation of B cell is led by bacterial DNA (Krieg, A. M. et al (1995) Nature 374, 546–549; Liang, H., (1996) J. Clin. Invest. 98, 1119–1129; and Yi, A. K., et al (1996) J. Immunol. 156, 558–564). Study of Krieg showed that CpG motif present in ODN is essential to induce secretion of IgM while activating and proliferating B cell and that the expression of class II MHC molecule, typical phenomenon occurred when B cell was activated, is increased and cell cycle starts from $G_0$ to $G_1$. According to report of Sato (Sato, Y. et al (1996) Science 273, 352–354), it can be seen that when plasmid DNA including immunostimulatory DNA sequence (ISS) with short CpG motif is transfected into monocyte, amounts of IFN-α, IFN-β and IL-12 are increased. This result indicates that if plasmid including ISS is transfected into bone marrow stern cell, then surrounding macrophage and T cell at activated and in vivo rearrangement of the stern cell may be mistakenly occurred. Thus, vector for somatic or stem cell-replacing therapy should be designed not to include ISS. As contrast, one approach to improve the efficacy of vaccine is to design plasmid DNA so as to include many repetitive ISS.

In order to activate cell, bacterial DNA should be incorporated into the cell. It was found that ODN adsorbed on cell culture vessel fails to activate B cell (Krieg, A. M. et al (1995) Nature 374, 546–549) and that when oligonucleotide was lipofected, the incorporation thereof is increased while the activation of NK cell is greatly increased (Yamamoto, T., et at (1994) Microbiol. Immunol. 38, 831–836). It was also found that there was no significant difference between abilities of oligonucleotides to be bound to cell surface whether or not they include CpG motif (Krieg, A. M. et al (1995) Nature 374, 546–549; and Yamamoto, T., et al (1994) Microbiol. Immunol. 38, 831–836). Bennett showed that DNA incorporated into mononuclear cell was degraded in endosomal compartment ( Bennett R. M., et al (1985) J. Clin. Invest. 76, 2182–2190). Stacey showed that bacterial DNA was bound to transcription factor nuclear factor-kB in macrophage and the expression of TNF-α, IL1-β and plasminogen activator inhibitor-2 mRNA was greatly augmented (Stacey, K. J., et al (1996) J. Immuno. 157, 2116–2122). It was expected that incorporation of oligonucleotides into cell with mediation of receptor on cell surface would be taken place by endocytosis (Bennett, R. M. et al (1985) J. Clin. Invest. 76, 2182–2190). Also, a study was performed by using fluorescent-labelled phosphorothioate oligode oxynucleotides in peripheral blood, bone mellow cell and leukemia cell line (Loke, S. L., et al (1989) Proc. Natl. Acad. Sci. USA 86, 3474–3478; Yakubov, L. A., et al (1989) Proc. Natl. Acad. Sci. USA 86, 6454–6458; Zhao, Q., et al (1996) Blood 88, 1788–1795; Ribeiro J. M., and Carson D. A. (1993) Biochemistry 32, 9129–9136), but any property and mechanism thereof have not yet been defined.

Bacterial DNA has been so far understood to take a critical role in the immune system. It has been known that autoimmune disease SLE is occurred by the generation of anti-DNA antibody by bacterial DNA and that CpG motif of bacterial DNA is incorporated into immune cell to activate the cell and thereby promote secretion of cytokine and IgM. However there is no report as to what mechanism enables such critical bacterial DNA to produce antibody and how oligonucleotide having CpG motif is made in cell.

A novel endonuclease was identified by the inventors from human B-lymphoblastic IM9 cell and 12-O-tetradecanoylphorbol 13-acetate-treated differentiated myelogenous U937 and culture medium thereof using DNA-native-polyacrylamide gel electrophoresis (DNA-native-PAGE).

SUMMARY OF THE INVENTION

In one aspect the present invention provides novel endonuclease enzyme which is secreted from immune cell and which recognizes bacteria DNA as foreign agent and processes it to produce about 10 bp single-stranded oligonucleotide having CpG motif which is involved in immune response.

In another aspect, the present invention provides a process for producing the endonuclease of the present invention which comprises culturing human B-lymphoblastic IM9 or TPA-treated myelogenous U937 cell line on an appropriate medium to produce the said endonuclease and isolating the said endonuclease from cell lysates or culture medium.

In further aspect, the present invention provides an immune adjuvant comprising about 10 bp single-stranded oligonucleotide having CpG motif which is produced by treating bacterial DNA with the endonuclease of the present invention.

DETAILED DESCRIPTION OF THE INVENTION

Figure 1:
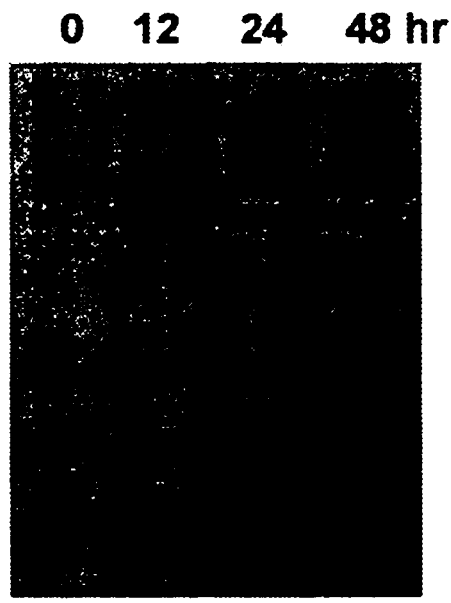
FIG. 1 shows the endonuclease activity of IM9 cells according to the present invention analyzed by DNA-native-PAGE. The endonuclease activity in IM9 cell lysates (A), medium (B) and medium cultured in serum-free (C) was detected by in-gel system. Bovine DNase 1 (lane) and cure medium endonuclease activity (lane2) were compared (D).
Figure 1:
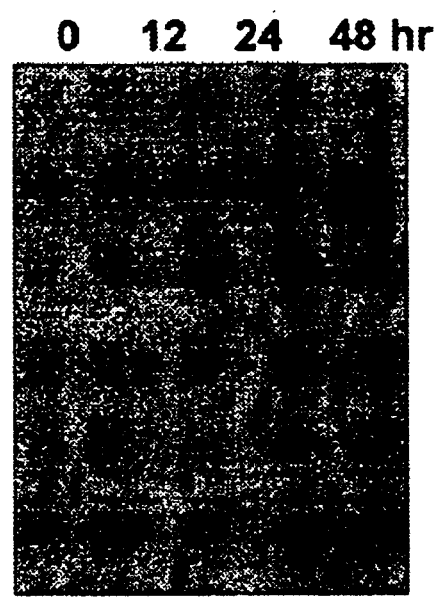
Figure 1:
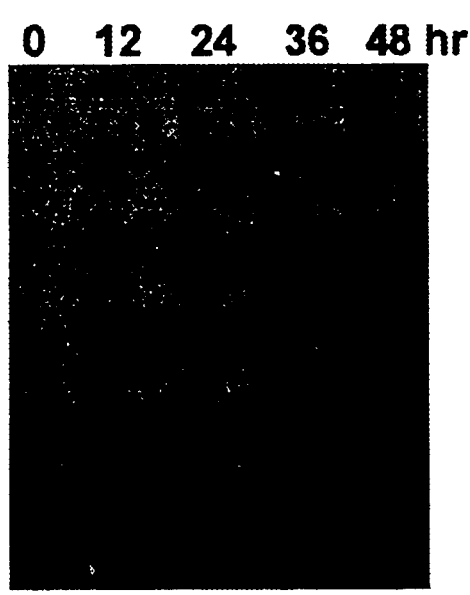
Figure 1:

The novel endonuclease was identified from IM9 cell lysates and culture medium using DNA-native-PAGE nuclease assay system. The molecular weight of the endonuclease was determined as 72.4 kD by SDS-PAGE. The endonuclease activity of the present invention was detected in IM9 cell nuclei during culture time and accumulation of the enzyme activity was shown in the IM9 cell nuclei protein extracts of the apoptotic cells. The signals for proliferation and differentiation of myelogeneous U937. cells are provided by extracellular stimuli such as lipopolysaccharide (LPS) and 12-O-tetradecanoylphorbil 13-acetate (TPA). Experimental results indicated that TPA has significant effect on the degree of endonuclease secretion. The enzyme activity was induced in U937 cells by LPS treatment, while the secretion of the enzyme was not detected in the culture medium. Using supercoiled plasmid DNA as a substrate, the endonuclease activity determined with the enzyme isolated from the cell culture medium. The endonuclease, with $Mg^{2-}$ alone, was able to catalyze the conversion of the plasmid DNA into linear form followed by further degradation, The pH optimum required for the catalytic activity was determined to be in the range of pH 6.6–7.4. Experimental results clearly demonstrated that the endonuclease activity of the immune cell lines is distinct from that of Dnase 1 in the DNA-native-PAGE assay system. Immunoprecipitation analysis using anti-DNase 1 antibody showed that the secreted endonuclease is not recognized by the antibody. The $Mg^{2+}$-dependent endonuclease characterized by the present invention appears to be distinct from the nuclease reported so far in several aspects including cation dependence for enzyme activity, electrophoretic mobility in native-PAGE, and optimum pH required for catalysis. The DNA fragments processed by the endonuclease activity were detected by Southern blot analysis in immune cell lines. The foreign DNA antigen partially processed in cell culture medium appears to be bound to the cell surface followed by incorporation into the cell. Using radiolabelled DNA fragments as a foreign antigen, the further processing of DNA antigen in the immune cell lines was demonstrated by autoradiography. Experimental results showed that the single-stranded DNA fragments of approximately 10 bases that are generated by the endonuclease were degraded by S1 nuclease reaction. The short single-stranded DNA sequence was successful to be hybridized with complementary synthetic oligonucleotide containing a CpG motif with unmethylated CpG dinucleotide flanked by two 5'-purines and two 3'-pyrimidines. The present invention demonstrates the presence and characteristics of a novel endonuclease that exists both in human immune cell lines and in their culture media. Also, the present invention shows that the endonuclease from immune cell recognizes bacterial DNA as a foreign substance and carries out immunological process by generating DNA fragments containing a CpG motif.

The present invention will be illustrated through the examples below.

EXAMPLE 1

Biosynthesis and Secretion of the Endonuclease from Immune Cell

From the fact that the enzymatic activity of DNase 1 is widely distributed over human tissue and body fluid, it was assumed that the enzyme possesses certain physiological in vivo functions in addition to the digestive function (Nadano D., et al (1993) Clin. Chem. 39, 448–452; and Yasuda T., et al (1993) Clin. Chim.Acta. 218, 5–16). DNase I is known to cleave internucleosomal DNA during apoptosis (Peitsch M. C., et al (1993) EMBO J. 12, 371–377). The presence of Dnase I in human serum and the biochemical properties thereof were reported (Love J. D., and Hewitt R. R.(1979) J. Biol. Chem. 254, 12588–12594; and Kishi K., et al(1990) Am. J. Hum. Genet. 47, 121–126). It was taught that serum DNase I is secreted from pancreas (Love J. D., and Hewitt R. R.(1979) J. Biol. Chem. 254, 12588–12594; and Ito K. et al (1984) J. Biochem. 95. 1399–1406) but studies on the secretion from other tissues are still required. A study of Messina showed that DNase I fails to produce CpG motif which activates B cell and macrophage since it completely degrades the bacterial DNA (Messina, J. P. et al (1991) i J. Immunol. 147,1759–1764). In addition, it was revealed from the study of Messina that bacterial DNA not treated by DNase I activates immune cell and promotes secretion of cytokine and IgM. These are consistent with the results obtained when cell was treated with ODN having CpG motif. Therefore, under the assumption that a new type of endonuclease which can recognize foreign DNA and produce CpG motif by processing is present in immune cell, the inventors conducted experiments using various immune cell lines to confirm the presence of the activity of such an endonuclease.

1-1 Cell Culture and Pretreatment

Human B-lymphoblastic (IM9 and RPMI1788) cell line, T-lymphoblastic(Molt-4 and Jurkat) cell line and myelogeneous (U937) cell line were purchased from American Type Culture Collection. Cells were cultured on RPMI1640 containing heated fetal bovine serum (FBS, Gibeo BRL) 10% while maintaining 4–5×10$^5$ cells/ml. Cell culture was carried out in incubator (Forma) including 5% $CO_2$ at 37° C. The number of cells and the viability of cells during culture were periodically measured by trypan blue exclusion method using hemocytometer. The viability of cells was kept at 95% or more over whole experiment. IM9 cell line was pretreated with actinomycin D (ACD, Sigma) at 0.33 ug/ml to confirm the biosynthesis of the endonuclease in cells (Cooper H. L., and Braverman R. (1977) Nature 269, 527–529). IM9 cell line was treated with ACD, cultured for 30 minutes and washed. Then, the enzymatic activity of the endonuclease was measured at regular intervals while the cells were cultured for 48 hours on RPMI1640 containing 10% FBS.

Figure 4:
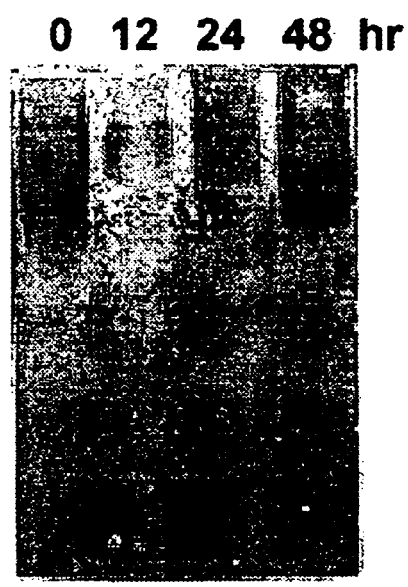
FIG. 4 shows the pretreatment of IM9 cells with actinomycin D and secretion of the endonuclease. The endonuclease activity in cell lysates (A) and culture medium (B) according to the present invention was analyzed at indicated culture periods after pretreatment.
Figure 4:
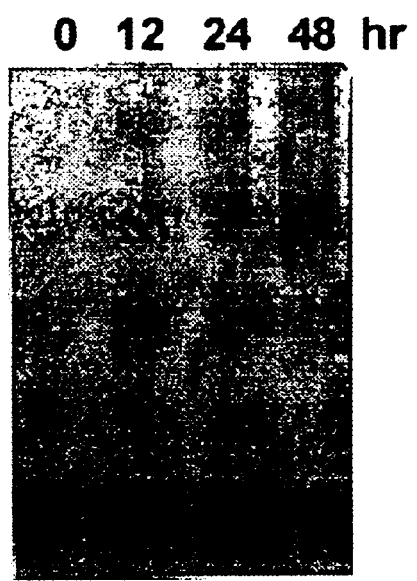
Figure 5:
FIG. 5 shows the comparative analysis of endonuclease activity in immune cell lines according to the present invention. The endonuclease activity in lysates (A) and culture medium (B) of each cell line was analyzed by the DNA-native-PAGE. Lane 1,10% FBS containing medium; lane 2, IM9; lane 3, RPMI1788; lane 4, Molt-4; lane 5. Jurkat; lane 6, U937.
Figure 5:

DNA-native-PAGE nuclease activity assay was performed to detect endonuclease enzyme activity in cell culture solution and cell lysate. The activity of the secreted endonuclease in tested cell cultures was observed only in IM9 cell line (FIG. 5B, lane 2). However, the endonuclease activity was always detected in cell lysate of human T-lymphoblastic Molt-4 cell line (FIG. 5A, lane 4) but not in cell culture solution. As for myelogeneous U937 cell line, B-lymphoblastic RPMI1788 cell line and T-lymphoblastic Jurkat cell line, the endonuclease activity was detected in neither cell lysate nor cell culture solution. As shown in FIG. 4, the biosynthesis of endonuclease in cell (FIG. 4A) and the secretion of endonuclease into cell culture solution (FIG. 4B) were remarkably decreased at the earlier period following the ACD pretreatment. These results indicate that there is close co-relationship between biosynthesis and secretion of endonuclease in IM9 cell line.

Figure 6:
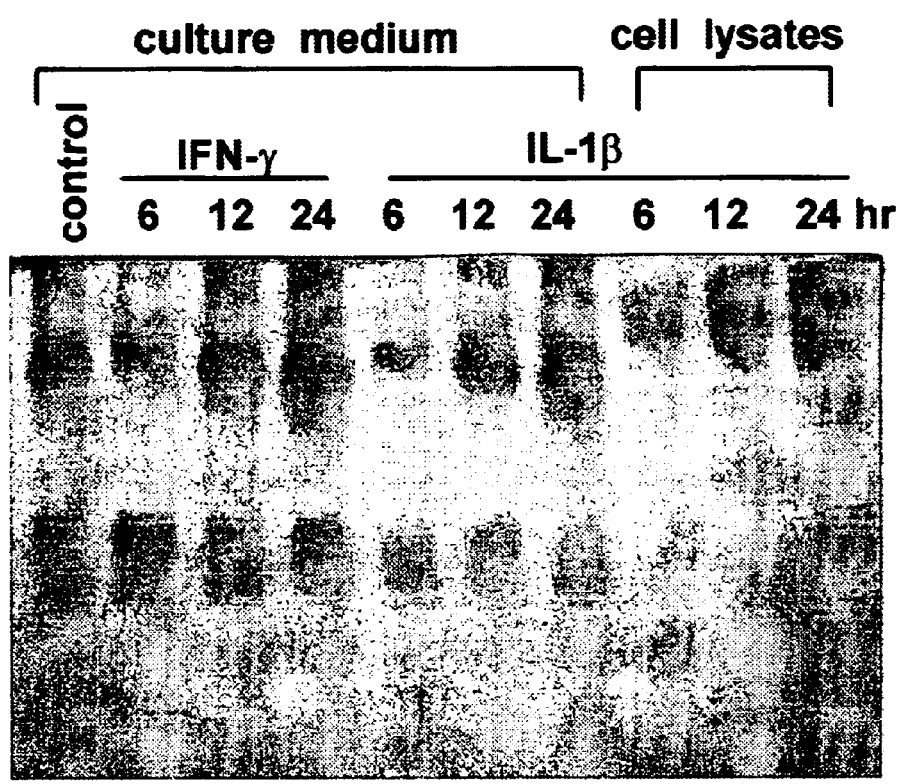
FIG. 6 shows the endonuclease activity of IFN-γ or IL-1β treated IM9 cell culture medium and cell lysates according to the present invention analyzed by DNA-native-PAGE. IM9 cells were treated with 10 units/ml of IFN-γ or IL-1β for the indicated culture times. Control IM9 culture medium in RPM 16–40 medium containing 10% FBS for 12 hours.

Cytokine involving immune response was treated with interferon-γ (IFN-γ, 10 units/ml, Genetech Inc.) and interleukine-1β (IL-1β, 10 units/ml, Genetech Inc.) to confirm the effects of cytikine on the biosynthesis and secretion of endonuclease. DNA-native-PAGE assay was conducted while culturing cells for 24 hours on medium containing interleukine. As shown in FIG. 6, such cytokines did not significantly influence on the secretion of endonuclease. Also, it was observed that neither lipopolysaccharide (LPS) nor tetradecanoylphorbol 13-acetate (TPA, Sigma) influenced on the secretion of endonuclease.

Figure 9:
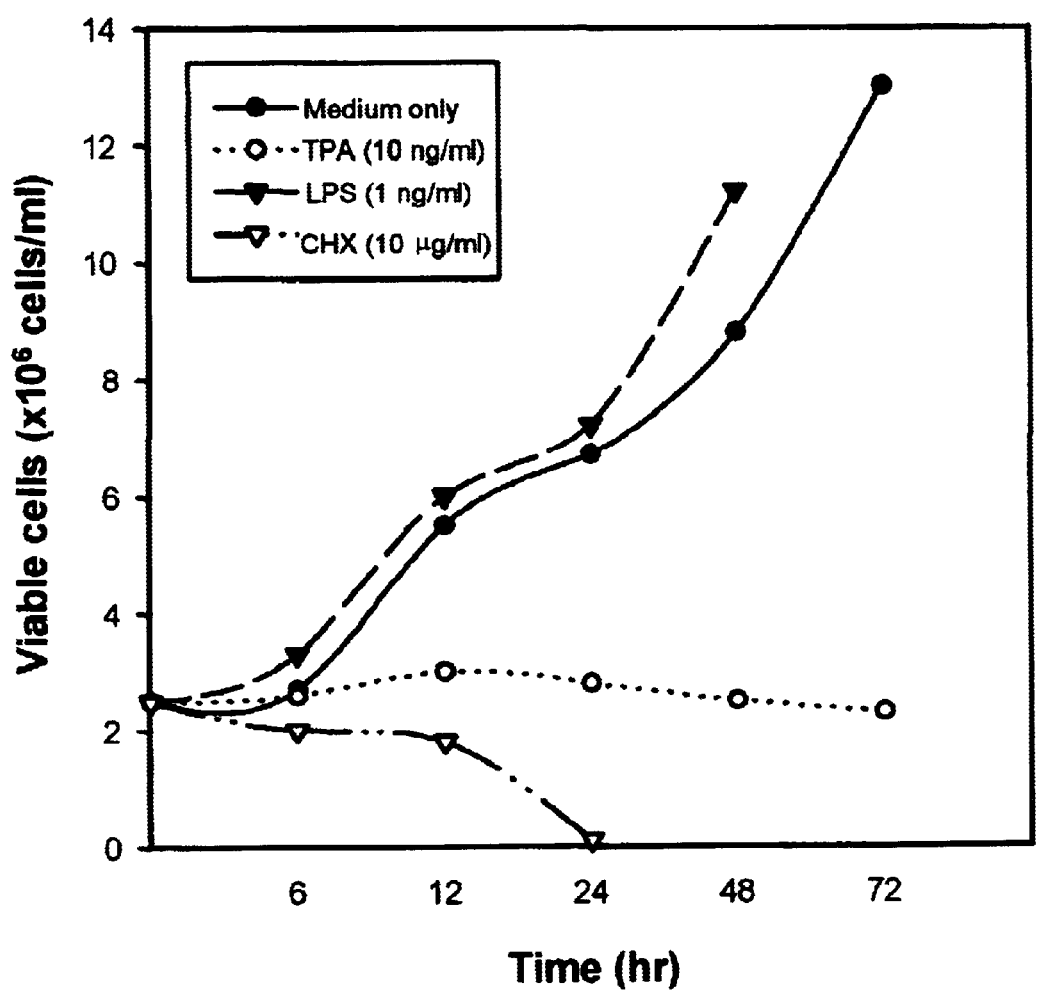
FIG. 9 shows the growth curve of TPA, LPS, and CHX treated U937 cells. U937 cells were treated with TPA (10 ng/ml), LPS (1ng/ml), and CHX (10/ml) as the indicated times. Cell number and viability were esteminated by trypan blue exclusion in a hemocytometer during culture time.
Figure 10:
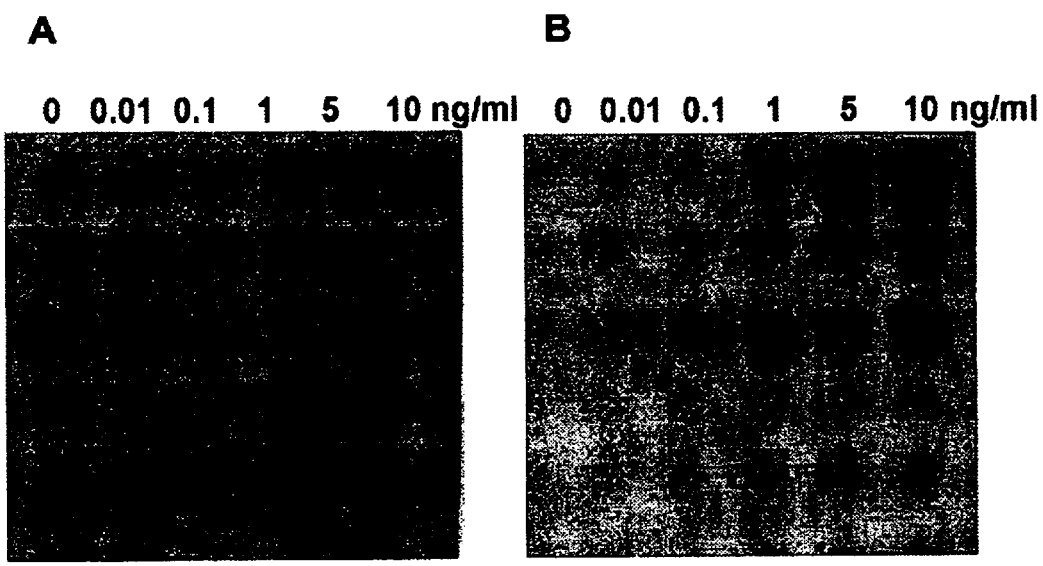
FIG. 10 shows the TPA-concentration dependent synthesis and secretion of endonuclease in U937 cells were analyzed by DNA-native-PAGE. Cell lysates (A) and culture medium. (B) was prepared by incubation for 24 hours at the indicated TPA concentration.
Figure 11:
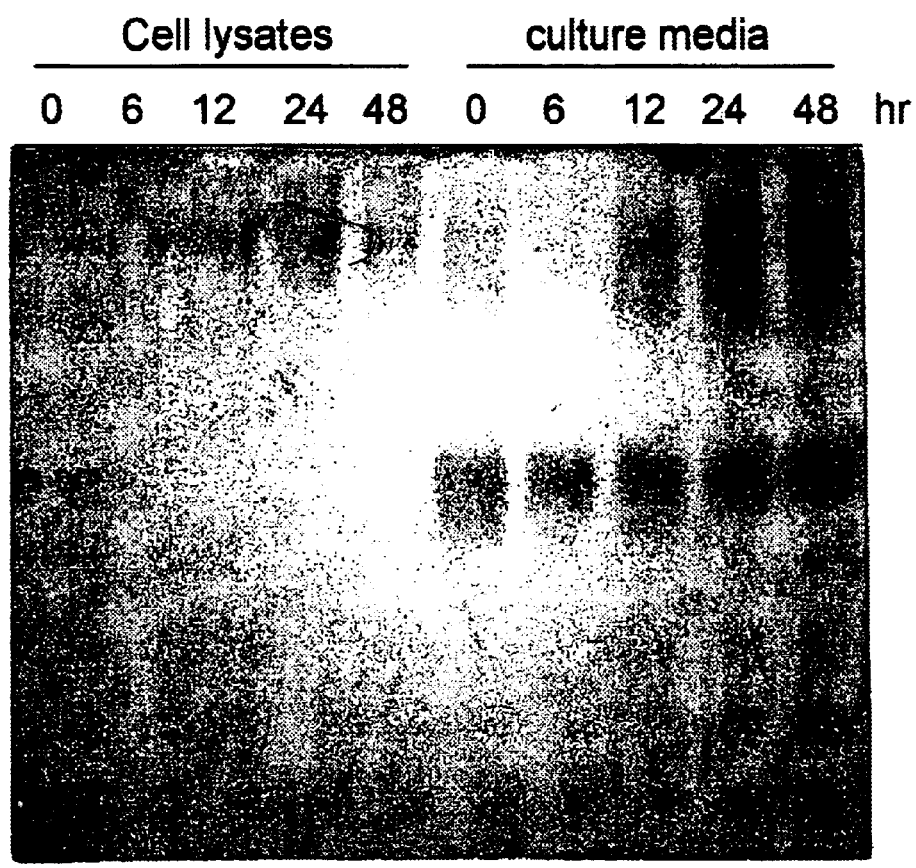
FIG. 11 shows the endonuclease activity of TPA treated U937 cell lysates and culture medium analyzed by in-gel system. U937 cells were treated with 10 ng/ml TPA for the indicated culture times.
Figure 12:
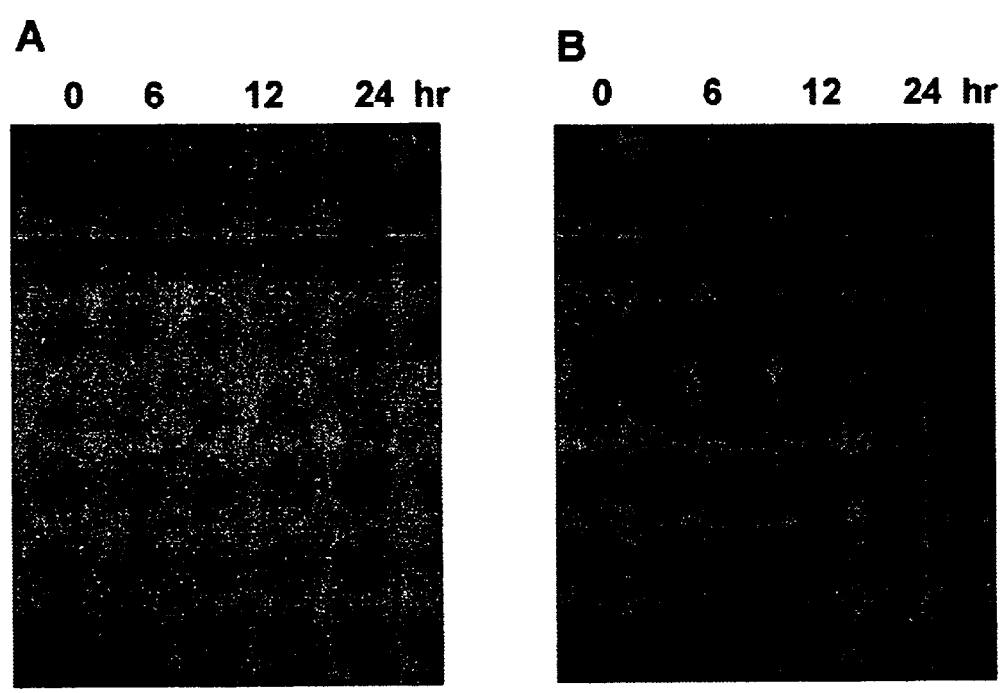
FIG. 12 shows the endonuclease activity of LPS treated U937 cell lysates and culture medium. The endonuclease activity in cell lysates (A) and medium (B) was analyzed at the indicated culture periods after 1 ng/ml LPS treatment by DNA-native-PAGE.
Figure 13:
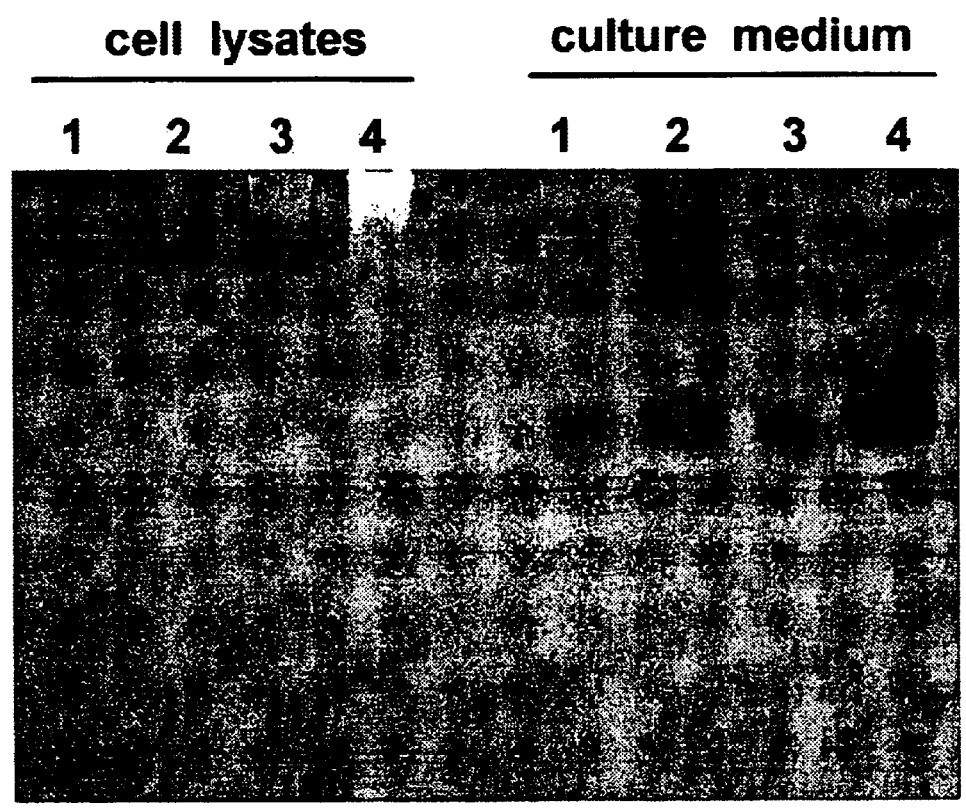
FIG. 13 shows the endonuclease activity of U937 cells treated with stimulatory factors (lane 1, U937 cell culture in RPMI1640 medium containing 10% FBS for 48 hr; lane 2, TPA(10 ng/ml) treatment for 48 hr; lane 3, LPS(1 ng/ml) treatment for 24 hr; and lane 4, CHX(10/ml) treatment for 12 hr).

The biosynthesis and secretion were observed while U937 cells were treated with TPA at different concentrations over indicated hours. U937 cell treated by cycloheximide (CHX, 10 ug/ml. Sigma) and LPS (1 ng/ml, Sigma) was compared with U937 cell treated by TPA. Cells were washed by phosphate-buffered saline (PBS, 137 mM NaCl, 2.7 mM Kcl, 10 mM $Na_2HPO_4$, 1.8 mM $KH_2P_4$, pH 7.4) and stained by Wright-Giemsa (Sigma) over cytocentrifuge slides to observe cell shape following the treatment of cells by various agents. As results, the cell shape of differentiated human myelogeneous leukemia cell line with TPA stimuli was takes to be mature and growth was stopped, but the proliferation of cell following stimulation of LPS was taken place. The growth curve of cell stimulated by such mitogens is shown in FIG. 9. It can be seen from FIG. 9 that U937 cell lines were differentiated by TPA to change the cell shape and ultimately growth was stopped and that the cells were proliferated by LPS. In addition, it was observed that the cells were killed by treatment of CHX, apoptosis-occuring agent. Additional experiments were carried out to confirm as to whether endonuclease is produced and secreted under such culture conditions. FIG. 10A shows that the biosynthesis of endonuclease in cell was increased in line with increased TPA concentration. FIG. 10B shows that endonuclease enzyme was secreted from cell at the same time that the biosynthesis of endonuclease in cell was increased Also FIG. 10A shows that the biosynthesis of endonuclease was rapidly increased at 10 ng/ml of TPA or more. FIG. 11 shows the results obtained when endonuclease activity was observed at regular intervals following treatment of U937 cell culture solution by 10 ng/ml of TPA. It can be seen that the biosynthesis and secretion of endonuclease enzyme was initiated at 6 hours after treatment of TPA and the peak thereof was achieved at 24 hours after treatment of TPA. FIG. 12 shows the results obtained when endonuclease activity was determined at regular intervals after treatment of cell by 1 ng/ml of LPS. The results indicate that endonuclease activity was detected in cell lysate at 12 hours after treatment of LPS and any endonuclease activity was not detected in cell culture solution over 24 hours. It was microscopically observed that U937 cell line was killed upon treatment by CHX, apoptosis-inducing agent, and such a treatment did not effect All on the biosynthesis of endonuclease (FIG. 13, lane 4). The endonuclease activity after treatment of U937 cell line by TPA, LPS and CHX was shown in FIG. 13.

1-2 Preparation of Cell Lysate and Determination of Endonuclease Activity on DNA-native-PAGE The cell culture was centrifuged at 1,500 rpm for five(5) minutes and supernatant was removed. The centrifuged cells were washed twice with cold PBS and resuspended in 0.5% Nonidet P-40(NP-40) buffer solution (lysis buffer solution) containing 150 mM NaCl, 10 mM Tris-HCl, pH 7.5, 1 mM EDTA and 1 mM PMSF to $1\times10^7$ cells/ml. After standing the solution at 4° C. for 15 minutes, it was centrifuged at 12,000 rpm, 4° C. for 15 minutes and supernatant was used as cell lysate.

A modified native polyacrylamide gel assay system was used to determine the endonuclease activity and identify its characteristics. By using Hoefer Tall Mighty Small(0.75 mm×8 cm×11 cm) vertical electrophoresis device, 7% polyacrylamide gel was ploymerized with supercoiled plasmid DNA(PGEM-T vector, 3.0 Kb, Promega) to the final concentration of 150/ml. 10 ug of protein sample of the cell culture solution or the cell lysate per well was loaded and then an electrophoresis was carried out at 4° C. After electrophoresis, the gel was washed three times with distilled water and reacted in a reaction buffer solution containing 20 mM Tris-HCl, pH 7.0, 1 mM $CaCl_2$ and 10 mM $MgCl_2$ (TCM buffer) at 37° C. for 4 hours while stirring. An enzyme activity of the endonuclease enzyme was observed while changing the reaction time to identify the reaction specificity of the enzyme on DNA-native-PGAE. The reacted gel was stained with TCM buffer solution comprising 1/ml ethidium bromide at 37° C. for 30 minutes and photographed with 302 nm transilluminator. The sites exhibiting nuclease activity on the gel were observed as black band on orange background. The standard for endonuclease activity was bovine pancreatic DNase I (RNase-free 10–50× $10^3$ units/ml, Boehringer Mannheim).

Enzyme activity in cell culture and cell lysate, along with sensitivity, can be determined by DNA-native-PAGE nuclease assay system designed for the present invention (FIG. 1). Intensive reaction bands were observed at the site exhibiting endonuclease activity in cell culture solution and cell lysate containing 10 ug of protein. The analyzed endonuclease biosynthesis and secretion of IM9 cells for indicated times are shown in FIG. 1. The endonuclease activity in cell lysate was constantly detected during 48 hour culture (FIG. 1A), but under the same reaction conditions, the endonuclease activity in cell culture solution was considerably accumulated (FIG. 1B). When IM9 cell culture was washed several times with PBS and then transferred to serum-free medium, the major band for endonuclease activity shown in FIG. 1B was detected as it was, but any DNase I enzyme activity was not detected (FIG. C). This result indicates that the endonuclease detected in IM9 cell culture and cell lysate was not derived from FBS which is an ingredient of medium composition on which the cells were cultured, but was synthesized in the cell and secreted into the medium. The weak band of nuclease activity rapidly migrated on the electrophoresis in the cell culture of FIG. 1B was identified as DNase I by comparing with bovine DNase I obtained from Boehringer Mannheim.

Figure 2:
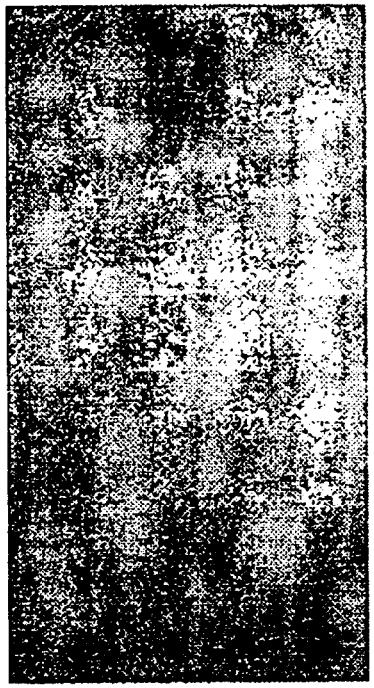
FIG. 2 shows the endonuclease activity of DNase 1 (A) and IM9 culture medium (B) analyzed by DNA-native-PAGE.
Figure 2:
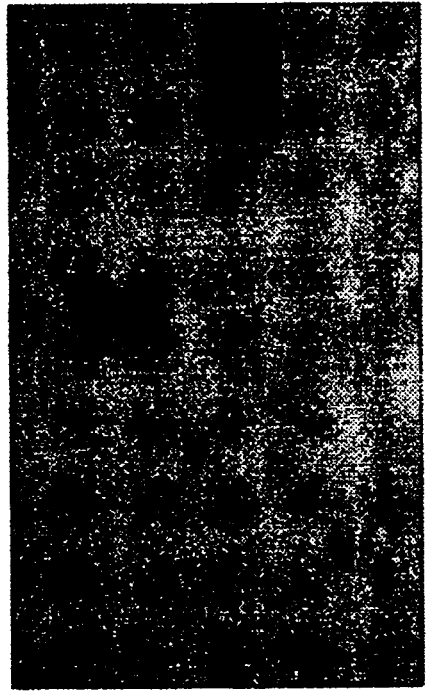

FIG. 2 shows the enzyme activity for 1 hour and 4 hours detected by DNA-native-PAGE under the conditions of different reaction solutions. When a reaction was performed in 20 mM Tris-HCl, pH 7.0, buffer solution containing 10 mM $Mg^{2+}$ for 1 hour, the activity was detected only in the endonuclease secreted by IM9 cell as shown in FIG. 2A. However, when an reaction was carried out for an extended time of 4 hours under the same reaction condition, DNase I present in FBS as well as purchased DNase I showed the enzyme activity on the same site. This result shows that the migration distance of the endonuclease synthesized and secreted by IM9 cell is different from the migration distance of DNase I on native-PAGE and the enzyme reactivity is also different from each other under a given reaction condition.

1-3 Production of Antibodies Against Dnase I and Immunoprecipitation

Blood was taken from tail of Sprague Dawley (SD, 150–250 g) to obtain preimmune serum Bovine pancreatic DNase I (Sigma) was digested into small fragments in sterile PBS for immunization. SD rats were immunized with 100 ug of the protein according to the standard method (Harlow, E., and Lane D. (1988) Antibodies, A laboratory manual, Cold Sping Harbor, N.Y.). 10 days after the rats were four times challenged, blood was taken and the antibody titer and specificity were assayed. Anti-DNase I antibodies in the serum containing DNase I were purified by using Immunopure plus protein A/G IgG purification kit (Pierce) and Separose-CL 4B bound by bovine DNase I. 50 ml of cell culture or 50 ml of human serum 10 times diluted to PBS was immunoprecipitated by beads to which the purified anti-DNase I antibodies and Protein A-Sepharose CL 4B were bound. The immunoprecipitation was performed at 4° C. for 6 hours while stirring. Immunoprecipitated supernatant was collected and the enzyme activity of endonuclease was detected on DNA-native-PAGE.

Figure 3:
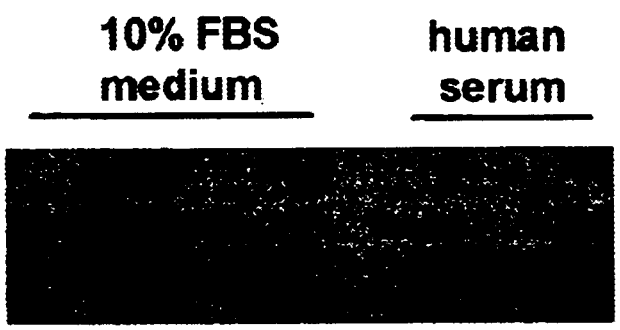
FIG. 3 shows the immunoprecipitation of endonuclease activity by anti-bovine DNase 1 antibody. The endonuclease activities in supernatant at after immunoprecipitation (IP) was estimated indicated anti-serum treatment by the DNA-native-PAGE as described under "Materials and Methods". A, 10% FBS medium and human serum; B, IM9 cell culture medium.
Figure 3:

FIG. 3A shows that the prepared antibodies recognize the DNase I derived from FBS and are cross-reactive with DNase I present in human serum. The preimmune serum did not recognize FBS and human serum DNase I. By using the DNase I prepared therefrom, the cross reactivity of the secreted endonuclease to each DNase I was detected. The supernatant immunoprecipitated from IM9 cell culture solution by anti-DNase I antibodies showed rapidly mobile DNase I enzyme activity, but the enzyme activity of the secreted endonuclease was not immunoprecipitated an recovered as it was (FIG. 3B). This result demonstrates that the endonuclease secreted from IM9 cell line is immunologically distinct from DNase I.

1-4 Partial Purification of Endonuclease Activity and Characterization

Figure 7:
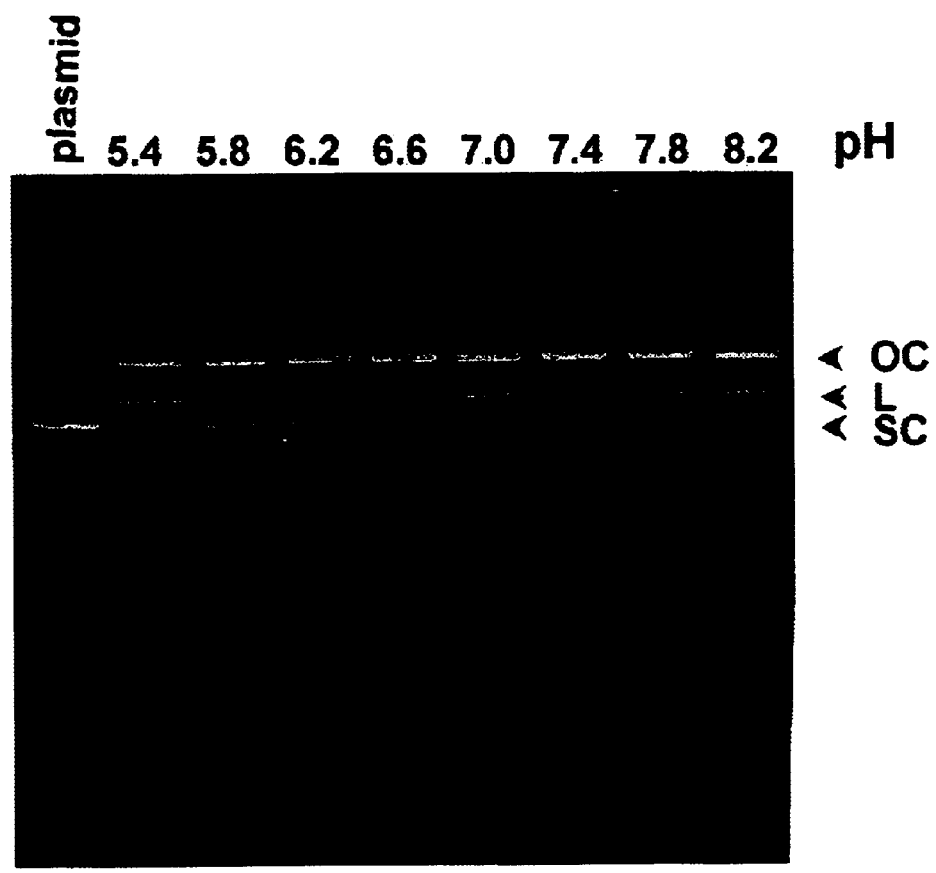
FIG. 7 shows the optimal pH for the endonuclease activity according to the present invention.
Figure 8:
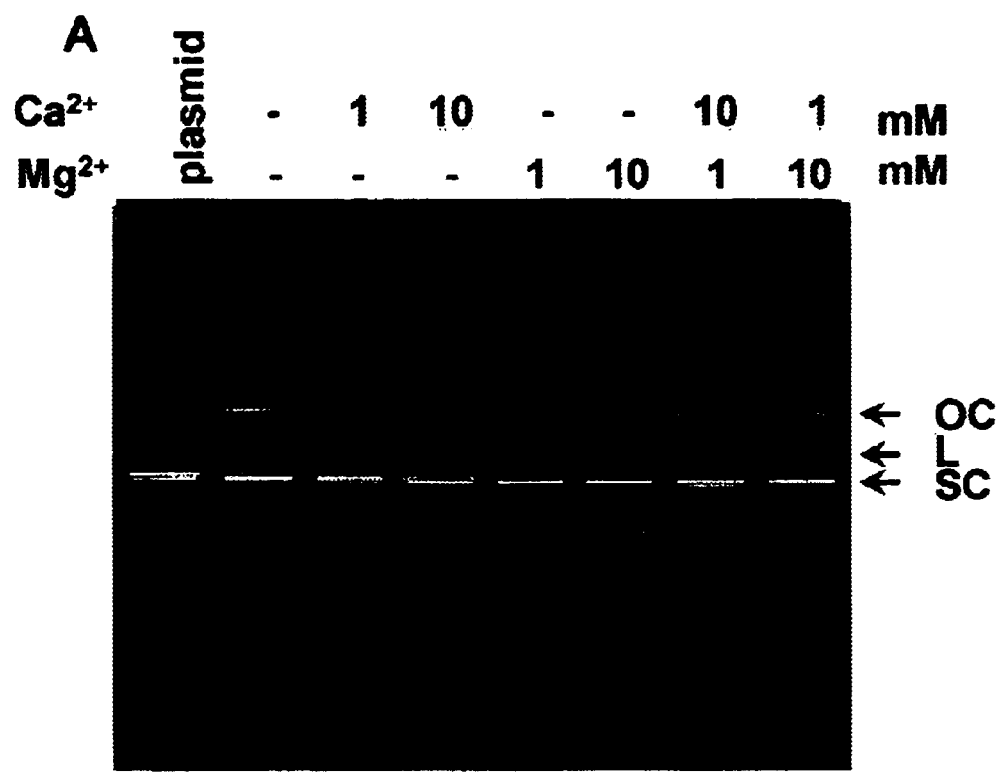
FIG. 8 shows the requirement of divalent cation for the endonuclease activity according to the present invention. A, the enzyme was reacted with 100 ng of plasmid DNA for 10 min at 37 in the presence or absence of the indicated concentration of $Ca^{2+}$ and/or $Mg^{2-}$ in 20 mM Tris-HCl, pH 7.0. B, the enzyme reaction was allowed for 180 minutes in the presence of 10 mM $Mg^{2-}$.
Figure 8:
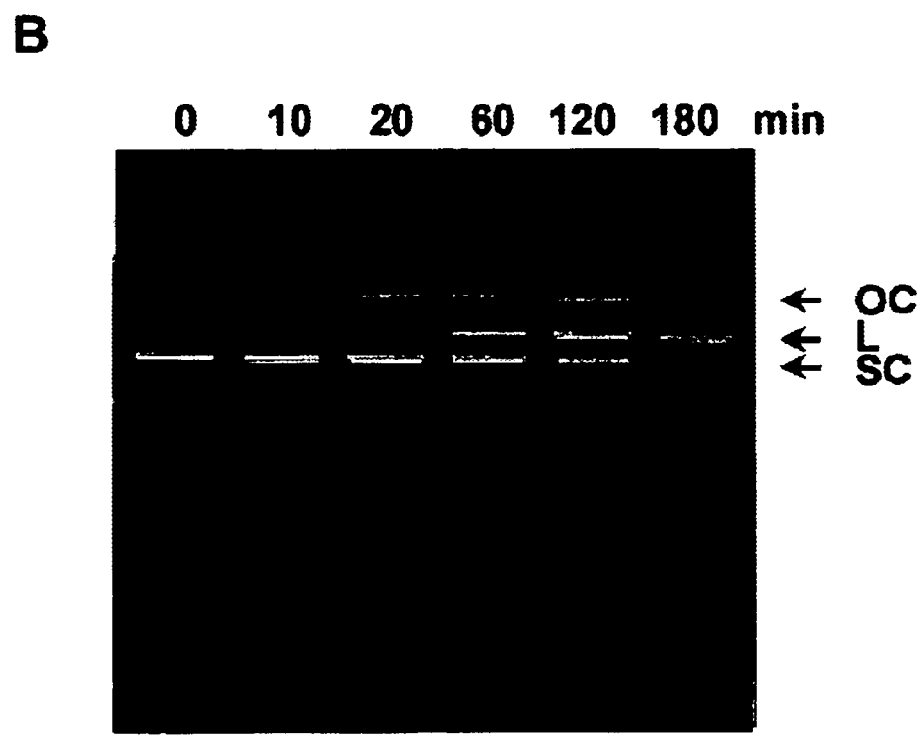

The protein band exhibiting activity by electrophoresis according to the above Example 1–2 was eluted to partially purify the endonuclease from the culture solution of IM9 cell. The protein band exhibiting nuclease activity was cut, fragmented into small pieces and transferred to eppendorf microtubes. Then, protein elution was carried out by using 20 mM Tris-HCl, pH 7.0, buffer solution at 4° C. for 10 hours while stirring. The sample was centrifuged at 4° C., 14,000 rpm for 10 minutes and the supernatant was divided by 20 ul. 20 ng of eluted protein sample was reacted with supercoiled plasmid DNA in 20 mM Tris-HCl buffer solution (pH 7.0) at 37° C. for 10 minutes. To determine the effect of pH on the enzyme activity, the enzyme activity was determined in 20 mM MOPS buffer solutions containing 1 mM $CaCl_2$ and 10 mM $MgCl_2$ having each different pH. To analyze the enzyme activity of endonuclease for indicated reaction time, enzyme reaction was observed in 20 mM Tris-HCl buffer solution (pH 7.0) containing 10 mM $MgCl_2$ at 37° C. for 180 minutes at regular intervals. After adding TE (10 mM Tris-HCl, pH 7.6, 1 mM EDTA) buffer solution containing DNA sample buffer solution (30% glycerol, 0.5% Bromophenol Blue and 0.5% xylene cynol), the reaction was stopped by adding ice. The reaction product was identified by conducting an electrophoresis on 1% agarose gel containing ethidium bromide (0.5 ng/ml). The isolated enzyme was determined as having the optimal activity at pH 7. However, the catalytic activity was detected at relatively broad range of pH (FIG. 7). The enzyme activity of endonuclease in 20 mM Tris-HCl (pH 7.0) buffer solution was dependent on $Mg^{2+}$ and was not affected by $Ca^{2+}$ (FIG. 8A). The enzyme was not activated in the range of 1 to 10 mM $Ca^{2+}$, but linear DNA was formed from plasmid by the enzyme activity depending on the concentration of $Mg^{2+}$ a formation of linear DNA by endonuclease for indicated reaction time was observed The conversion reaction of supercoiled plasmid DNA into linear DNA was started after 10 minutes reaction and was gradually increased until 60 minutes reaction. The nuclease activity was lasted for 180 minutes under the same experimental condition (FIG. 8B). Thus, it was confirmed that this enzyme converts supercoiled plasmid DNA into linear DNA and subsequently digest the DNA. This result demonstrates that the endonuclease activity secreted by IM9 immune cell is $Mg^{2+}$-dependent.

The present invention showed that the $Mg^{2+}$-depending endonuclease activity is produced in a constant amount and consistently secreted into the cell culture. Also, the fact that the endonuclease is different from the DNase I present in FBS and human serum was confirmed by the difference of migrating distance on native-PAGE and the immunoprecipitation result obtained by using anti-DNase I antibody. These indicate that the endonuclease of the present invention is distinct from the endonuclease reported so far to digest DNA in the process of apoptosis, in aspects of various biochemical properties such as cation-dependence for enzyme activity, mobility distance in native-PAGE, optimal pH required for activity, etc. Also, the fact that the enconuclease was produced and secreted at the time that U937 cell line was differentiated confirms that the endonuclease has an very important biological function which can recognize foreign DNA in immune reaction and digest it into a suitable size. The function of the endonuclease according to the present invention supports the report of Stacey that macrophage is activated when bacterial DNA is incorporated into the cell and the report of Higashi that cell toxicity mediated by mononuclear cell/macrophage may be occurred by nuclease (Stacey, K. J. et al.(1986) *J. Immunol.* 157, 2116–2122; and Higashi, N. et al.(1993) *Cell. Immunol.* 150, 333–342).

EXAMPLE 2

Identification of $Mg^{2+}$-dependent Endonuclease Inducing Internucleosomal DNA Fragmentation Apoptosis is defined as specific type of "cell death" such as chromatin condensation, membrane blebbing or chromatin fragmentation as various nucleosome sizes by endonuclease activity (Wyllie, A. H., et al (1984) J. Pathol. 142, 67–77; Wyllie, A. H. (1980) Nature 284, 555–556; and Kerr, J. F. R., et al (1972) Cancer. 26, 239–257).

Endonuclease activation is significantly responsible for apoptosis process (Arends, M. J., and Wyllie. A. H. (1990) J. Pathol. 136,593–608). Many researchers suggested that there are various enzymes which involve nucleosome fragmentation. Examples of enzymes involving internucleosomal DNA fragmentation include DNase I (Peitsch M. C., et al (1993) EMBO J. 12, 371–377), DNase II (Torriglia A., (1995) J. Biol. Chem. 270, 29579–29585; and Barry M. A., and Eastman A. (1993) Arch. Biochem. Biophys. 300, 440–450), and NUC-18 (Wawabata, H., et al (1997) Biochem. Biophys. Res. Commun. 233, 133–138). Also, there are many reports proposing that internucleosomal DNA in various types of tissue and cell can be fragmented by $C^{2+}/Mg^{2+}$-dependent endonuclease (Stratling W. H., et al (1984) J. Biol. Chem. 259, 5893–5898; Pandey S., et al (1997) Biochemistry 36, 711–720; and Ribeiro J. M. and Carson D. A.( 1993) Biochemistry 32, 9129–9136) or $Mg^{2+}$-dependent endonuclease (Anzai N., et al (1995) Blood 86, 917–923; Kawabata H., et al (1993) Biochem. Biophys. Res. Commun. 191, 247–254; Sun X. M., and Cohen G. M. (1994) J. Biol. Chem. 269, 14857–14860; and Wawabata, H, Anzai, N., et al (1997) Biochem. Biophys. Res. Commun. 233,133–138). However, it has not yet demonstrated that each of many endonucleases is implicated with different multiple cell systems or that when cell death is actively taken place in all types of cell, there exists certain unknown enzyme which works for chromtin fragmentation. Therefore, it has been required to characterize endonuclease involving apoptosis and define mechanism thereof.

The biosynthesis of endonuclease enzyme by human B-lymphoblastic IM9 cell line and the isolation of the endonuclease by DNA-native-PAGE were illustrated in the above Example 1. It was now found that the isolated endonuclease enzyme is distinguished from any endonuclease known so far in aspects of electrophoretic mobility in native-PAGE, optimum pH required for catalysis and divalent cation dependence for enzyme activity.

It was also found by the inventors that the activity of the enzyme which appears to be identical with the endonuclease present in the cell culture solution and cell lysate prepared by the above Example is detected in cell nucleus and the enzyme is deposited in the nucleus during apoptosis process. The fact that such endonuclease induces nucleosomal fragmentation in nucleus may be interpreted as depense action in that the cell tarketed to be killed is eliminated by such action. It was demonstrated by agarose gell eletrophoresis that when IM9 cell line was treated by CHX, oligonucleosomal fragments of DNA were generated. The generation of the fragments is known as an apex of biochemical phenomenon on apoptosis. In addition, typical DNA fragmentation was found when the nucleus isolated from IM9 cell line was reacted in the presence of $Mg^{2+}$. DNA fragmentation by autodigestion was identifed to be $Mg^{2+}$-dependent and $Ca^{2+}$-independent. The activity of endonuclease enzyme present in nucleus was also observed by DNA-native-PAGE assay system. The optimum pH for the activity of the enzyme was between 6.5 and 7.5. These results demonstrate that the endonuclease synthesized and secreted by IM9 cell line as described in the above Example 1 is identical with the enzyme present in nucleus of IM9 cell line. It is assumed that the endonuclease is closely related to $Mg^{2+}$-dependent endonuclease reported by many reasearchers to be present in various tissues and cells (Anzai N., et al (1995) Blood 86, 917–923; Kawabata H., et al (1993) Biochem Biophys. Res. Commun. 191, 247–254; Sun X. M., and Cohen G. M. (1994) J. Biol. Chem. 269, 14857–14860; and Wawabata, H., Anzai N., et al (1997) Biochem. Biophys. Res. Commun. 233, 133–138). However, any reports on the endonuclease involving apoptosis published so far have not yet taught that $Mg^{2+}$-dependent endonuclease was identifed as protein band or enzyme activity band.

In aspects of calcium dependence, mobility distance in native-PAGE and optimum pH, the endonuclease identified by the inventors is distinct from enzymes involving internucleosomal fragementation of DNA reported so far, for example, $Ca^{2+}/Mg^{2+}$-dependent endonuclease (Stratling W. H. et al (1984) J. Biol. Chem. 259,5893–5898; Pandey S. et al (1997) Biochemistry 36, 711–720; and Ribeiro J. M., and Carson D. A.(1993) Biochemistry 32, 9129–9136), DNase I (Peitsch M. C., et al (1993) EMBO J. 12, 371–377), DNase II (Torriglia A. et al (1995) J. Biol. Chem. 270, 28579–28585; and Barry M. A., and Eastman A. (1993) Arch. Biochem. Biophys. 300, 440–450) and NUC-18 (Kawabata, H. et al (1997) Biochem. Biophys Res. Commun. 233,133–138). Since the endonuclease of the present invention is observed in cellular nucleus during apoptosis process, it is believed that the endonuclease takes an important role in the apoptosis process.

2-1 Induction of Apoptosis

Human B-lymphoblastic(IM9) cells were cultured and then apoptosis was induced by treating the cells with 10 ug/ml CHX(Sigma) and then culturing them for 24 hours (Chow, S. C. et at (1995) Exp. Cell. Res. 216, 149–159). A changed cell shape of the apoptosis cells induced by CHX was identified by staining the cells with Wright-Giemsa (Sigma) on centrifuge slide.

Figure 15:
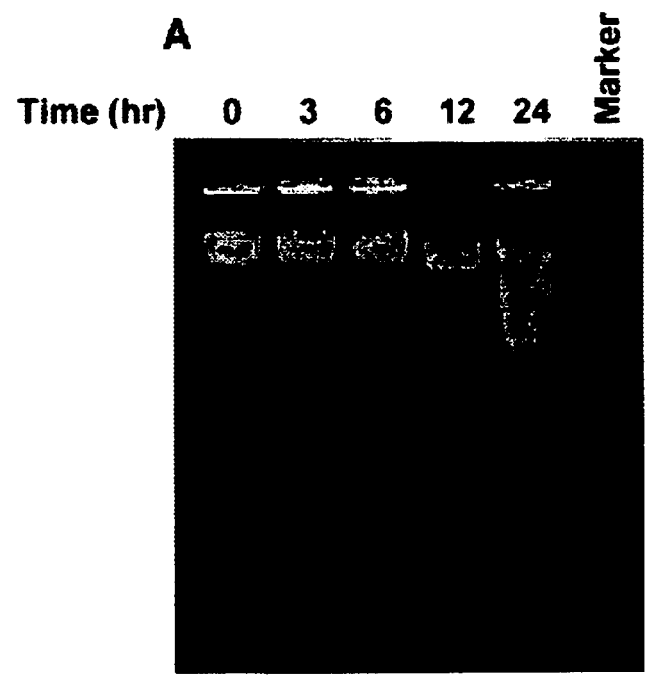
FIG. 15 shows the apoptotic cell death of IM9 cells by CHX treatment (A, 1.8% agarose gel electrophoreis of DNA from IM9 cells treated with CHX (10/ml); Untreated (B) and treated (C) with CHX of IM9 cells were cultured for 24 hr and cytocentrifuge preparations stained with Wright-Giemsa).
Figure 15:
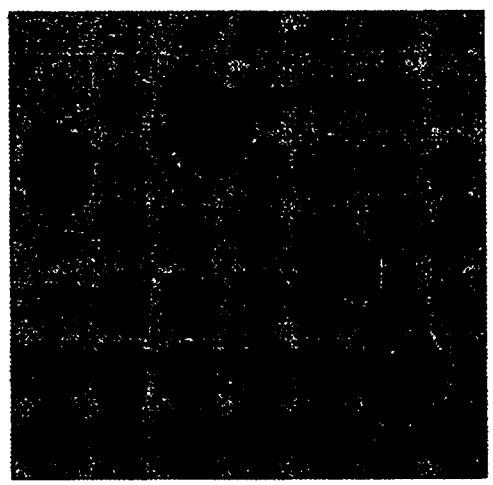
Figure 15:
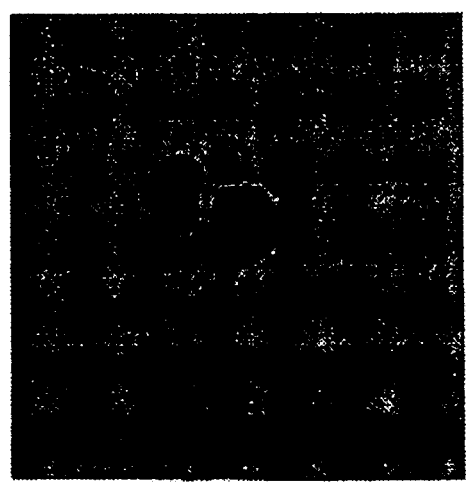

FIG. 15A shows that the treatment of IM9 cells with CHX(10/ml) for 24 hours provides the DNA fragments as a characteristic form of internucleosomal DNA digestion. After 24 hours, the effect of CHX was exhibited and after further 24 hours large amount of DNA fragments were formed. The cell was stained with Wright-Giemsa dye to observe the cell shape during the cell death caused by apoptosis. The result is shown in FIG. 15C. Many apoptosis cells were generated by CHX treatment, and the cell shape characterized by distortion, chromosomes aggregation and nuclei fragmentation was distinct from that of normally growing cells.

2-2Identification of DNA Fragmentation by end Endonuclease of IM9 Cells Treated with CHX IM9 cell lines were cultured to $5 \times 10^5$ cells/ml and treated with 10 ug/ml CHX (Sigma). While culture was performed for 24 hours, $1 \times 10^6$ cells were collected at regular intervals and then DNA was extracted according to modified method of Blin and Stafford (Blin, N., and Stafford, D. W. (1976) Nucleic Acids Res 3, 2303–2308. $1 \times 10^6$ cells were washed two times with PBS and resuspended in TE buffer solution. After adding 1 ml of DNA extraction buffer solution (10 mM Tris-HCl, pH 7.6, 10 mM EDTA, 100 mM NaCl, 0.2% SDS and 100 ug/ml proteinase K), the reaction mixture was reacted at 50° for 8 hours and treated twice with phenol/chloroform to remove protein. After adding 0.3M sodium acetate(pH 5.2), the reaction mixture was precipitated with cold ethanol. The precipitate was dissolved in TE(10 mM Tris-HCl, pH 7.6, 1 mM EDTA) buffer solution and treated with RNase A. Then an electrophoresis was carried out on 1.8% agarose gel. The electrophoresis gel was placed in the solution containing 0.5 ug/ml ethidium bromide for 30 minutes and photographed under UV.

Figure 16:
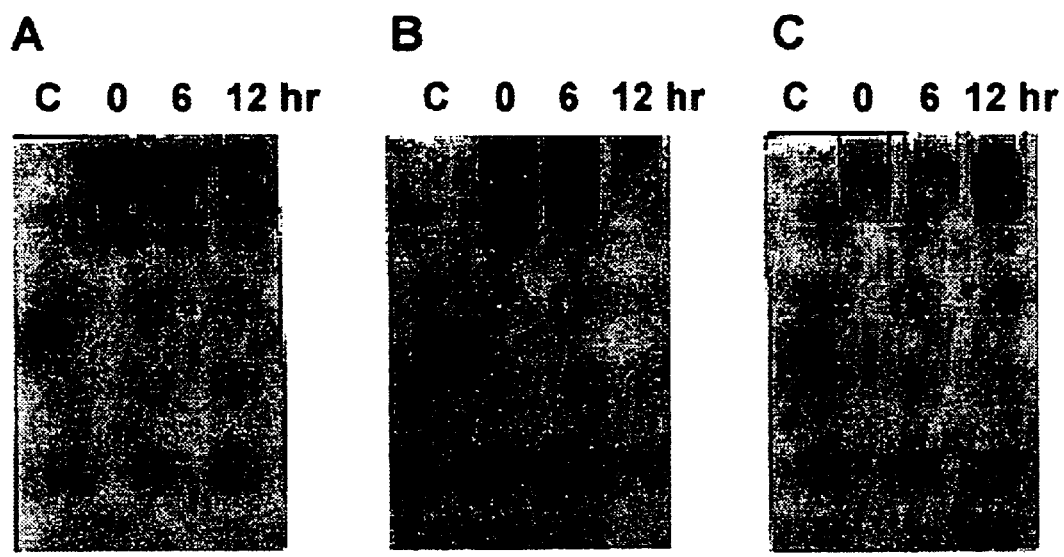
FIG. 16 shows the endonuclease activity of IM9 cell lysates and nuclei analyzed by DNA-native-PAGE according to the present invention. The endonuclease activity was detected in IM9 cell lysates during culture time (A), cell lysates (B) and nuclei (C) treated with 10 ug/ml CHX for the indicated times. Control: FBS DNase 1.

IM9 cells treated with CHX were collected at regular intervals and cell lysate and nuclei were prepared. After the cell lysate and nuclei were dissolved, a gel assay of DNA-native-PAGE nuclease activity was performed to identify the enzyme activity of the endonuclease present in nucleus. FIG. 16A shows that when IM9 cells were cultured for 24 hours, the enzyme activity of the endonuclease was constantly detected in cell lysate over the period. However, the enzyme activity in the cell lysate treated by CHX was reduced for 6 to 12 hours (FIG. 16B), whereas the enzyme activity in the nucleus was accumulated (FIG. 16C).

2-3 Isolation of Cell Nucleus and Autolysis $1 \times 10^7$ cells was washed three times with cold PBS and dissolved in 0.5 ml cold buffer solution comprising 50 ml Tris-HCl pH8.0, 5mM $MgCl_2$ and 0.9 M sucrose at 40° C. for 20 minutes to isolate nucleus of cells. The prepared cell lysate was placed in 0.5 ml of 1.2 M sucrose solution and centrifuged at 800 g for 40 minutes. The resulting precipitate was suspended in 20 mM Tris-HCl, pH 7.0, buffer solution to obtain nuclei.

Autolysis of the isolated nucleus was carried out by changing the concentration of $Mg^{2-}$ and $Ca^{2-}$ at 37° C. at regular intervals. The reaction was stopped by adding 0.5 ml DNA extraction buffer solution comprising 10 mM Tris-HCl, pH 7.5, 100 ml NaCl, 1 mM EDTA, 1% SDS proteinase K. The mixture was reacted at 50° C. for 30 minutes, treated twice with phenol/chloroform to remove proteins. After adding 0.3M sodium acetate, pH 5.2, the mixture was precipitated with cold ethanol. After dissolving the precipitate in TE buffer solution, the solution was treated with RNase A. Then, electrophorosis was carried out on 1.8% agarose gel. The electrophoresis gel was placed in a solution containing 0.5/ml ethidium bromide and photographed under UV.

Figure 14:
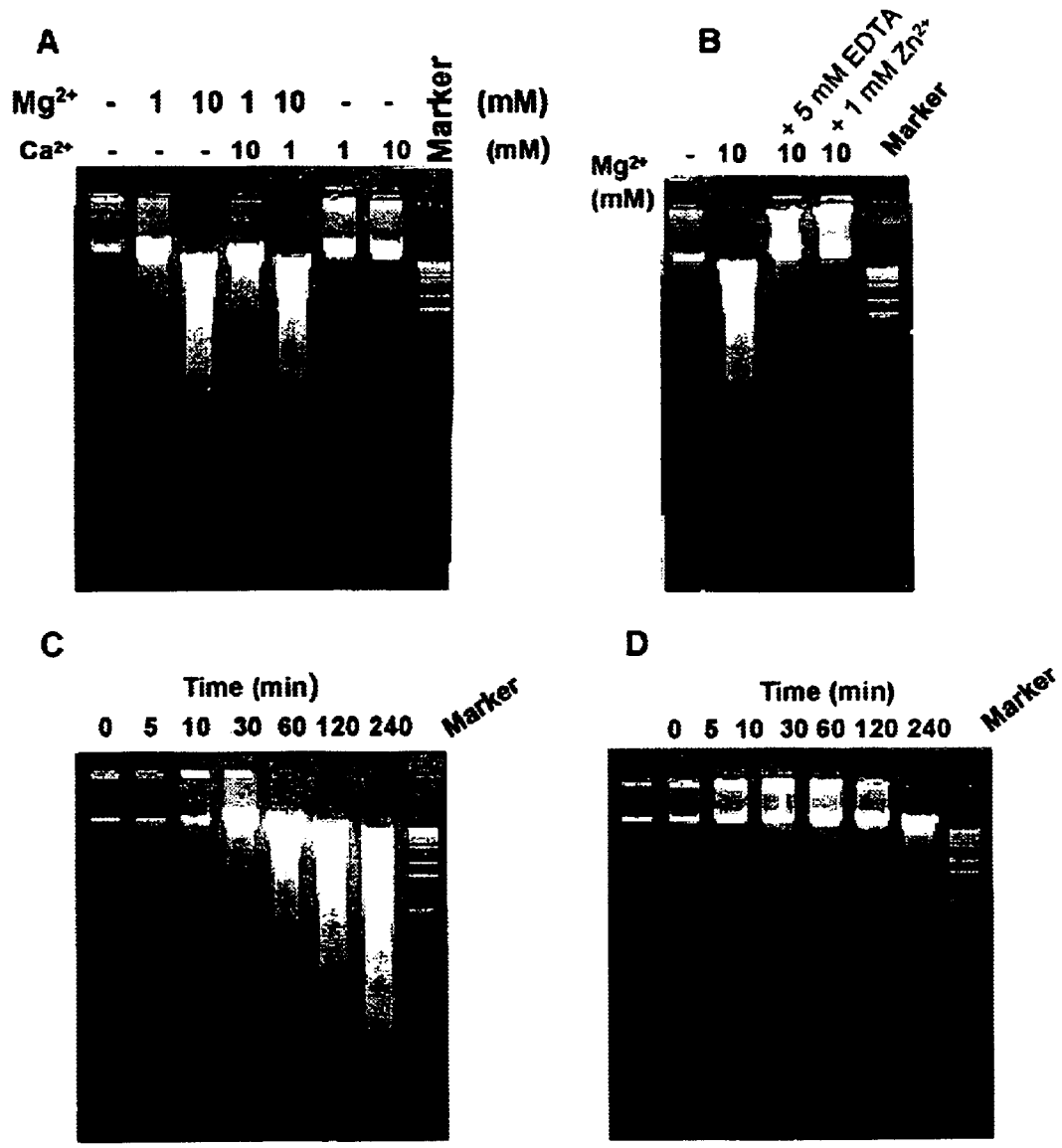
FIG. 14 shows the endonuclease activity in nuclei isolated from IM9 cells by autodigestion method (A, Nuclei were incubated for 2 hr at 37° C. either alone or on the presence of the indicated concentration of $Ca^{2+}$ and/or $Mg^{2+}$; B, Inhibition of internucleosomal DNA fragmentation; C and D, Nuclei were incubated at 37° C. in the presence of 10 mM $Mg^{2+}$ (C) or 10 mM $Ca^{2+}$ (D) for 0–240 min as indicated; and Marker, 1 kb ladder)

By using autolysis method of the isolated cell nuclei, the enzyme activity of the enconuclease present in the nucleus of IM9 cell was determined to observe the phenomenon in which DNA fragments are produced depending on the $Mg^{2+}$ concentration. However, when under the same experiment condition $M^{2+}$ was replaced with $Ca^{2+}$, such DNA fragmentation was not observed. In the presence of both of $Ca^{2+}$ and $Mg^{2+}$, DNA fragments were produced as the same type as in the presence of $Mg^{2-}$ only. The result indicates that DNA is digested by the eudonuclease depending on the concentration of $Mg^{2+}$. In the presence of 1 mM $Zn^{2-}$ and 5 mM EDTA, DNA fragments were not produced in nucleus (FIG. 14B). DNA fragmentation was carried out at the constant concentration of $Mg^{230}$ (10 mM) and $Ca^{2+}$ (10 mM) for 0–4 hours. As results, 30 minutes after the reaction was initiated in the presence of $Mg^{2-}$ alone, the DNA fragments was produced, and at 60 to 240 minutes, the DNA fragments were accumulated (FIG. 14C). But, in the presence of $Ca^{2+}$, the formation of DNA fragments was not observed for 4 hours (FIG. 14D). These results indicate that $Mg^{2-}$ is required for the endonuclease activity present on the nucleus of IM9 cell to form DNA fragments.

2-4 Partial Purification of Endonuclease Present on the Nucleus of Cells and Characterization The endonuclease present in the nucleus of cells was partially purified by dissolving the nucleus and eluting the protein band exhibiting the endonuclease activity as described in the above Examples 1–4. The enzyme activity was measured by using the supercoiled plasmid DNA as a substrate and the divalent ion dependence was observed according to the above Examples 1–4. Also, the change of enzyme activity by treatment of $ZnCl_2$, apoptosis-inhibiting substance, and EDTA, chelating agent was observed.

Figure 17:
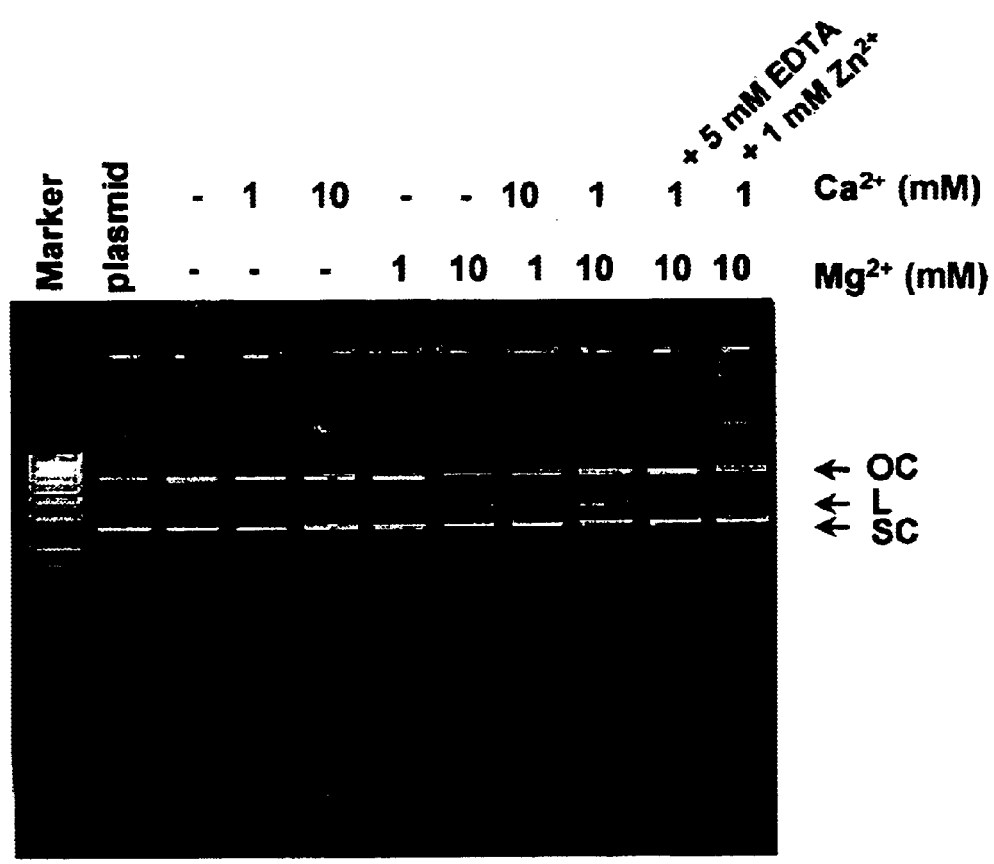
FIG. 17 shows the requirement of divalent cation for the endonuclease activity according the present invention. The endonuclease was isolated from nuclei and the enzyme activity was determined by resolving the reaction products on 1% agarose gel.

The enzyme was isolated and eluted by native-PAGE to characterize the enzyme activity of endonuclease present in the nucleus of IM9 cell which was identified by DNA-native-PAGE. The observation revealed that the endonuclease is $Mg^{2-}$-dependent (FIG. 17). The endonuclease activity was completely inhibited by $Zn^{2-}$, apoptosis-inhibiting substance, and EDTA, chelating agent. The results indicate that $Mg^{2+}$ is required to convert the supercoiled plasmid DNA into the linear DNA and is consistent with the result shown in FIG. 8.

EXAMPLE 3

Action of Endonuclease to Foreign DNA in Immune Cell and Characterization of the Reaction Product.

It was known that bacterial DNAs so far recognized as foreign agent include various structure-determining factors which are not present in mammalian DNA and that such factors are involved in the activation of immune cell (Gilkeson, G. S. et al (1995) J. Clin. Invest. 95, 1398–1402; Gilkeson. G. S. et al (1991) Clin. Immunol, Immunopathol. 59, 288–300; Messina, J. P. et al (1993) Cell. Immunol. 147, 148–157; Krieg, A. M. et al (1995) Nature 374, 546–549; and Halpern, M. D. et al (1996) Cell. Immunol. 167, 72–78 ). One of the differences of mammalian DNA from bacterial DNA is that the mammalian DNA was subject to considerable CpG restriction and was selectively methylated on cytosine of CpG dinucleotide (Bird, A. P. (1995) Trends Genet. 11, 94–100; Razin, A., and Friedman, J. (1981) Prog. Nucleic Acid Res. Mol. Biol. 25, 33–52; and Han, J. et al (1994) Antisense Res. Dev. 4, 53–65). Recent reports show that CpG motif present in bacterial DNA activates polyclonal B cell to promote secretion of IgM (Krieg, A. M. et al (1995) Nature 374, 546–549; Liang, H. et al (1996) j. Clin. Invest. 98, 1119–1129; and Yi, A.-K., et al (1996) J. Immunol. 156, 558–564) and suggest that cell cycle is stopped by anti-IgM antibody and bacterial CpG motif inhibits the expression of c-myc of B cell while increasing the expression of myn, $blc_2$ and bcl-$X_L$ mRNA to protect the cell from apoptosis (Y, A. K. et al (1996) J. Immunol. 157, 4918–4925). Halpern reported that CpG motif directly activates B cell to promote secretion of IL-6 and IL-12 for short period (Halpern, M. D. et al (1996) Cell. Immunol. 167, 72–78; Yi. A.-K. et al (1996) J. Immunol. 157, 5394–5402; and Klinman, D. M. et al (1996) Proc. Natl. Acad. Sci. USA 93, 2879–2883). Bird showed that CpG motif weakly act for NK cell to induce IFN-γ from $CD4^4$ (Bird, A. P. (1995) Trends Genet. 11, 94–100; ald Yamamoto, S. et al (1992) Microbiol. Immunol. 36, 983–997). Accordingly, the activation of immune cell by CpG DNA increases humoral immunity by IL6 and increases cellular immunity by IFN-γ secretion. It was known that bacterial DNA is digested by macrophage and then the macrophage is activated to produce TNF-α, IL-1β and plasminogen activator inhibitor-2 mRNA (Stacey, K. J. et al (1996) J. Immunol. 157, 2116–2122)

3-1 Bacteria DNA Processing by Endonuclease

The culture solution of IM9 cell was used as enzyme source to analyse the specificity of the enzyme activity of the endonuclease and the property of the final reaction product IM9 cells were cultured in RPMI 1640 medium containing 10% FBS in 5% $CO_2$ incubator at 37° C. for 48 hours and then the culture solution was used as enzyme source. Also, the culture solution obtained by culturing the cells in FBS-free medium for 36 hours was used as enzyme source including only endonucleases secreted by IN9 cell without DNase I.

The plasmids (pGEM-T vector, 3.0 Kb) used as the substrate of ene were obtained by disrupting the E. coli by the alkaline lysis method (Birboim, H. C., and Doly, J.(1979) Nucleic Acids Res. 7, 1513–1523), followed by extracting twice with phenol/chloroform and precipitating with ethanol. Genomic DNA of E. coli and DNA of IM9 cell were extracted by the modified method of Blin and Stafford. Cells were twice washed with PBS and was floated by TE buffer solution. DNA extraction buffer solution (10 mM Tris-HCl, pH7.6, 10 mM EDTA, 50 mM NaCl, 0.2% SDS, 20 ug/ml Rnase A) was added and the solution was stood at 37° C. for 10 minutes. Proteinase K was added to 100 ug/ml and the mixture solution was reacted at 50° C. for 8 hours. The reaction solution was extracted three times with phenol/chloroform to remove protein and ethanol precipitation reaction was carried out to genomic DNA. Salmon sperm DNA was also extracted and used as described above. The amount of LPS present in DNA was measured by Limulus amebocyte lysate assay (Sullivan, J. D. et al (1976) in Mechanisms in Bacterial Toxicity, A. W. Bernheimer, ed. Wiley, New York, p. 217) and was 2.5 ng/ml or less.

To compare the enzyme activity in IM9 cells cultured on the medium containing 10% FBS and the FBS-free medium, 100 ng of plasmid DNA was mixed with 20 ul of each culture and reacted at 37° C. at regular intervals. In the assay of enzyme activity of enconuclease by using the cell culture, the cell culture on the FBS-free medium was used in order to eliminate the effects of DNase I present in FBS. Also, 100 ng of each of genomic DNAs of E. coli, IM9 cell and salmon sperm was reacted under the same condition as described above and thus the enzyme activity was determined on 1% agarose gel electrophoresis.

Figure 18:
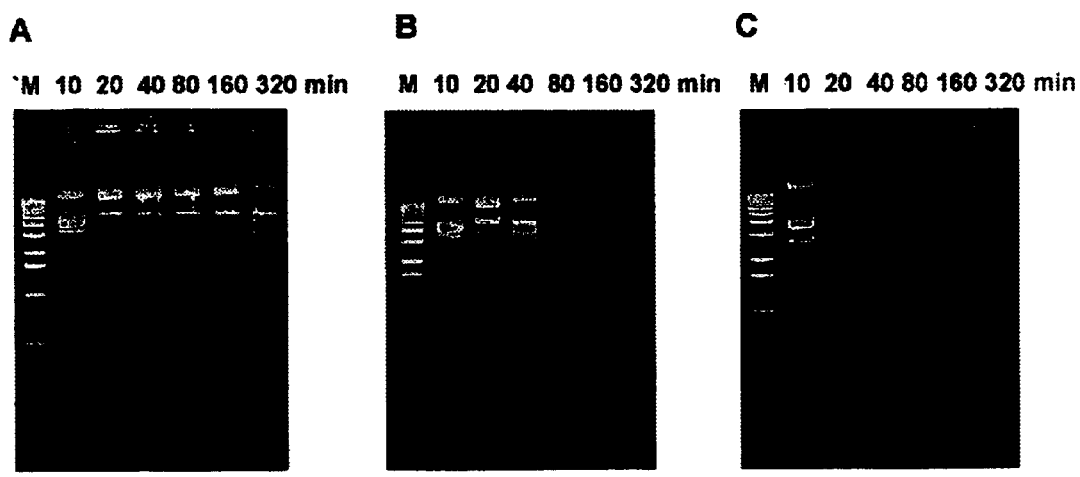
FIG. 18 shows the time-course degradation of plasmid DNA by the endonuclease of the present invention. The endonuclease activity of RPMI medium containing 10% FBS (A), IM9 cell culture medium in serum free (B), and IM9 cell culture containing 10% FBS (C) was estimated by resolving the reaction products on 1% agarose gel.
Figure 19:
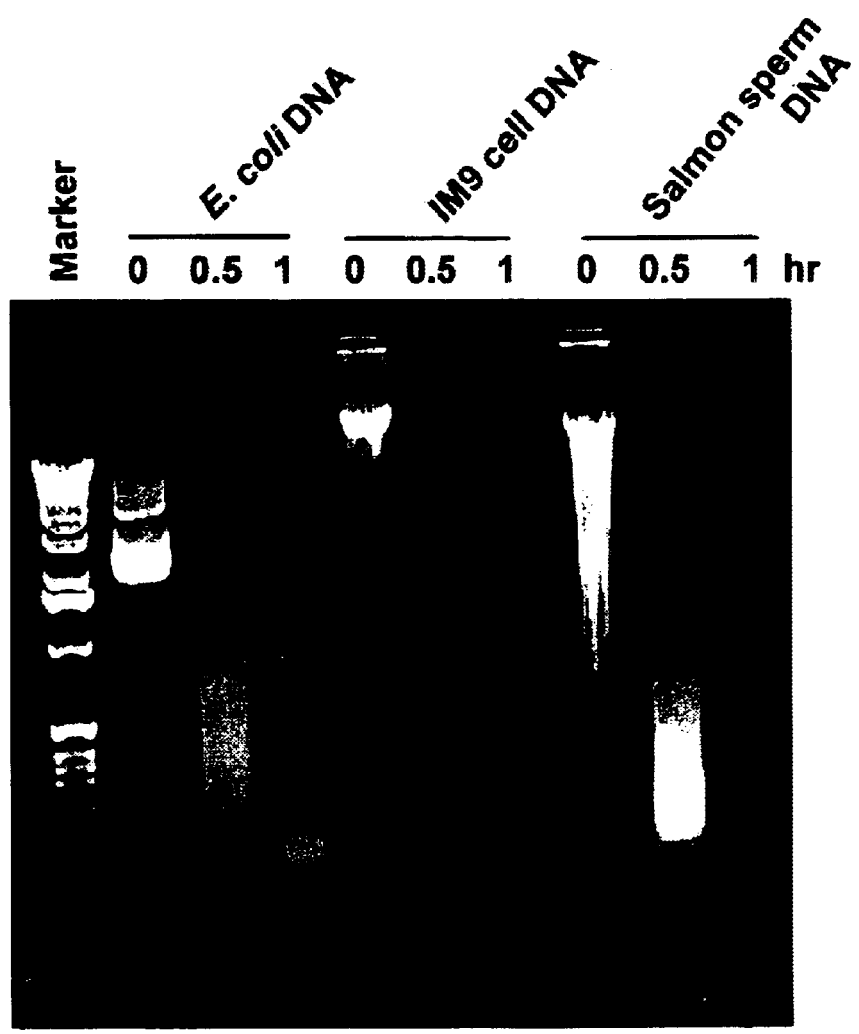
FIG. 19 shows the products of endonuclease reaction of the present invention on E. coli DNA, IM9 cells DNA, and salmon sperm DNA.

RPMI1640 median containing 10% FBS and IM9 cell culture was directely reacted with bacterial DNA to observe the digestion degree of bacteria DNA in vitro. FIG. 18A shows the digestion degree of plasmid DNA in RPMI1640 medium containing 10% FBS. Unlike the results shown in FIG. 1D, the result showed that despite DNase I was present in the medium, the weak enzyme activity was detected. This indicates that the medium includes ions or inhibitors which can effect on DNase I activity. However, plasmid DNA was degraded by FBS-free cell culture solution or 10% FBS-containing cell culture solution (FIGS. 18B and 18C). This indicates that plasmid DNA was degraded by the endonuclease secreted by IM9 cell line. The comparison of FIG. 18B and FIG. 18C shows that the enzyme activity in 10% FBS-containing cell culture solution is higher. In the case where cell culture was initiated at $2\times10^5$ cells/ml, cell growth in the presence of FBS was actively taken placed and a great quantity of endonuclease was secreted FIG. 19 shows that all of E. coli DNA, IM9 cell DNA and salmon sperm DNA was degraded by endonuclease.

3.2 Incorporation of Bacterial DNA into Cells and Analysis of the DNA Base Sequence IM9 cell line was cultured on a 1:1 mixed medium of RPMI1640 medium containing heated 10% FBS and IM9 cell culture solution which was cultured for 48 hours. The bacterial DNA (25 ug/ml) was added to the culture solution. While the IM9 cell line was cultured in cell density of $1\times10^6$ cells/ml, the cells were collected at regular intervals and were used to extract the DNAs incorporated into the cells.

After IM9 cell line was treated with the bacterial DNA, the cells were collected at regular intervals and washed three times with PBS. The cells were resuspended in a cold lysis buffer (10 mM Tris-HCl, pH 7.5, 1 mM EDTA, 150 mM NaCl, 1 mM PMSF, and 0.5% NP-40), and the cell lysates were obtained by the method described in the above Example 1–2. The same volume of DNA extraction buffer was added to the cell lysates and placed at 42° C. for 3 hours and then treated twice with phenol/chloroform to remove protein. Then the DNA present in the cell lysates was extracted by ethanol precipitation. The precipitate was dissolved in TE buffer and treated with RNase A and used for a sample of southern blotting.

The DNA extracted from the cell lysates was separated by electrophoresis on a 1.8% agarose gel and southern transfer was carried out. After electrophoresis, the agarose gel was shaken for 20 minutes in about 200 ml of alkaline solution (1.5 M NaCl and 0.5 M NaOH), washed with distilled water, and placed for 20 minutes in about 200 ml of the neutralization solution (1.5 M NaCl, 0.5 M Tris-HCl, pH 7.5). Subsequently, the agarose gel was shaken in a fresh neutralization solution. 175.3 g of NaCl, 88.2 g of sodium citrate and 2 ml of 0.5 M EDTA were added to distilled we to make 11 solution and the resulting solution was autoclaved at 121° C. to obtain SSC solution. One rectangular vessel A was reversely placed on another vessel B containing 20×SSC so that the bottom of the vessel A could be positioned on the surface of the solution contained in the vessel B. Whatman No. 3 paper with a width of 2 mm, saturated with 20×SSC, was placed on the bottom of the vessel A without any air bubbles so that both 20×SSC could be connected. The agarose gel was reversely placed on the paper, and Hybond$^+$ nylon membrane was placed on the agarose gel to prevent air bubbles from being generated. Three Whatman No. 3 papers, smaller than the agarose gel in four facets by 2 mm each, were placed on the Hybond$^+$ nylon membrane with no air bubbles. Then, paper towels were piled to reach the height of 10 to 20 cm and were weighed down with about 500 g. The bottom around the gel was surrounded with parafilm and the capillary transfer was run for 8 hours. The membrane carrying the DNA was exposed to UV radiation of 120,000 uJ/cm for 2 minutes to be crosslinked by UV.

The bacterial DNA was reacted with the endonuclease at 37° C. for 30 minutes and 100 to 200 bp of the resulting product was electrophoresed on 1% agarose gel. Using the Gene Clean Kit (Promega Inc.), the DNA was recovered from the gel and was used as a DNA probe. 50 to 100 ng of the DNA was heated to 100° C. in water for 3 minutes, and cooled rapidly on ice to separate the DNA fragments and then labeled with $^{32}$P. DNA labeling reaction was conducted according to the random priming method in which 20 ul of a mixture consisting of 10 ng of random primer, 4 ul of buffer solution (50 mM Tris-HCl, pH 80,5 mM MgCl$_2$, 2 mM DTT, 0.5 mM HEPES, pH 6.6), 25 uM dATP, 25 uM dGTP, 25 uM dTTP, 60 uCi [$\alpha$-$^{32}$P]dCTP, and 5 ul of Klenow enzyme was reacted at 37° C. for 2 hours. 2 ul of 0.5 M EDTA was added to the reaction mixture to terminate the reaction, and then the same volume of 3 M sodium acetate, pH 5.2, and 20 ug of salmon sperm DNA were added. A double volume of ethanol was added to the reaction mixture to precipitate the desired DNA. The precipitate was dissolved in TE buffer, heated at 100° C., and cooled rapidly on ice.

UV-crosslinked Hybond$^+$nylon membrane was added to a prehybridization solution (6×SSC, 5×Denhardt's solution, 0.05% sodium pyrophosphate, 0.5% SDS, and 100 ug/ml of salmon sperm DNA) prebathed at 68° C., and shaken at 68° C. for at least 1 hour. The labeled probe, prepared by the random priming method and cooled on ice, was added to be hybridized for about 12 hours. The filter was transferred to the washing solution I (2×SSC, 0.1% SDS) and washed for about 10 minutes at ambient temperature. The filter was then transferred to the washing solution I prebathed at 68° C., and shaken and washed about 25 minutes. Subsequently, the filter was transferred to the washing solution II (0.2×SSC, 0.1% SDS) prebathed at 68° C. and washed while the radioactivity of the filter was measured by Geiger counter. The filter was inserted to a cassette fit with intensifying screen and X-ray film. After 12 to 24 hours at −70° C. the filter was developed.

Figure 21:
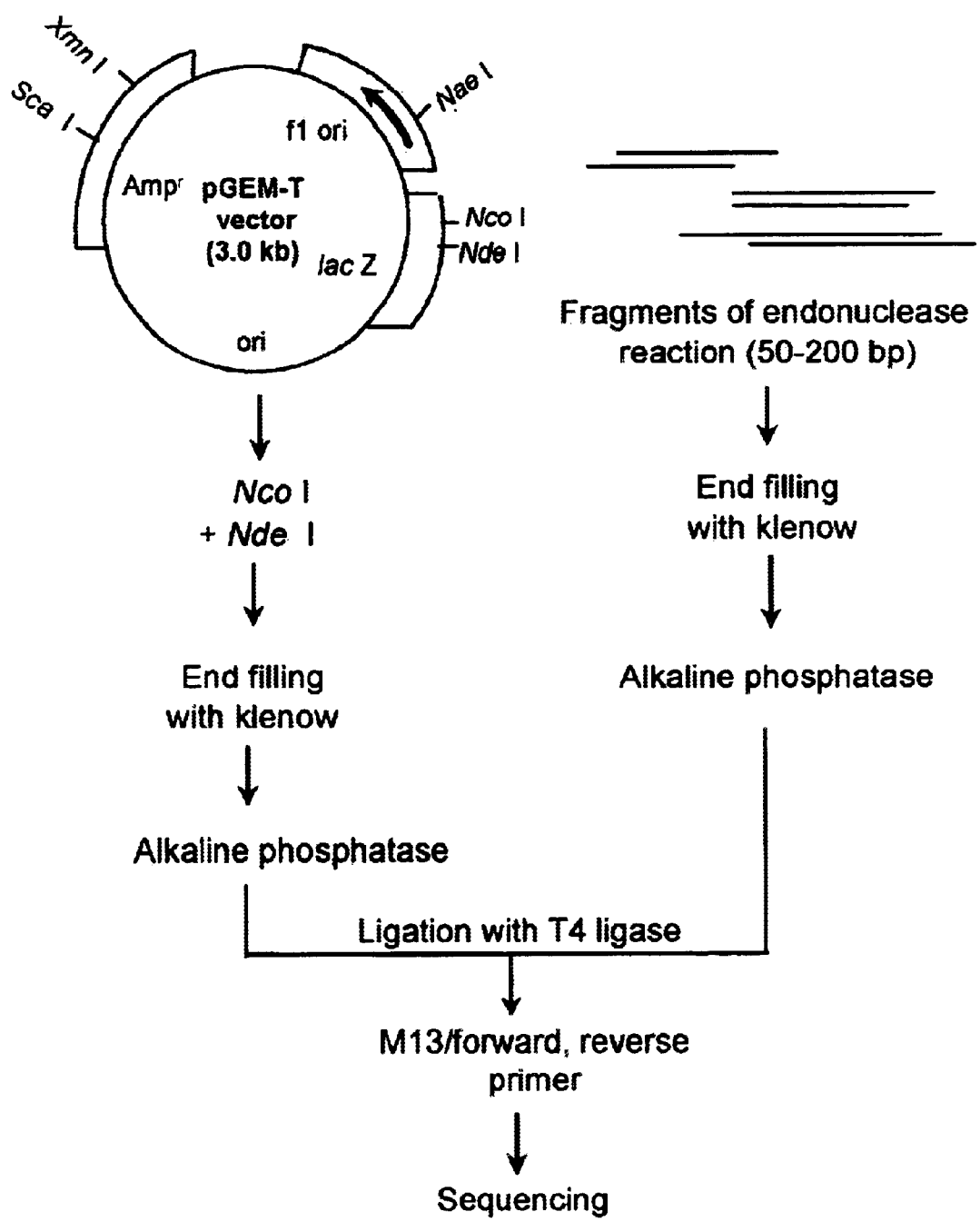
FIG. 21 shows the construction scheme for the cloning and sequencing of the DNA fragments obtained by endonuclease reaction according to the present invention

The bacterial DNA or the plasmid DNA were added during cell culture, and incubated for 1 hour at 37° C. The DNA fragments present in the cell lysates were electrophoresed on a 1.8% agarose gel. Then, the gel of 50–200 bp sites by southern transfer was recovered using Gene Clean Kit (Promega Inc.). The DNA fragments were introduced into the pGEM-T vector (Promega Inc.) as shown in FIG. 21 to identify base sequences. The resulting vector was cloned in E. coli and analyzed by a SEQUENASE™ version 2.0 DNA sequencing kit (USB), according to the Sanger dideoxyribonucleotide chain termination method (Sanger, F. et al. (1977) Proc. Natl. Acad. Sci. USA 74, 5463–5467). MB forward/reverse primer described in Table 1 below was used as the primer for sequencing. Cloned DNA sequence was confirmed as bacterial or plasmid DNA fragments by a BLAST (Basic Local Alignment Search Tools) program.

TABLE I

| oligonucleotides | | using |
|---|---|---|
| A TTAAAACGTTCAC | (SEQ ID NO: 1) | CpG motif |
| B AAGTGAACGTTTT | (SEQ ID NO: 2) | CpG motif |
| C AGCAGCGCTAA | (SEQ ID NO: 3) | CpG motif |
| D AATTAGCGCTG | (SEQ ID NO: 4) | CpG motif |
| E CTCCCGGCCGCCATG | (SEQ ID NO: 5) | PCR primer |
| F TTGGGAGCTCTCCC | (SEQ ID NO: 6) | PCR primer |
| G GTTTTCCCAGTCACGAC | (SEQ ID NO: 7) | sequencing (pUC/M13 forward) |
| H CAGGAAACAGCTATGAC | (SEQ ID NO: 8) | sequencing (pUC/M13 reverse) |

Figure 20:
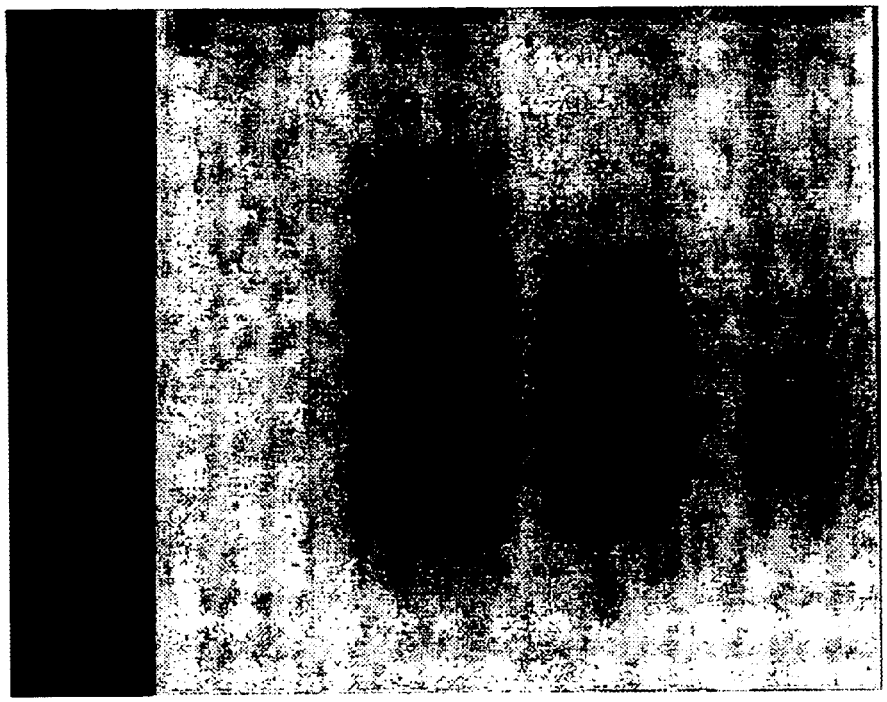
FIG. 20 shows the southern blot analysis of foreign DNA incorporated into IM9 cells. 100–200 bp fragments of endonuclease reaction products were used as a probe. Blot were hybridized for 6 hr at 55° C. with probe prepared by the random-priming method.

The test results show that when 25 ug/ml of bacterial DNA was incubated with IM9 cell, the DNA was properly processed in the cell culture and incorporated into the cells. This was confirmed by southern hybridization (FIG. 20). The presence of 100–200 bp DNA was found 30 minutes after the cell culture. The amount of 100–200 bp DNA in the cells was decreased with the lapse of the culture time. The results suggest that properly processed DNA was incorporated into IM9 cell line and the processing was continued in cells.

To identify the property of the product obtained by the enzyme activity of the endonuclease, the bacterial DNA incorporated into cells was isolated and its DNA sequence was analyzed as shown in FIG. 21. As shown in Table 2, the reaction product of the endonuclease had a characteristic base sequence, i.e., CpG motif carrying two purine bases at 5' end and two pyrimidine bases at 3' end. It is known that CpG motif activates B cell or macrophage in an immune system and promotes The secretion of cytosine and IgM and is present in bacterial DNA at high frequency. Accordingly, it was now found that the endonuclease present in IM9 cell culture solution and the DNA processing by the enzyme activity in the cell generate CpG motif which functions to activate immune cells.

TABLE 2

50–200 bp DNA fragments produced by endonuclease reaction in cell

| | Sequence | | Precursor |
|---|---|---|---|
| EC1 | ..AGAGCAGCGCTAATGTCTATCGATGATTT..<br>..GTCAAAACGTTCACCA... | (SEQ ID NO: 9)<br>(SEQ ID NO: 10) | E. coli from bases 2874223 to 2885334 of the complete genome (5416–5614) |
| EC2 | ..TTAACAACGTTGGGGCGATTGAGAGCGAT<br>GGCGTTGATTTCATGTAAACGAAGCTAACGTG<br>GTGAAAACGATGATGGCGCACGCGAGAAAT... | (SEQ ID NO: 11) | E. coli from bases 4067762–4083201 of the complete genome (4741–4852) |
| EC3 | ...CCCATGACGCACCGCA......<br>.ATTCCATCGCCATCTCAAACTTCGGTAA | (SEQ ID NO: 12)<br>(SEQ ID NO: 13) | E. coli from bases 2244905 to 2255428 of the complete genome (2027–2108) |
| EC4 | TGCCTCGGAGTTACCTAATTCCATCGCCA<br>TCTCAAACTTCGGTAAA | (SEQ ID NO: 14) | E. coli from bases 2244905 to 2255428 of the complete genome (2064–2109) |
| EC5 | ..CCTTTGACGTTGAGTCCACGTTCTTTA...<br>..CCTATCTCGGTCTATT.. | (SEQ ID NO: 15)<br>(SEQ ID NO: 16) | E. coli plasmid synthetic cloning vector pET31F (268 376) |
| EC6 | TTTACGGTTCCTG....<br>..TTTCCTGCGTTATCCC... | (SEQ ID NO: 17)<br>(SEQ ID NO: 18) | Plasmid pKF3 from E. coli (2004–2066) |
| EC7 | GTCGACCATATGGGAGAGCTCC.....<br>ACGCGTTGGATG..<br>AGCTTGGCGTAATCAT | (SEQ ID NO: 19)<br>(SEQ ID NO: 20)<br>(SEQ ID NO: 21) | Cloning vector pGEM-5Zf(-) (75–170) |
| EC8 | ...TTTCCTGCGTTATCCC...<br>..GCTGATACGCTCGCCGCAGCCGAACG<br>ACCGAGCGCAGCGAGTCAGTGAGCGAGG<br>AAGCG | (SEQ ID NO: 22)<br>(SEQ ID NO: 23) | Sequence from U.S. Pat. No. 4,921,698 |
| PD1 | CTTCCTCGCTCACTGACTCGCTGCGCTCG<br>GTCGTTCGGCTGCGGCGACGGTATCAG... | (SEQ ID NO: 24) | pGEM-T vector (401–519) |
| PD2 | .....GGTCTGACGCTCAGTGGAACGA<br>AAACTCACGTTAAGGG......... | (SEQ ID NO: 25) | pGEM-T vector (1130–1306) |
| PD3 | ....TAAAGAACGTGGACTCCAA<br>CGTCAAAGGGCGAAAAACCGTCTAT<br>CAGGGCGATGGCCC.... | (SEQ ID NO: 26) | pGEM-T vector (2513–2610) |

TABLE 2-continued

50–200 bp DNA fragments produced by endonuclease reaction in cell

| Sequence | | Precursor |
|---|---|---|
| PD4 | ...TTCCCAA<u>CG</u>ATCAAGG<u>CG</u>AGTTACA.. CTC<u>CG</u>AT<u>CG</u>TTGTCAG...... (SEQ ID NO: 27) (SEQ ID NO: 28) | pGEM-T vector (1685–1795) |
| EC9 | ..TGCTGTT<u>CG</u>GCACCAACAAT<u>CA</u>CGCC GACTTTAA.............. (SEQ ID NO: 29) | *E. coli* from bases 220025 to 231029 of the complete genome (829–872) |
| HC1 | ...TTCGATTCGAT..... (SEQ ID NO: 30) | *Homo sapiens* satellite 2 repetitive element DNA |

3-3 Confirmation on the Processing of DNA Incorporated into Cells

To confirm as to how far the cloned DNA fragments of 50–200 bp incorporated into cell by processing are further processed within cells and how the base sequences of the DNA fragments influence on the cells, a PCR amplification was performed. The PCR reactive solution contained 0.2 mM dNTP, 10 pmole of primer, 10 mM Tris-HCl, pH 8.3, 50 mM Kcl, 1.5 mM $MgCl_2$, and 2.5 units of Taq polymerase. 5'-CTCCCGGCCGCCATG-3' (SEQ ID NO: 5) and 5'-TTGGGAGCTCTCC-3' (SEQ ID NO: 6) (Table I) were synthesized and used as a PCR primer. The PCR reaction was repeated 35 times under the following condition: denaturation (at 94° C. for 30 sec.); primer annealing (at 42° C. for 30 sec.); primer extension (at 72° C. for 50 sec.). The PCR product was run on 8% native-PAGE in a TBE buffer solution and was stained with ethidium bromide. Subsequently, DNA was separated from the gel of the PCR reaction product. The separated DNA was precipitated by ethanol, and was dissolved in PBS for cell culture or was dissolved in TE buffer solution for the detection of the activity of the endonuclease.

To confirm as to which form of the end product exists after the product obtained by the PCR amplification in a vector cloning 100–200 bp of bacteria DNA, which was cut by the activity of the endonucleotide, is introduced into cells, the EC1, EC2, and HC1 DNA fragments were labeled with $^{32}P$ by a random-priming method using random primer and Klenow enzyme. 100 ng/ml of the DNA fragments labeled with $^{32}P$ were incorporated into IG9 cell line, U937cell line, and U937 cell line treated with TPA. Whether DNA was incorporated into cells was confirmed at regular intervals. The endonuclease was treated with 0.2 mM, $ZnSO_4$ (Sigma) to terminate its enzyme activity. The DNA incorporated into cells was recovered in a cell lysate and run on 20% native-PAGE in the TBE buffer solution. The gel was dried and autoradiographed to confirm the processing of DNA within cells and the end product obtained by the endonuclease reaction.

The EC1 DNA fragment labeled with $^{32}P$ was incorporated into IM9 cell line. The DNA incorporated into cells were extracted from cell lysates and 20% native-PAGE was carried out. The processed DNA labeled with $^{32}P$ was extracted from the gel and annealed with a various synthesized oligonucleotides to compare their base sequences with each another. A predetermined amount of the extracted DNA labeled with $^{32}P$ and 10 ng of each of oligonucleotides were mixed with 6×SSC. The mixture was boiled at a temperature of 100° C. for 5 minutes, and annealed at temperatures lowered by 1° C. per 30 seconds. The annealed reactant was run on 20% natural-PAGE at 4° C., and an autoradiography for the reactant was carried out. Thus, oligonucleotides complimentarily conjugated to the DNA incorporated into cells were confirmed. As standards, a mixture of DNA and oligonucleotides which were not annealed, and a DNA denaturated and annealed with only the DNA incorporated into cells were used. The base sequences of synthesized oligonucleotides used oiligo A and B which exist in EC1 DNA fragments and oligo C, D, and E which do not exist in EC1 DNA (Table 1 above).

Figure 22:
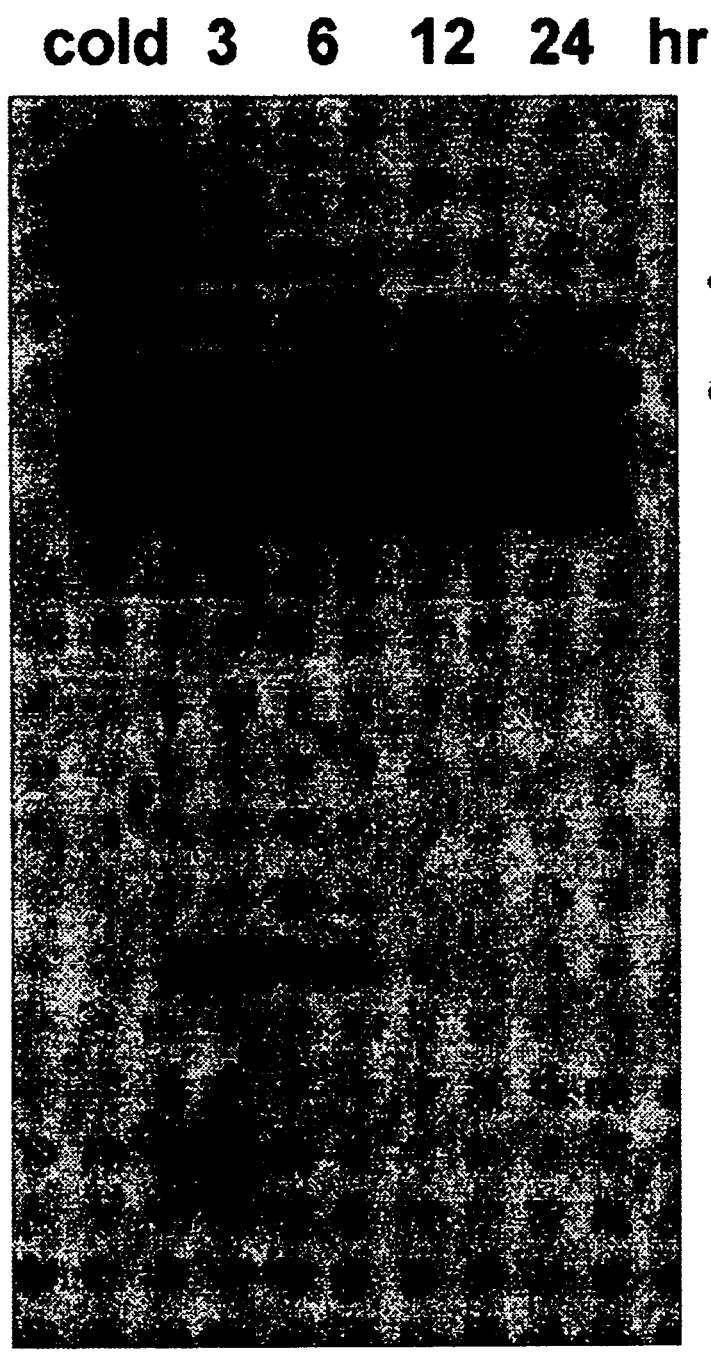
FIG. 22 shows the DNA fragments produced by processing of bacterial DNA in IM9 cells according to the present invention.
Figure 23:
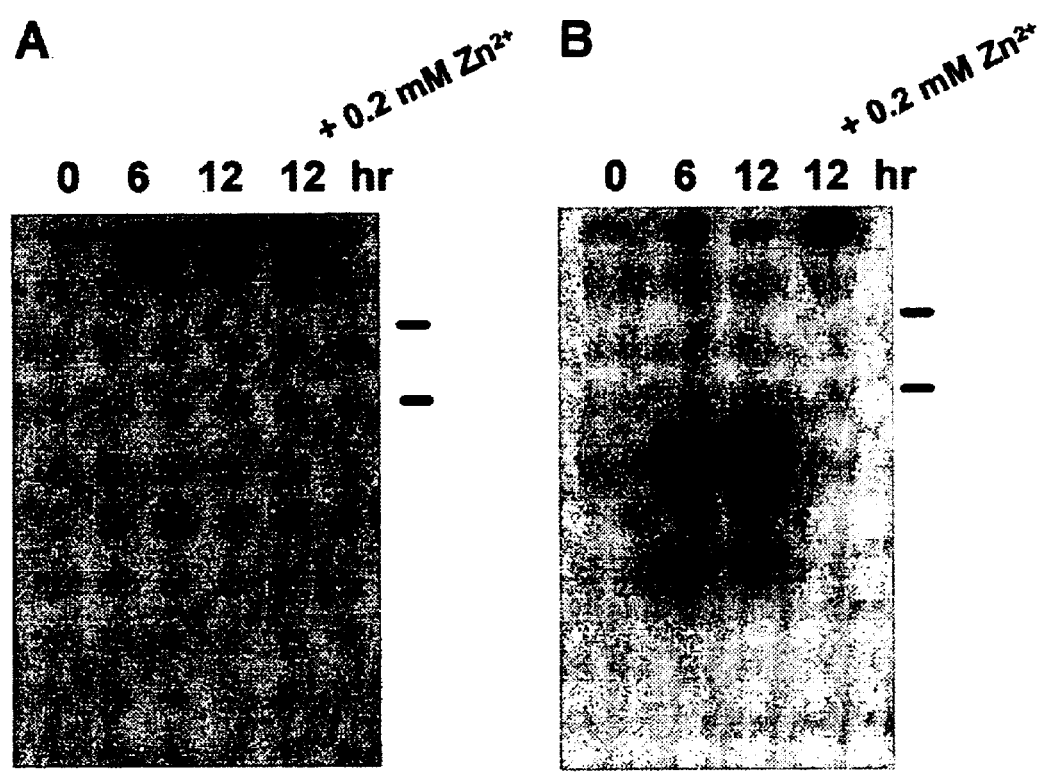
FIG. 23 shows the DNA fragments produced by processing of bacterial DNA in U937 cells according to the present invention (A, labelled DNA incorporation after U937 cells culture in RPMI1640 medium containing 10% PBS for 48 hr; and B, labelled DNA incorporation after TPA (10 ng/ml) treatment for 12 hr).

It was confirmed that exterior DNA was incorporated into human B-lymphoblastic IM9 cell line. U937 cell line, and U937 cell line differentiated by the treatment of TPA and was processed in the cell lines. As a result of a test, the processed product was identified as PCR amplified $^{32}P$-labeled bacterial DNA fragments. The incorporation and processing of exterior DNA in IM9 cell line were confirmed as shown in FIG. 22. 157 bp (EC1) of DNA fragments were not incorporated into cells at 4° C. but was conjugated to the cell membranes. At a temperature of 37° C., the DNA fragments were processed in the cells with the lapse of culture time. In 24 hours, about 10 bp DNA fragments were produced as the end product in 20% native-PAGE. In a subsequent test, the DNA fragments of 10 bp were identified as a single-stranded DNA structure. The DNA fragment also was identified as a single-handed DNA structure on 20% denaturated-PAGE (8.3 M urea). FIG. 23 shows the incorporation of exterior DNA observed in U937 cell line and U937 cell line differentiated by TPA treatment and the processing of the DNA in the cells. However, FIG. 23 B shows the incorporation of exterior DNA and the processing in cells by U937. cell line differentiated by the treatment of TPA As shown in FIG. 23 B, the DNA processing in the cells was inhibited by 0.2 mM of $Zn^{2+}$.

Figure 24:
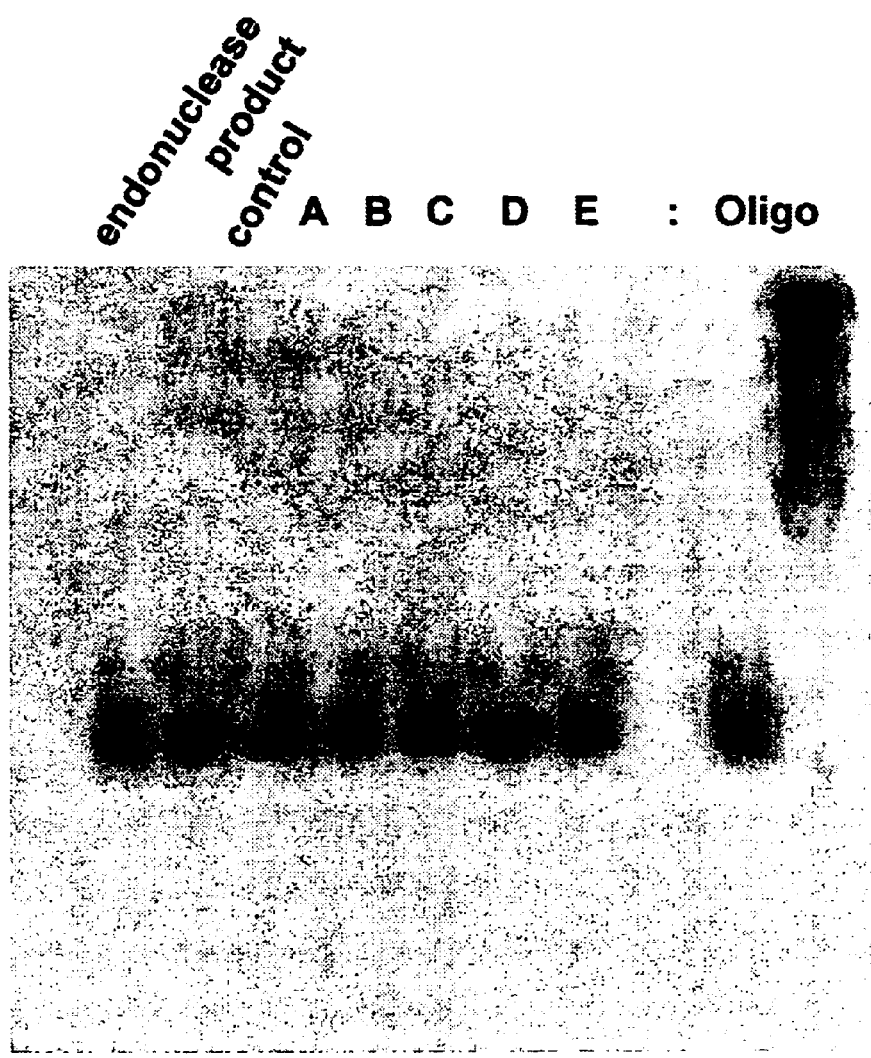
FIG. 24 shows the detection of endonuclease reaction products sequence of the present invention. The endonuclease reaction products were hybridized with synthetic oligonucleotides as described under "Materials and Methods".

The test results demonstrate that the immune cells produce the end product of 10 bases by processing the exterior DNA. The properties of the base sequence of the DNA fragments were also confirmed. After EC1 DNA products amplified by PCR were labeled with $^{32}P$ and were incorporated into cells, the DNA fragments of 10 bases processed by cellular endonucleases were annealed with several types of synthetic oligonucleotides consistent with partial sequences of EC1 to identify the base sequences bound complementarily with the oligonucleotides (FIG. 24). As a result of annealing, the oligonucleotides, the most bound complementarily with the base sequences, were oligo A sequences of Table 1, i.e., the base sequences which have AACGTT motif and are present in EC1 DNA. From the above results, it was clearly confirmed that CpG motif known as the base sequences of bacterial DNA which activates immune cells by enzymatic activity of endonuclease in cells was produced.

3-4 Confirmation on IgM Secretion of IM9 Cell Line by Bacterial DNA

By activating B cells, the oligonucleotides having CpG motif which is known to secrete cytokines and IgM were synthesized. Among the DNA fragments produced by the action of endonuclease, the oligo A present in EC1 and oligo B present in EC2, and oligo E which does not have CpG motif were synthesized (Table 1). EC1 or EC2 PCR products containing several CpG motifs, and several types of DNA were also used in this experiment. To methylate CpG motif, bacterial DNA was digested with endonuclease thereby obtaining the fragments having 100–200 bp. The methylation was carried out by mixing 30 μg of DNA with the buffer solution (10 mM Tris-HCl, pH 7.9, 10 mM $MgCl_2$, 50 mM NaCl, and 1 mM DTT) containing CpG methylase and 160 uM of S-adenosylmethionine, and reacting for 3 hours at 37° C. CpG methylation was confirmed by digesting with Hpa II.

IM9 cell line, human B-lymphoblastic cell line, was cultured in RPMI 1640 medium containing 10% FBS with the cell counts being $2 \times 10^3$/ml at the beginning of culture. After the culture was treated with several types of prepepared oligonucleotides and DNA in 25 ug/ml and was cultured for 24 hours, the cell culture was obtained.

Anti-human-μ-chain-specific IgM (5 ug/ml, Sigma) in 0.1 M carbonate buffer solution (pH 9.6) was incorporated into flat bottom plate in 100 ul/well and then the plate was placed for 16 hours at 4° C. The plate was washed three times with PBS and placed for 2 hours at room temperature. Subsequently, the plate was washed three times with TPBS (0.05% Tween—20 in PBS). Approximately diluted cell culture or purified human IgM (Sigma) in 100 ul/well was introduced. After being placed for 2 hours at room temperature, it was washed three times with TPBS. Horseradish peroxidase-linked anti-human Ig diluted in $\frac{1}{4,000}$ in PBS containing 1% BSA was introduced, and placed for 1 hour at room temperature, and then washed three times with TPBS. The plate was subsequently treated with O-phenylenediamine dihidrochloride in 0.05M phosphate buffer solution (pH 5.0) for 30 minutes. The plate was treated with 0.67 N $H_2SO$, to terminated the reaction and IgM was quantified using microplate reader.

Figure 25:
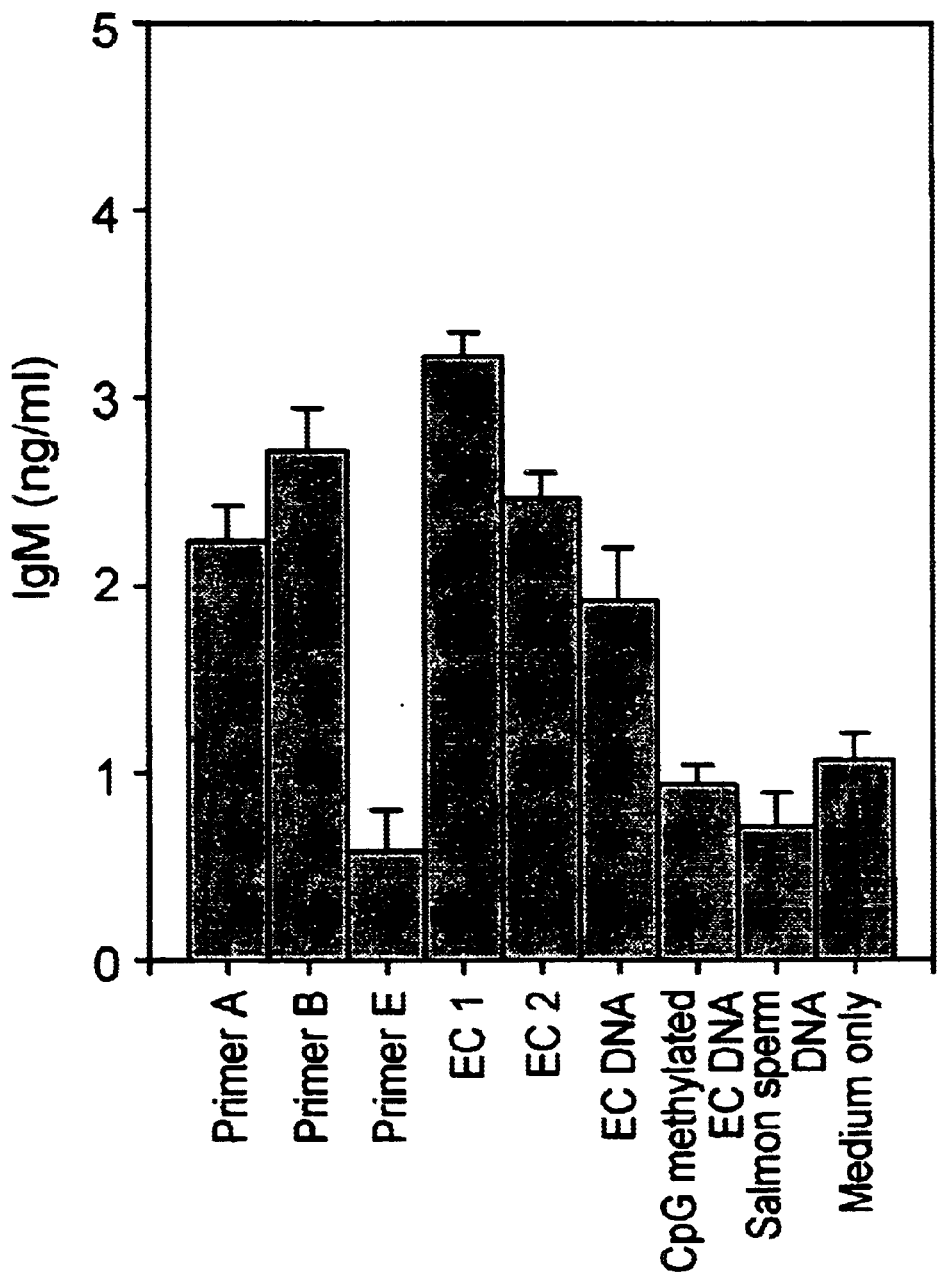
FIG. 25 shows the induction of IgM secretion by CpG motifs in bacterial DNA or oligonucleotides. IM9 cells were stimulated with oligonucleotides (25/ml), or E. coli DNA (25/ml) for 24 hr.

While measuring the amount of IgM secreted 48 hours after treating IM9 cell line with synthetic oligonucleotides, it was confirmed that in oligo A and oligo C having CpG motif 2–3 ng/ml of IgM was secreted but in oligo E having no CpG motif, 0.5 ng/ml of IgM was synthesized (FIG. 25). Further, it was observed that 2–3 ng/ml of IgM was also secreted in bacterial DNA and PCR products (Table 1, EC1, EC2 DNA) of bacterial DNA having several CpG motif. However, if CpG motif of bacterial DNA IgM was methylated and treated in cell line culture, it was not secreted (FIG. 25). In comparison with bacterial DNA, the secretion of IgM was not increased by salmon sperm DNA. From the above results, it was confirmed that CpG motif of bacterial DNA increased the secretion of IgM by activating IM9 cell line and it was consistent with the results of study manifested by using CpG motif synthesized by previous several researchers.

3-5. Properties of the Enzyme Activity of Endonuclease Involving the Processing of Foreign DNA EC1, EC2, and HCl DNA amplified by PCR were labeled with $^{32}$P random-priming method employing random primer and Klenow enzyme. To obtain shorter DNA. EC2 DNA was digested with Alu 1 (Promega Inc.) and the fragments whose 5'-end was labeled with $^{32}$P were used as substrate. To identify the properties of enzyme activity of the endonuclease, EC1 DNA was 5'-end or 3'-end labeled and utilized. 5'-end labeling was carried out by mixing 10 ng EC1 DNA, [γ-$^{32}$P]ATP 50 uCi , kinase buffer solution and 5 units of polynucleotide kinase (Promega Inc.) and reacting form 1 hour at 37° C. 3'-end labeling was carried out by mixing 10 ng EC1 DNA, [α-$^{32}$P]CTP 50 uCi, TdT buffer solution and 5 units of terminal deoxytransferase (Boehringer Mannheim) and reacting for 1 hour at 37° C. and utilized.

5 ng of EC1, EC2 and HCl DNA, prepared above, labeled by random priming method, and EC2 DNA digested with Alu I and 5'-end labeled was mixed IM9 cell culture which does not have FBS and is reacted with constant time interval. Enzyme activities were also measured by increasing the amount of the cell cultures. The reaction mixture was treated with phenol/chloroform to remove protein, precipitated with cold ethanol, and electrophoresed with 20% natural-PAGE and 20% denatured-PAGE (8.3 M urea) in TBE buffer solution. The gel was dried, and autoradiographed. The reaction products were analyzed for enzymatic activities. To compare with the enzymatic activity of DNase I in FBS, 10 ml of RPMI 1640 medium containing 10% FBS was also reacted with several substrates. Further, what effect do $Zn^{2+}$ (1 mM), the inhibitor of endonuclease and EDTA (10 Mm), chelating agent was confirmed to have enzymatic activities. At this time, Bromophenol Blue (BPB) and xylene cynol (XC) were employed as standards of molecular weights. In denatured-PAGE, BPB was positioned at S bases and XC was at 23 bases. In native-PAGE, BPB and XC were at 12 bps and 45 bps, respectively.

Figure 26:
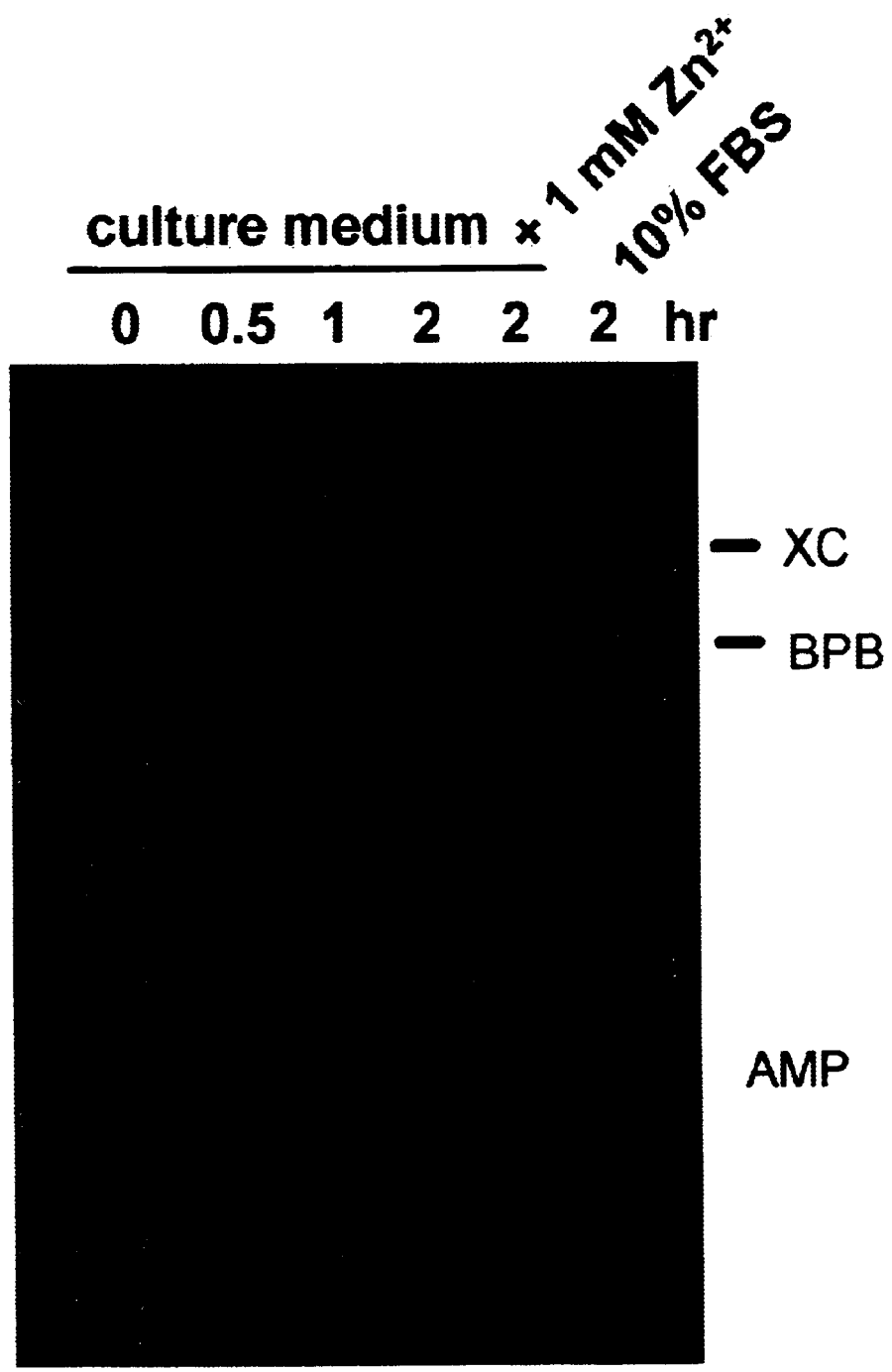
FIG. 26 shows the products of endonuclease reaction using EC1 PCR product as a substrate according to the present invention.
Figure 27:
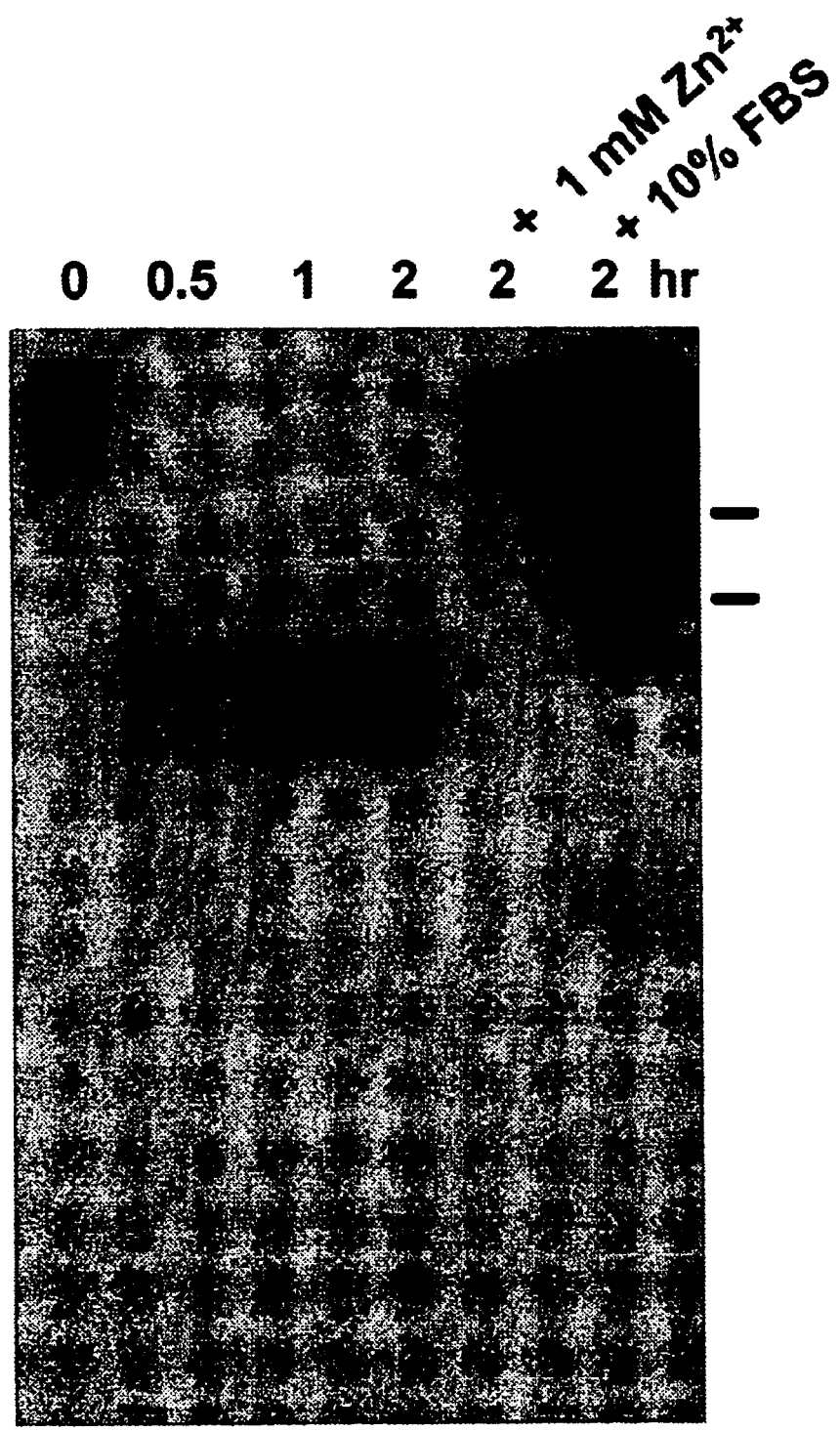
FIG. 27 shows the product of endonuclease reaction using EC2 PCR product as a substrate according to the present invention.
Figure 28:
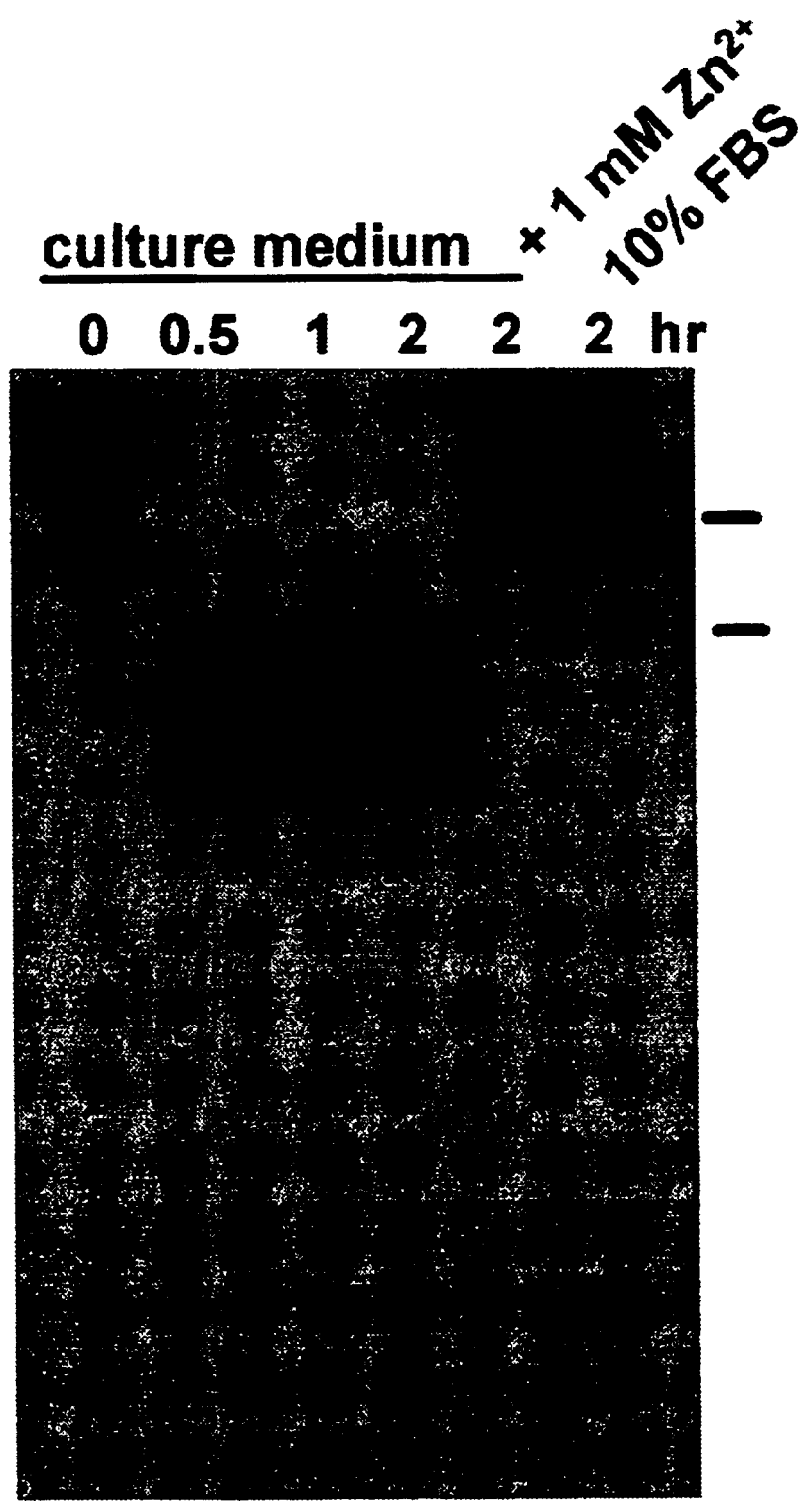
FIG. 28 shows the product of endonuclease reaction using HCl PCR product as a substrate according to the present invention.
Figure 29:
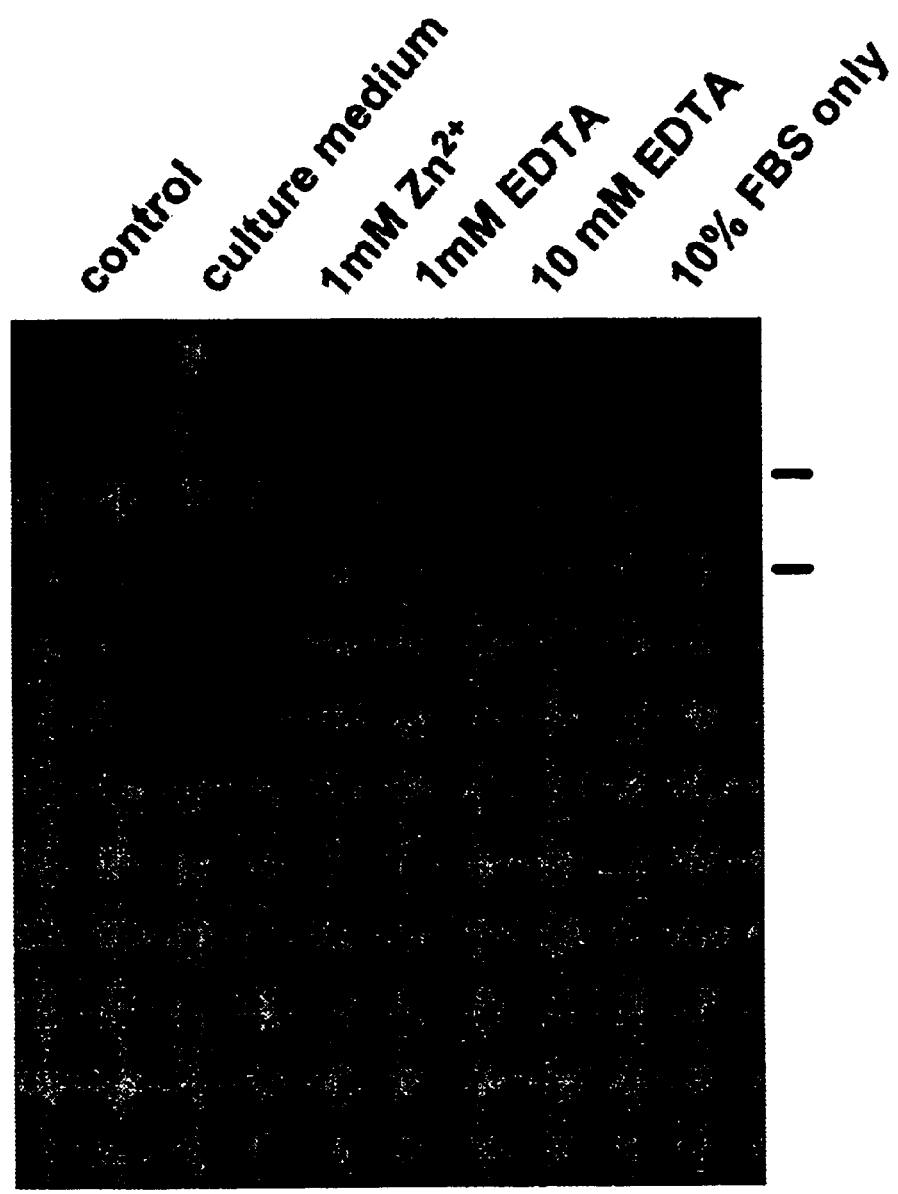
FIG. 29 shows the inhibition of endonuclease activity by $Zn^{2-}$ and EDTA.
Figure 30:
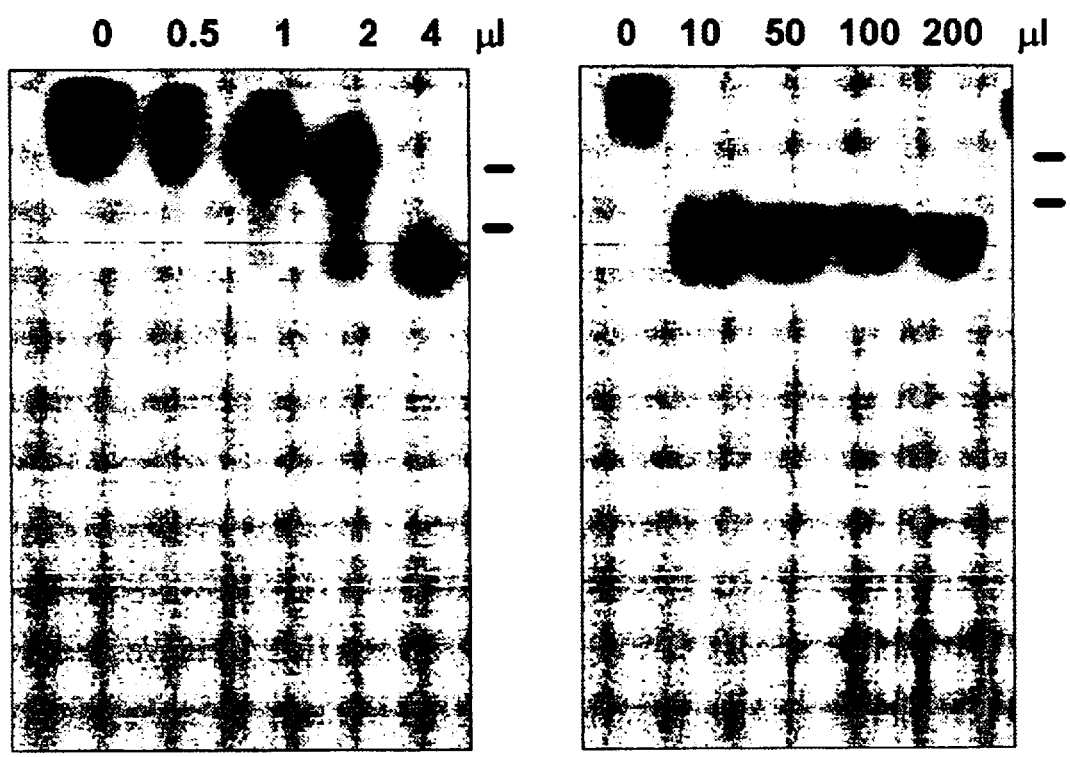
FIG. 30 shows the product of endonuclease reaction from EC1 PCR product reacted with indicated IM9 cell culture medium amounts according to the present invention.
Figure 31:
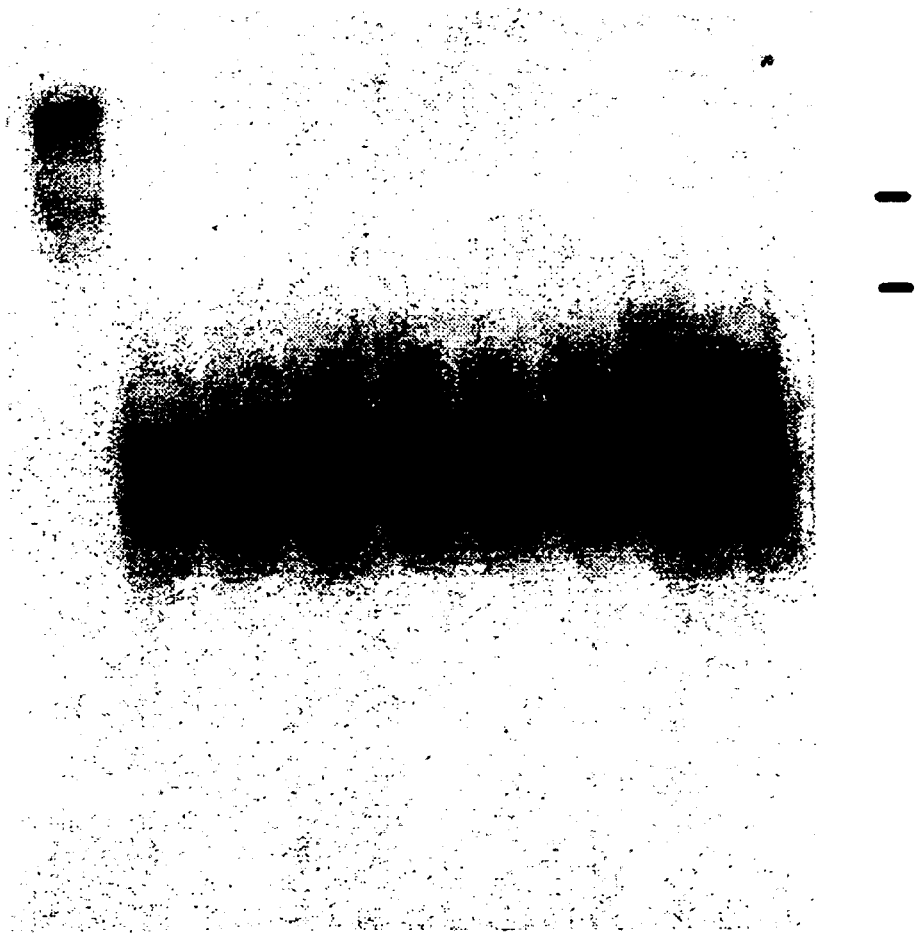
FIG. 31 shows the product from endonuclease reacted with EC1 PCR product for the indicated times according to the present invention.

To identify the properties of the enzyme activity of the endonuclease and the properties of the resulting products, EC1, EC2, and HCl DNA listed in Table 2 were labeled with $^{32}$P by random-priming method and utilized as substrates. It was confirmed that the reaction of these substrates with IM9 cell line cultured in FBS-free-medium resulted in DNA reaction products having about 10 bases as shown in FIGS. 26, 27 and 28. The results show that the endonuclease does not recognize specifically the base sequence of DNA. The endonuclease acted on foreign DNA regardless of base sequences, thereby resulting is DNA fragments having about 10 bases. It was also confirmed that the enzymae activities are inhibited by $Zn^{2-}$, the inhibitor of endonuclease, and EDTA, the chelating agent (FIGS. 26, 27, 28 and 29). By in vitro experiment, it was confirmed that the resulting products are consistent with the reaction products produced by processing the DNA incorporated into cells by the action of endonuclease. It was confirmed that the reaction resultant product of enzymatic activities of endonuclease consists of the DNA fragments having about 10 bases. Even in case the amount of endonuclease was increased (FIG. 30) and the reaction time was kept up to 24 hours, the DNA fragments having about 10 bases, i.e., the reaction resultant product formed by enzymatic reaction were not degraded further. Namely, the endonuclease manifested by this invention does not exert any activity on the DNA fragments having less than about 10 bases.

Figure 32:
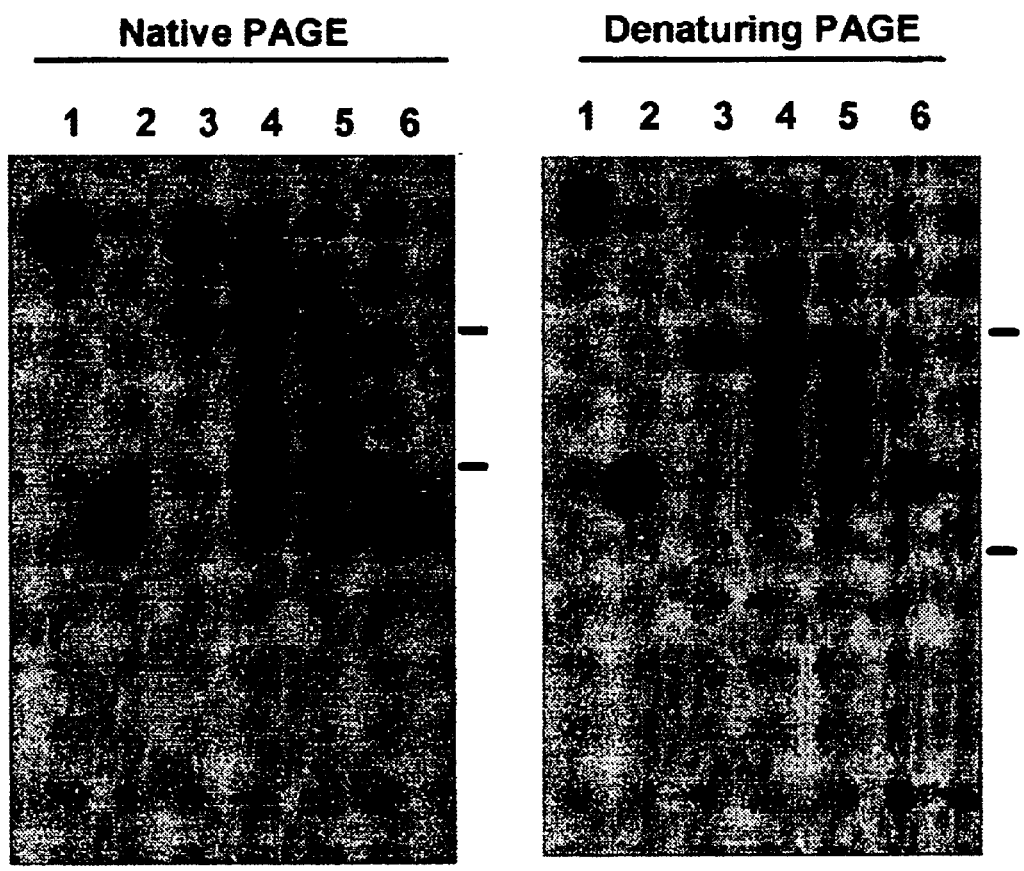
FIG. 32 shows the endonuclease activity comparing EC2 PCR product (157 bp) with short DNA fragment cleaved by Alu 1 (lane 1, $^{32}$P-labelled PCR product; lane 2, endonuclease digested product of lane 1; lane 3, $^{32}$P-labelled short DNA fragment cleaved by Alu 1; lane 4, 30 min reaction of lane 3; lane 5, 1 hr reaction of lane 3; lane 6, 2 hr reaction of lane 3).

FIG. 32 shows several DNA fragments, i.e., endonuclease reaction products formed before EC2 DNA product amplified by PCR was digested with Alu I and the resulting DNA fragments were reacted with endonuclease to produce the end product. The substrates employed in this experiment were labeled with $^{32}$P in 5'-end of DNA reacted with Alu I. The labeled enzymatic reaction resultant product was DNA fragment having about 10 bases. From this fact, it is confirmed that the enzymatic activity of 5'-exonuclease for producing single stranded DNA is not present.

To confirm whether endonuclease of IM9 cell line has 3'-exonuclease or 5'-exonuclease activity, EC2 DNA labeled with $^{32}$P at 5'- or 3'-end was employed as substrate and reacted with endonuclease for 1 hour at 37° C. The reaction resultant products were compared by autoradiography by the same method as stated above. Also, to confirm how enzymatic activity of endonuclease appears in single stranded DNA, labeled DNA was boiled for 5 minutes at 100° C., cooled on inc, and reacted with endonuclease as stated above.

Figure 33:
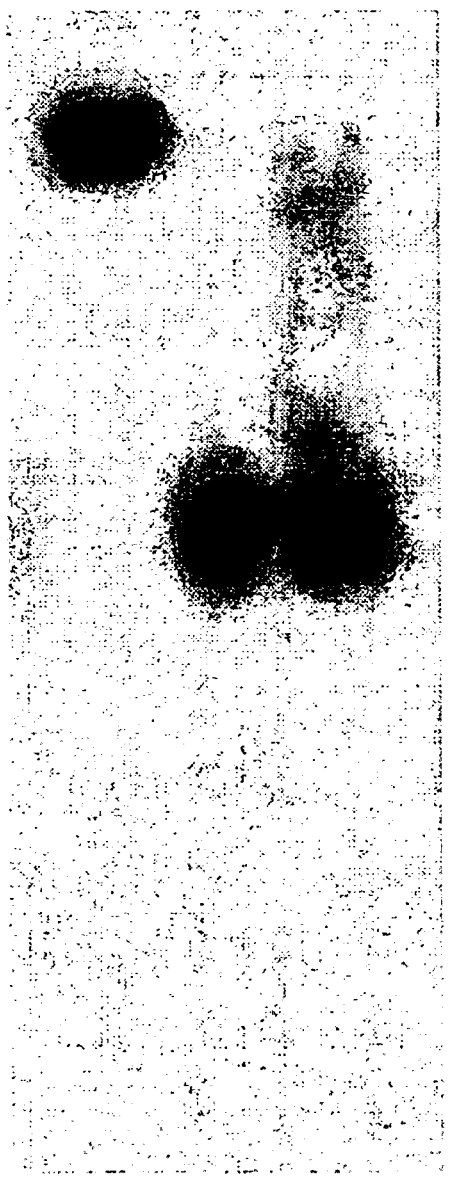
FIG. 33 shows the identification of 3'-exonuclease activity in IM9 cell secreted endonuclease (lane 1, labelled PCR product; lane 2, products of endonuclease reaction on labelled double stranded DNA; lane 3; products of endonulease reaction on labelled single stranded DNA).
Figure 33:

FIG. 33 shows that the DNA fragments having about 10 bases are formed by the action of endonuclease on the substrate labeled in 5'-end (5'-end label, lane 2). The results are the same as shown in FIG. 32. That is, 5'-exonuclease activity was not present in endonuclease. However, the DNA fragments having about 10 bases, i.e., the enzymatic reaction resultant products, were not formed in the substrates labeled with $^{32}$P in 3'-end. After the substrates labeled with $^{32}$P were boiled for 10 minutes at 100° C., cooled on ice to convert to single stranded DNA, and then reacted with endonuclease, labeled DNA fragments having about 10 bases were formed as enzymatic reaction products in DNA substrates labeled in both 5'- and 3'-ends. Based on the test results, 3'-exonuclease activity does not act on single stranded chains.

To compare the reaction resultant products produced by enzymatic activity of endonuclease present in cell cultures, with the products produced by processing in cell and the reaction end product produced by the action of DNase I, 5 units of bovine pancreatic DNase I (Boehringer Mannheim) and EC1 DNA labeled with $^{32}$P by random-priming method were reacted in 10 mM Tris-HCl, pH7.6, 10 mM MgCl$_2$ buffer solution for 1 hour at 37° C. The reaction resultant was run on 20% of natural-PAGE and 20% of denatured-PAGE (8.3M urea), autoradiographed, and compared with the enzymatic reaction resultant product of endonuclease. Also, to confirm that the resultant product of endonuclease activity is present in single stranded chains, it was treated with S1 nuclease. Enzymatic activity of S1 nuclease was confirmed by mixing endonuclease reaction resultant product by the action on the substrates labeled with $^{32}$P by random-priming method with 3 units of S1 nuclease contained in S1 nuclease reaction buffer solution (7×buffer solution, 0.3M Potassium acetate, pH4.6, 2.5M NaCl, 10 mM ZnSO$_4$, 50% glycerol), and reacting the mixtures for 1 hour at 37° C. The reaction resultants were confirmed by autoradiography by the same method as stated above.

Figure 34:
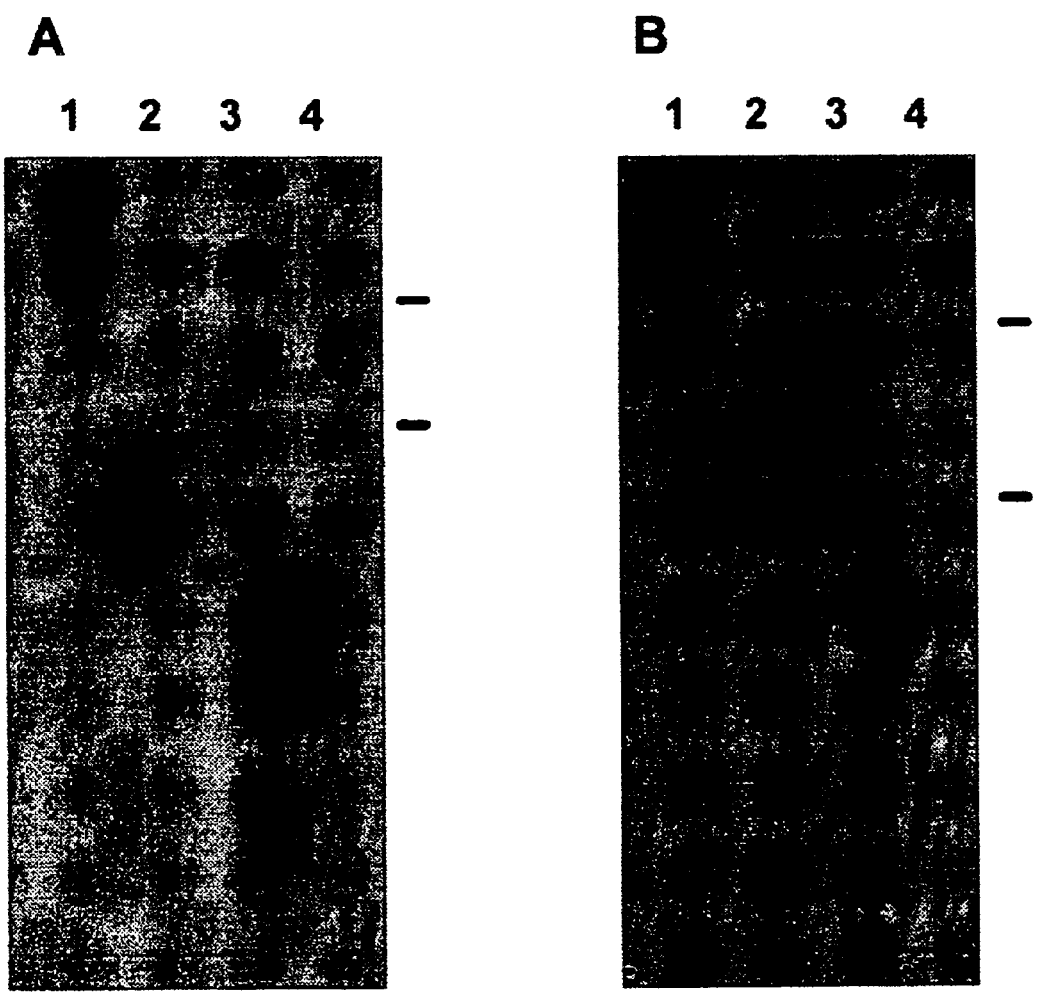
FIG. 34 shows the comparison between endonuclease reaction product and processed product by IM9 cells with DNase 1 reaction product (lane 1, labelled PCR product; lane 2, reaction product of IM9 cell culture medium; lane 3, processed product in IM9 cells; lane 4, DNase 1 reaction product; Panel A, 20% native-PAGE in TBE buffer; Panel B. denatured-urea (8.3 M)-PAGE in TBE buffer)
Figure 35:
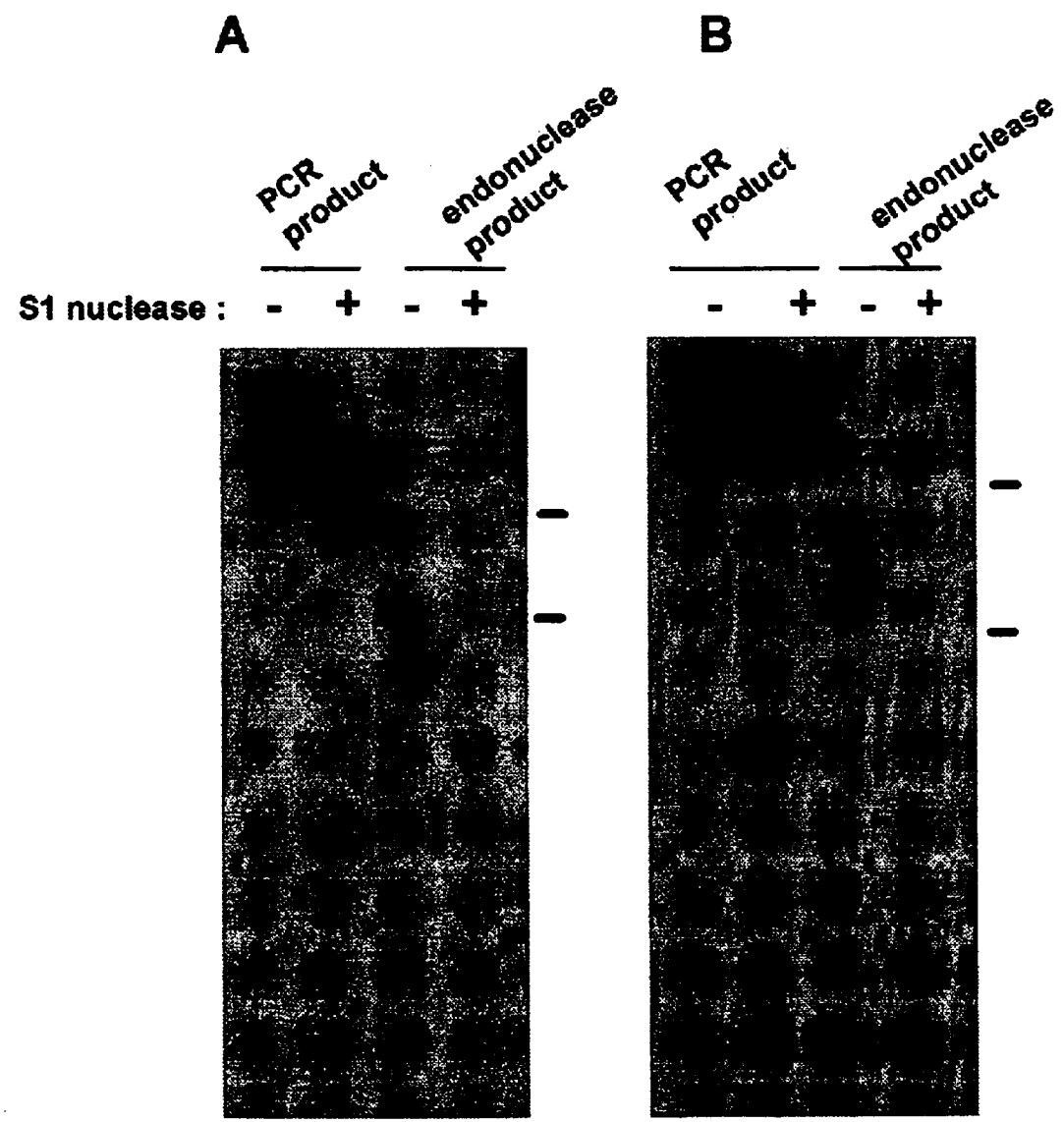
FIG. 35 shows the identification of single stranded fragments derived from endonuclease reaction by S1 nuclease reaction (A, 20% native-PAGE in TBE buffer; B, 20% denatured-Urea (83 M)-PAGE in TBE buffer).

By the comparison of the resultant product produced by the enzymatic activity of endonuclease and the reaction product produced by the action of DNase I, as shown in FIG. 34, the DNA reaction products processed by the endonuclease of cell cultures (lane 2) and cellular endonuclease (lane 3) are all the DNA fragments having about 10 bases. However, by the action of DNase I (lane 4), the DNA fragments were degraded into less than 10 bases. The fragments were subsequently degraded into mononucleotides. Also, to confirm whether the products obtained by endonuclease reaction are present in single stranded form, the products were treated with S1 nuclease and the enzymatic reaction products were observed. When the reaction products having about 10 bases, i.e., the products of endonuclease, were reacted again with S1 nuclease, as shown in FIG. 35, they were completely degraded into mononucleotides. This is a clear evidence proving that the DNA fragments having about 10 bases, produced by the enzymatic activity of endonuclease are present in single stranded form.

EXAMPLE 4

Purification and Identification of Endonuclease Secreted from IM9 Cell Line

It was now found that IM9 cell line synthesized and secreted Mg$^{2+}$-dependent endonuclease which is distinct from nuclease known so far. It was also found that the endonuclease is present in the nucleus of IM9 cell line and participates in the apoptosis process. The endonucleases involved in the apoptosis include Mg$^{2+}$-dependent endonuclease (Anzai N. et al (1995) *Blood* 86, 917–923; Kawabata H. et al (1993) *Biochem. Biophys. Res. Commun.* 191, 247–254; Sun X. M., and Cohen G. M. (1994) *J. Biol. Chem.* 269, 14857–4860;, and Kawabata, H. et al (1997) Biochem. Biophys. Res. Commun. 233, 133–138), Ca$^{2+}$/Mg$^{2+}$-dependent endonuclease (Stratling W. H. et al (1984) *J. Biol. Chem.* 259, 5893–5898; Pandey S. et al (1993)*Biochemistry* 32, 9129–9136). DNase I (Peitech M. C. et al (1993) *EMBO J.* 12, 371–377), NUC18 (Kawabata, H. et al (1997) *Biochem. Biophys. Res. Commun.* 233, 133–138) and so on. However, the purification, biochemical characteristics, and physiological function of the above known endonucleases have not been clearly defined. Furthermore, there was no report on any endonucleases which may recognize bacterial DNAs as foreign agents and process them. By the present invention, the endonuclease synthesized and secreted by IG9 cell line was purified and the property thereof was now identified.

4-1 Protein Source and Assay for the Enzyme Activity of Endonuclease

IM9 cell line secreting the endonuclease was massively cultured in RPMI1640 medium containing heated 10% FBS and the resulting cell culture was used as enzyme source. After the cell culture was centrifuged at 1,500×g for 5 minutes, IM9 cell line was discarded and the cell culture solution was recovered. 10 l of cell culture solution was centrifuged at 14,000×g for 30 minutes at 4° C., and the resulting supernatant was used as enzyme source.

During the purification of the endonuclease, the enzyme activity was measured as the degree of the formation and digestion of linear DNA from supercoiled plasmid DNA used as a substrate. 100 ng of plasmid DNA was added to 20 mM Tris-HCl pH 7.0, buffer solution containing 10 mM MgCl$_2$, and the mixture was reacted with 20 ul of a sample obtained during the protein purification at 37° C. for 10 minutes. The enzyme reaction was terminated with the DNA sample buffer and the enzyme activity was assayed by electrophoresis on a 1% agarose gel.

4.2 Purification of Endonuclease

The cell culture solution was saturated to a concentration of 80% by slowly adding NH$_4$SO$_4$, and then centrifuged at 14,000×g. The resulting precipitate was dialyzed overnight in 20 mM sodium acetate buffer solution, pH 5.2. A 5 ml aliquot of the enzyme solution was loaded on Mono-S column (0.5×5.0 cm, Pharmacia LKB) preequilibrated with 5 ml of the same buffer solution: The protein was first eluted by a linear concentration gradient of 0–0.08 M NaCl (15 ml) in the same buffer solution and then was passed over 15 ml of the same buffer solution containing 0.08 M NaCl. Subsequently, the protein was again eluted with a linear concentration gradient of 0.08–0.2 M NaCl (20 ml). The volume of each fraction was 1 ml and the flow rate was 0.5 ml/min. The above procedure was repeated and the fraction containing the endonuclease was pooled and concentrated using Centricon, and then equilibrated with 50 nM of sodium phosphate buffer solution, pH. 7.0, containing 1.5 M (NH$_4$)$_2$SO$_4$. This enzyme source was loaded on a RESOURCE PHE column (0.64×30 mm, 1 ml, Pharmacia LKB) and the hydrophobic interaction chromatography was carried out. The column was washed with 15 ul of the same buffer solution and the protein was eluted with a linear concentration gradient of 1.5–0 M (NH$_4$)$_2$SO$_4$ (25 ml). The fraction with the enzyme activity was concentrated in Centricon and equilibrated with 20 mM Tris-HCl buffer solution, pH 7.0.

Figure 36:
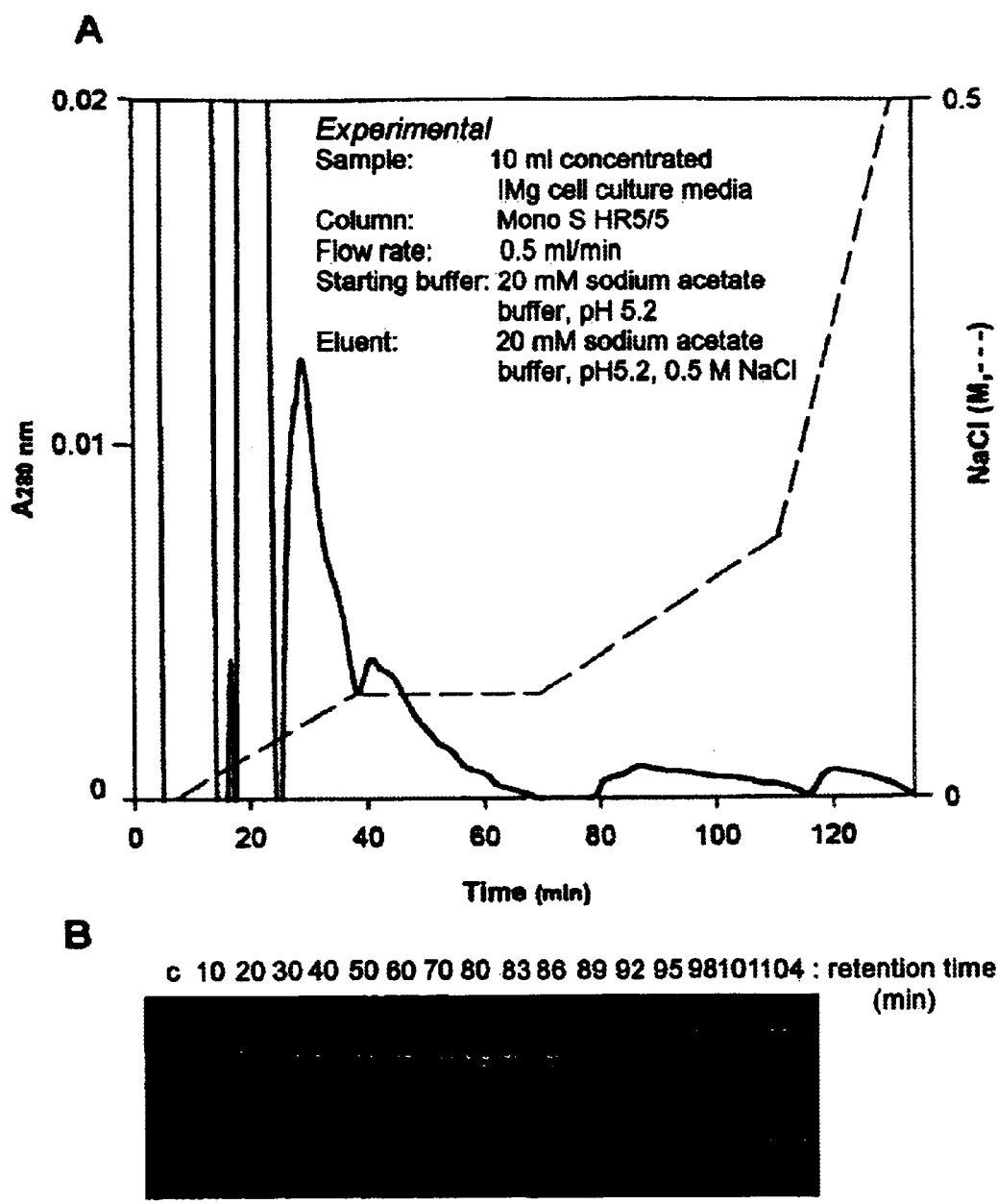
FIG. 36 shows the chromatographic fractionation of IM9 cell culture medium by Mono S HR5/5 ion exchange chromatography(A, ion exchange profile of IM9 culture medium; B, the enzyme activity was determined at the indicated retention times by resolving the reaction products on a 1% agarose gel).
Figure 37:
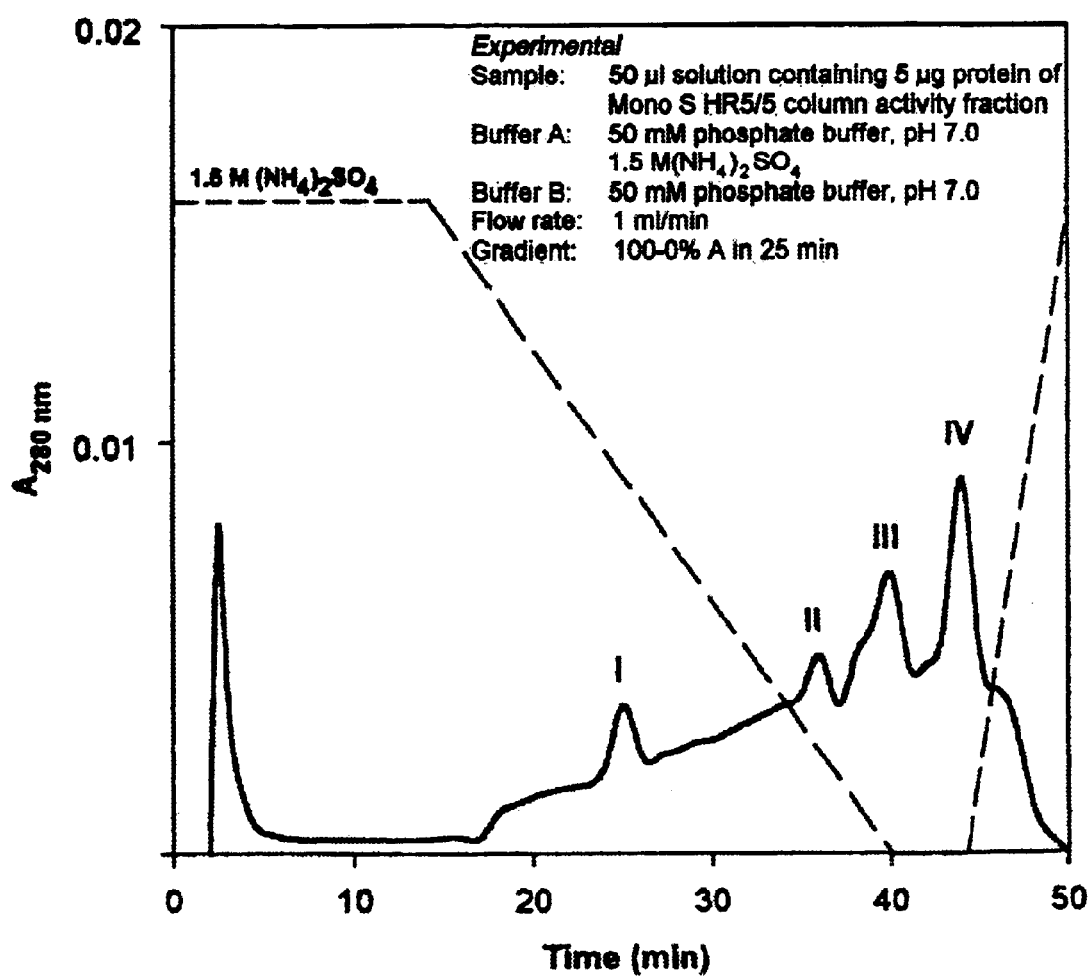
FIG. 37 shows the purification of endonuclease by RESOURCE PHE hydrophobic interaction chromatography (A, hydrophobic interaction profile of activity fraction obtained from ion exchange chromatography; B, the enzyme activity was determined at the peak fractions by resolving the reaction products on 1% agarose gel.
Figure 37:
Figure 38:
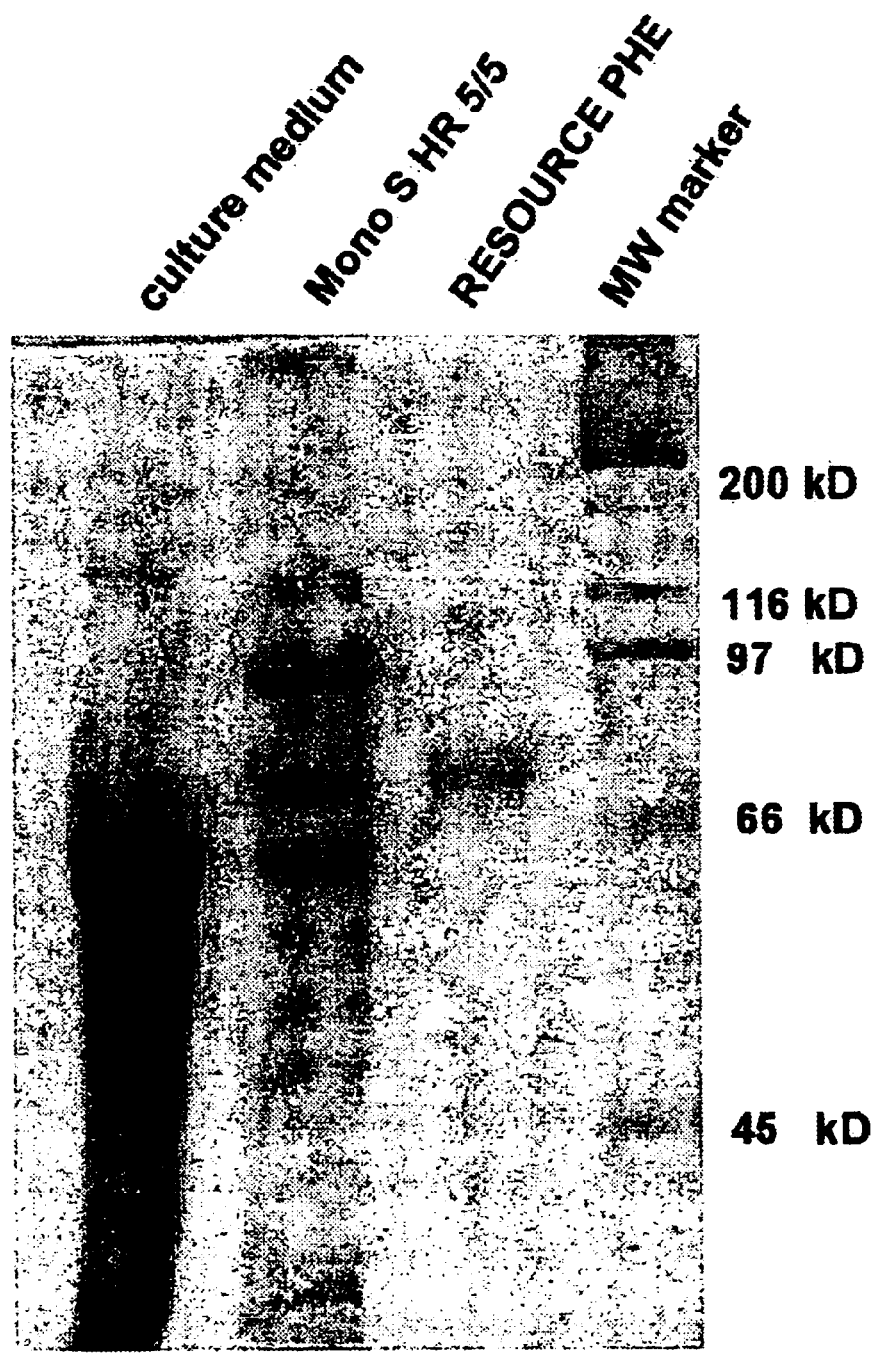
FIG. 38 shows the SDS-PAGE of purified endonuclease by ion exchange chromatography and hydrophobic interaction chromatography.

IM9 cell culture solution was concentrated over ammonium sulfate and used for purification. The differential precipitation over ammonium sulfate was conducted depending on the concentration difference, but did not significantly effect on the isolation of the enzyme. Thus, culture solution was concentrated to 80% and the protein was precipitated for the purification. The enzyme activity in the sample passed over Mono S column was recovered by a linear concentration gradient of 0.08–0.2 M NaCl (FIG. 36). The fraction exhibiting the activity on cation-exchange resin was pooled and passed over RESOURCE PHE column in a hydrophobic interaction chromatography. When the protein was eluted with 1.5–0 M $(NH_4)_2SO_4$ linear concentration gradient, the activity of endonuclease was detected in the protein fraction obtained from 0.74M $(NH_4)_2SO_4$ gradient among the above gradients (FIG. 37). 10 ug of the endonuclease was purified from 10 l of IM9 cell culture solution containing about 10 g of protein.

4-3 Determination of Molecular Weight by the Nature Porous Gradient PAGE and SDS-PAGE The fraction exhibiting the enzyme activity on the cation-exchange resin chromatography was pooled and concentrated in Centricon. The concentrated solution was loaded on 4–15% linear gradient of acrylamide gradient gel and electrophoresis was performed with 4–5 mA for 18 hours at 4° C. Then, the gel was stained with coomassie brilliant blue R-250 to detect the protein band. The gel portion of the protein band was cut to make a small piece prior to the staining and was eluted with 20 mM Tris-HCl buffer solution, pH 7.0, for 8 hours at 4° C. The enzyme activity among the eluted protein fraction was detected using the supercoiled plasmid DNA as a substrate. The enzyme a activity fraction was concentrated and separated by SDS-polyacrylamide gel electrophoresis. The concentrations of the staking gel and the running gel were 4% and 7%, respectively. The standard protein in the native porous gradient PAGE was a mixture of ferritin (440 kD), catalase (232 kD), lactate dehydrogenase (140 kD) and bovine serum albumin (87 kD). The standard protein in the SDS-PAGE was a mixture of myosin (200 kD). β-galactosidase (116.3 kD), phosphorylase B (97.4 kD), bovine serum albumin (66.2 kD) and ovalbumin (45 kD).

Figure 39:
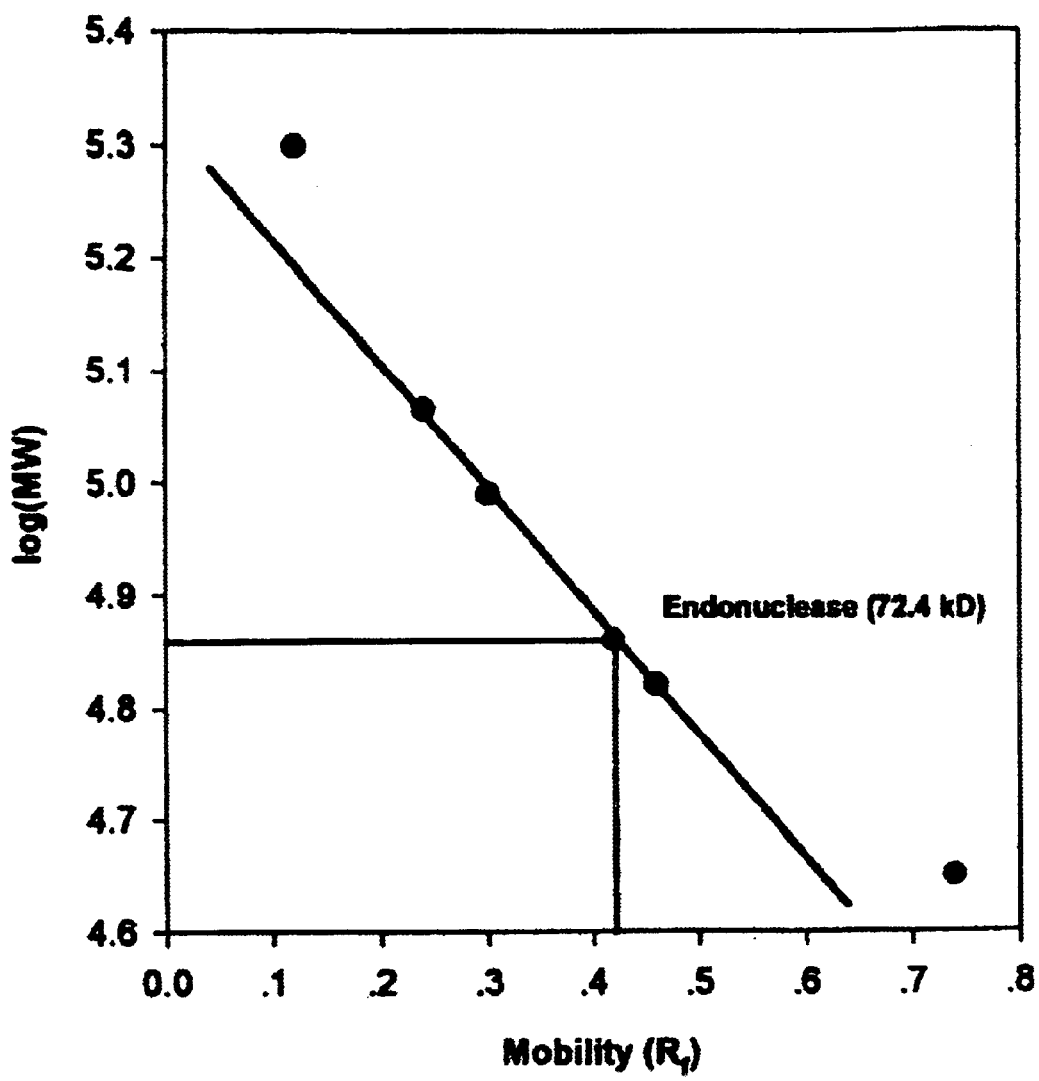
FIG. 39 shows the molecular weight determination of purified endonuclease by SDS-PAGE (marker proteins are myosin (200 kD), β-galactosidase (116.3 kD). phosphorylase B (97.4 kD), bovine serum albumin (66.2 kD) and ovalbumin (45 kD)).
Figure 40:
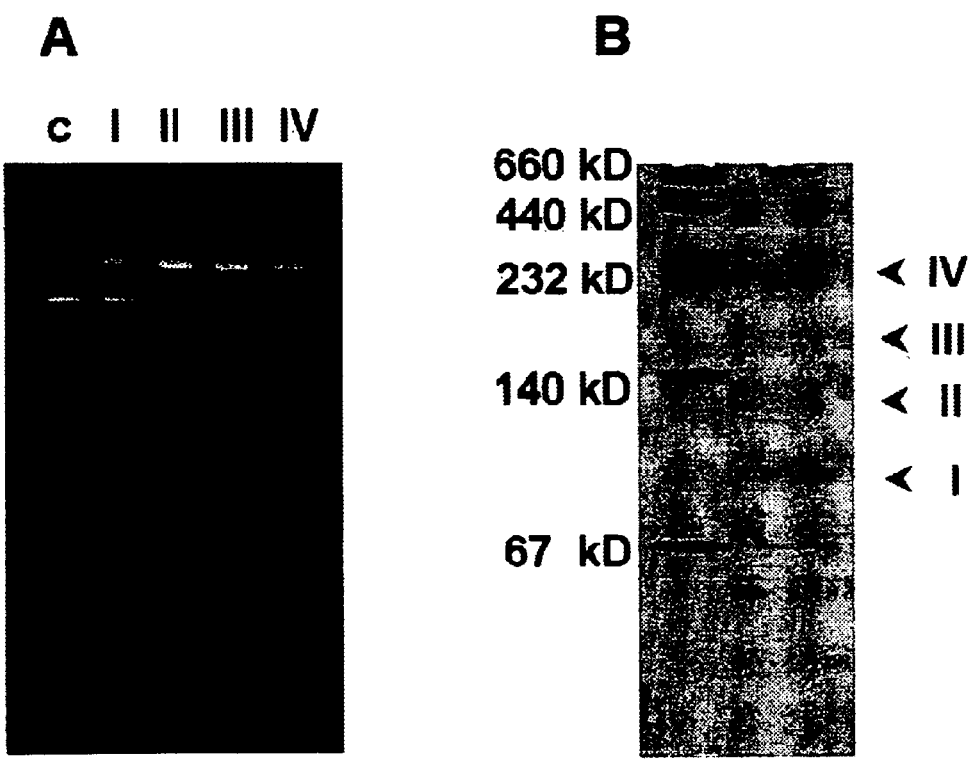
FIG. 40 shows the native-pore gradient gel electrophoreis (4–15%) of Mono S chromatography fraction containing activity (B) and endonuclease activity of eluted protein from gel band of panel a on agarose gel electrophoresis (A).
Figure 41:
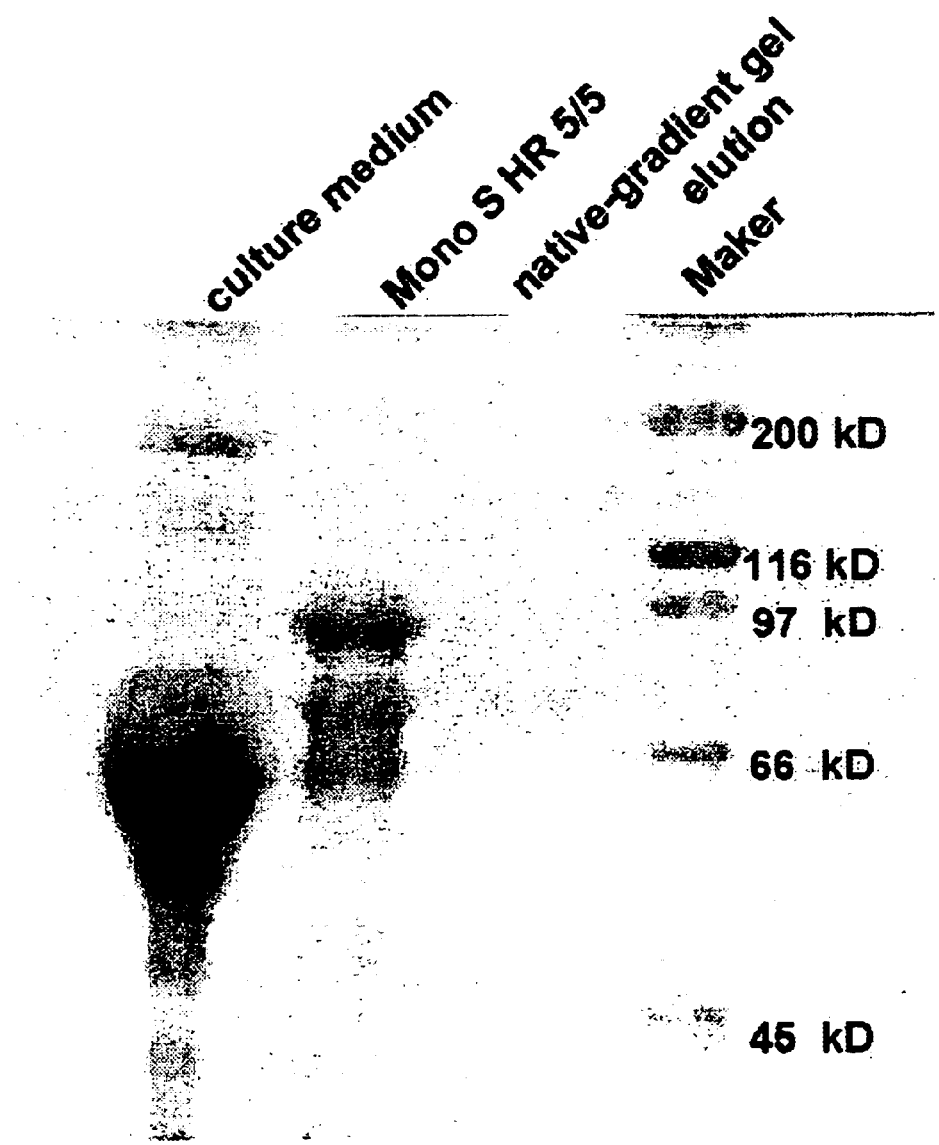
FIG. 41 shows the SDS polyacrylamide gel electrophoresis of purified endonuclease by ion exchange chromatography and native-gradient PAGE gel elution of activity band.

The enzyme activity fraction eluted on Mono S column was concentrated and 4–15% native porous gradient gel electrophoresis was carried out to detect the protein band showing the enzyme activity (FIG. 40). The protein band exhibiting the enzyme activity was not shown as clear single band and was spread around 140 kD as compared with the standard protein. The protein band exhibiting the enzyme activity was eluted. After concentration, electrophoresis was conducted on SDS-PAGE (FIG. 41). The purified protein band was shown at the same site as the endonuclease purified by chromatography and the molecular weight of the protein was determined as about 72.4 kD (FIG. 39). A comparison of the results of the native porous gradient gel electrophoresis and SDS-PAGE revealed that the endonuclease exhibits the enzyme activity in the form of homodimer.

4-4 Characterization of the Purified Enzyme

Nuclei were isolated from U937 cell from which any endonuclease enzyme activity was not detected for 4 hours, and were used as substrate. The specificity of the enzyme activity was confirmed by adding 1 mM $Ca^{2+}$, 1 mM $Mg^{2+}$, 1 mM $Zn^{2+}$, and EDTA to 20 mM Tris-HCl buffer solution, pH 7.0 containing the isolated nuclei and the reaction was allowed for 10 minutes at 37° C.

Figure 42:
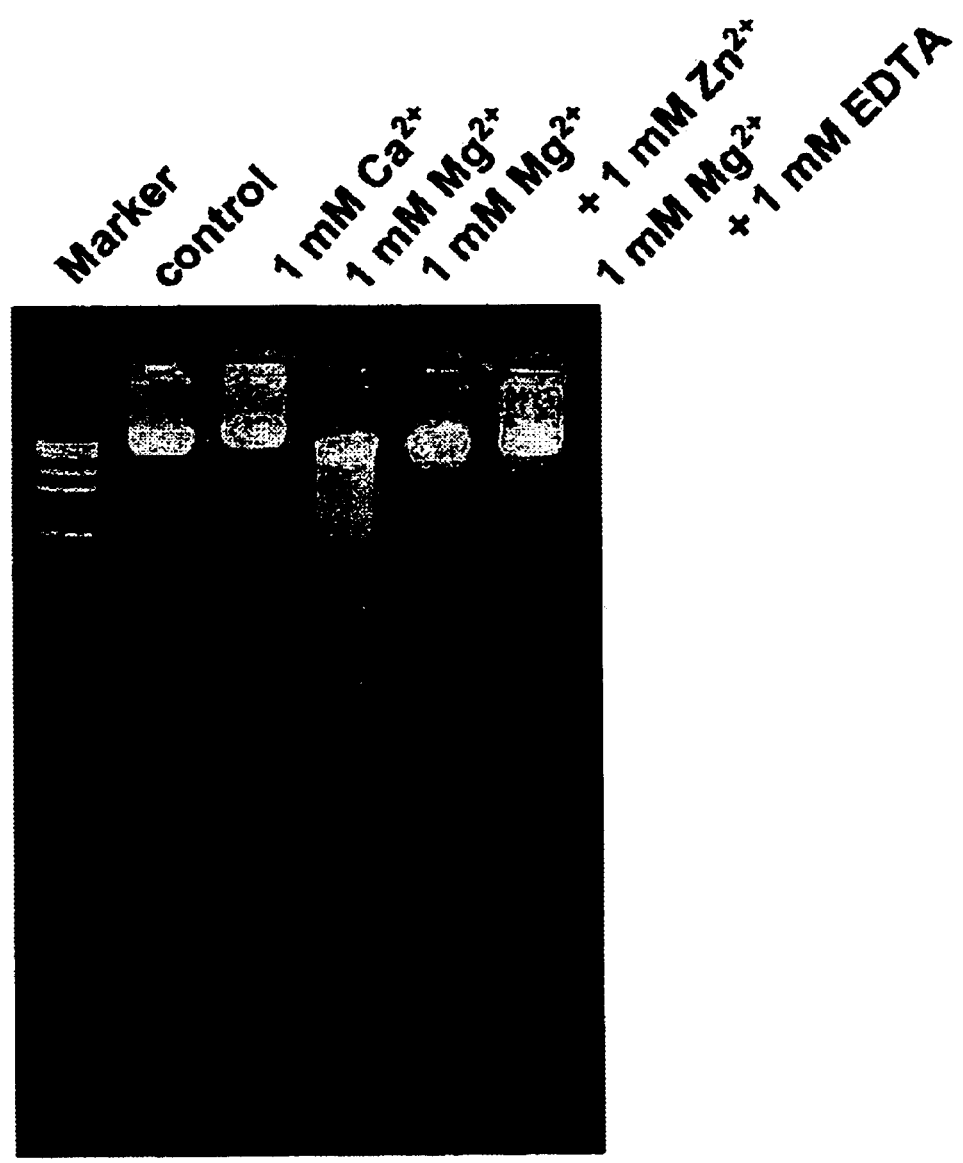
FIG. 42 shows the effects of cation on purified endonuclease activity in isolated U937 cell nuclei.

When the nuclei isolated from U937 cell line were used as substrate the activity of the purified enzyme was exhibited in the presence of $Mg^{2+}$ and was completely inhibited by $Zn^{2+}$, apoptosis inhibitor, and EDTA, chelating agent (FIG. 42). The characteristic enzyme activity was consistent with that of the above enzymatic activity.

Industrial Availability of the Invention

The endonuclease of the present invention is able to degrade foreign bacterial DNA and incorporate the DNA fragments into cells. The DNA incorporated into cells is processed by the intracellular endonuclease to produce oligonucleotide including CpG motif and then the immune cell is activated by the CpG motif to promote the secretion of antibody. Accordingly, the endonuclease of the present invention is industrially valuable as an pharmaceutical immune adjuvant.

What is claimed is:

1. A purified endonuclease enzyme which is secreted from a human B lymphoblastic IM9 cell line and recognizes bacterial DNA as a foreign agent and processes the DNA to produce about 10 bp single-stranded oligonucleotides including a CpG motif which is involved in immune response, wherein the endonuclease has the following physiochemical properties:

a) molecular weight: about 72.4 kD by SDS-PAGE;
b) divalent cation dependency: $Mg^{2+}$ dependent; and
c) optimal pH; about 6.5 to 7.5.

2. The endonuclease enzyme according to claim 1, wherein the mobility distance of the enzyme activity by native-PAGE is apparently distinct from that of DNase I.

* * * * *